United States Patent [19]

Sano et al.

[11] Patent Number: 5,736,356
[45] Date of Patent: Apr. 7, 1998

[54] **TRANSGLUTAMINASE ORIGINATING FROM *CRASSOSTREA GIGAS***

[75] Inventors: Kohichiro Sano; Yoshiyuki Kumazawa; Hisashi Yasueda; Katsuya Seguro; Masao Motoki, all of Kawasaki, Japan

[73] Assignee: Ajinomoto Co., Inc., Tokyo, Japan

[21] Appl. No.: 525,654

[22] PCT Filed: Jan. 30, 1995

[86] PCT No.: PCT/JP95/00117

§ 371 Date: Sep. 28, 1995

§ 102(e) Date: Sep. 28, 1995

[87] PCT Pub. No.: WO95/20662

PCT Pub. Date: Aug. 3, 1995

[30] Foreign Application Priority Data

Jan. 28, 1994 [JP] Japan ................................. 6-008283
Jan. 13, 1995 [JP] Japan ................................. 7-003876

[51] Int. Cl.[6] .................. C12N 15/54; C12N 1/19; C12N 1/21; C12N 1/00; C12N 15/63; C12N 9/12; C12P 21/00
[52] U.S. Cl. .................. 435/68.1; 435/193; 435/172.3; 435/252.3; 435/252.33; 435/254.11; 435/320.1; 435/325; 435/254.21; 536/23.2; 426/573
[58] Field of Search .................. 435/193, 172.3, 435/320.1, 252.3, 252.33, 254.11, 68.1, 254.21, 325; 536/23.2; 426/573

[56] References Cited

PUBLICATIONS

The Journal of Biological Chemistry, vol. 246, No. 4, pp. 1093–1098, Feb. 25, 1971, John M. Connellan, et al., "Structural Properties of Guinea Pig Liver Transglutaminase".

The Journal of Biological Chemistry, vol. 268, No. 16, pp. 11565–11572, Jun. 5, 1993, Toshiya Kanaji, et al., "Primary Structure of Microbial Transglutaminase From Streptoverticillium sp. Strain s–8112*".

Bulletin of the Japanese Society of Scientific Fisheries, vol. 36, No. 2, 1970, pp. 169–172, Reiji Takashi, et al. "Studies on Muscular Proteins of Fish–II. Preparation of Actomyosin From Carp Muscle" (with partial English translation).

Nippon Suisan Gakkaishi, vol. 57, No. 6, pp. 1203–1210, 1991, Hajime Kishi, et al., "Reactivity of Muscle Transglutaminase on Carp Myofibrils and Myosin B".

Molecular Cloning, Second Edition, pp. 718–721, Sambrook, et al., "Extraction, Purification, and Analysis of Messenger RNA From Eukaryotic Cells".

Biochemistry, vol. 27, No. 8, pp. 2898–2905, 1988, Koji Ikura, et al., "Amino Acid Sequence of Guinea Pig Liver Transglutaminase From Its cDNA Sequence".

Journal of Biochemistry, vol. 104, No. 1, pp. 30–34, 1988 Naoto Tonouchi, et al., "High–Level Expression of Human BSF–2/IL–6 cDNA in *Escherichia coli* Using a New Type of Expression–Preparation System".

*Primary Examiner*—Charles L. Patterson, Jr.
*Assistant Examiner*—Gabriele E. Bugaisky
*Attorney, Agent, or Firm*—Oblon, Spivak, McClelland, Maier & Neustadt, P.C.

[57] ABSTRACT

The present invention relates to a transglutaminase originating from *Crassostrea gigas*, a gene coding for the transglutaminase, a plasmid carrying the gene, a microorganism transformed with the plasmid, a method for producing an intended transglutaminase by cultivating the microorganism and a method for gelating a protein using the transglutaminase originating from *Crassostrea gigas*. When comparing with other transglutaminases, the transglutaminase originating from *Crassostrea gigas* has novel characteristic properties such that it can be activated by the action of calcium ions and that it is further activated by the addition of sodium chloride and/or potassium chloride and it is of utility value, in particular, as a gelling agent for foods.

22 Claims, 12 Drawing Sheets

LANE 1, MOLECULAR WEIGHT MARKER
LANE 2, PURIFIED TG OF <u>CRASSOSTREA GIGAS</u>

TEMP. (°C)

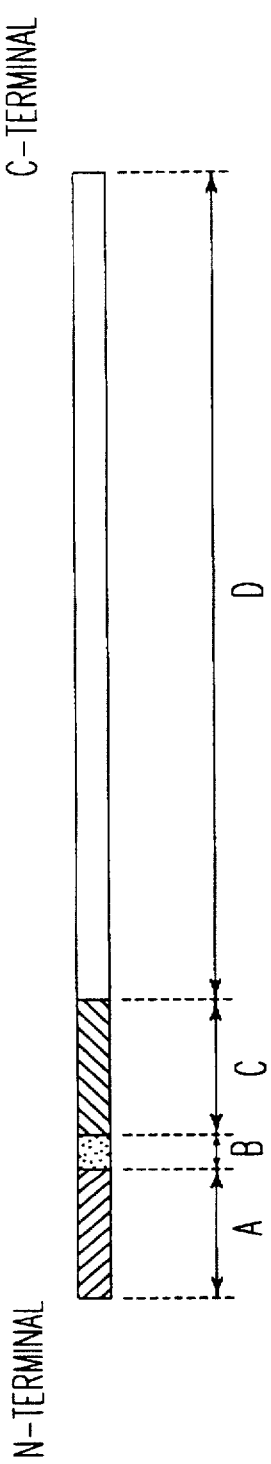

FIG. 13

A  SEQUENCE OF AMINO ACID ORIGINATED FROM B-GALACTOSIDASE (17 AMINO ACID RESIDUES)
TMITPSAQLTLTKGNKS

B  GLUTAMIC ACID RESIDUE (1 RESIDUES)

C  AMINO ACID SEQUENCE ENCODED BY NON-CODING REGION OF cDNA CRASSOSTREA GIGAS TGas (25 AMINO ACID RESIDUES)
ISKRVVKEIYESVCYFHTSSWEYI

D  AMINO ACID SEQUENCE ENCODED BY CODING REGION OF cDNA OF CRASSOSTREA GIGAS TGase (771 AMINO ACID RESIDUES)

TRANSGLUTAMINASE ORIGINATING FROM *CRASSOSTREA GIGAS*

TECHNICAL FIELD

The present invention relates to a novel transglutaminase, i.e., transglutaminase originating from Japanese oyster (zoological name: *Crassostrea gigas*), a method for gelating a protein using the same, a gene coding for the transglutaminase originating from *Crassostrea gigas*, a recombinant plasmid carrying the gene incorporated therein, a transformant comprising the plasmid introduced therein, a method for preparing the transglutaminase originating from *Crassostrea gigas* comprising the step of cultivating the transformant or the like.

BACKGROUND OF THE INVENTION

The transglutaminase is an enzyme which catalyzes a reaction for converting, into a variety of primary amines, the acyl groups on the γ-carboxyamide groups of glutamine residues present in a protein or a peptide chain.

When the ε-amino group of a lysine residue present in a protein acts as a receptor of acyl group, ε-(γ-glutamyl)-lysine cross/ink are intramolecularly and intermolecularly formed. For this reason, if such intermolecular crosslinking takes place in a protein, the protein is converted into a crosslinked high molecular weight polymer through the polymerization. Moreover, if a primary amine such as lysine or a derivative thereof acts as an acyl group-receptor, the primary amine is incorporated into a protein serving as an acyl group-donor. In addition, a water molecule also serves as an acyl group-receptor and glutamine residues of a protein are converted into glutamine acid residues through deamidation in this case.

Until now, there have been identified various transglutaminases originating from mammals, microorganisms and fishes. Those originating from mammals have been discovered and identified in various animals and internal organs, including the transglutaminase originating from the liver of *Cavia porcellus* (Connellan, et al., Journal of Biological Chemistry, 1971, Vol. 246, No. 4, pp. 1093–1098) as a representative example.

As an example thereof derived from a microorganism, there has been identified a calcium ion ($Ca^{2+}$)-independent transglutaminase derived from the genus *Streptoverticillium* (hereinafter referred to as "BTG"; Enzyme No. EC 2.3.2.13) (see Kanaji, et al., Journal of Biological Chemistry, 1993, Vol. 268, pp. 11565–11572 and U.S. Pat. No. 5,156,956).

In regard to those originating from fishes, cDNA's coding for the transglutaminases originating from *Pagrus major*, a *Theragra chalcogramma*, a flatfish(*Paralichthys olivaceus*) are isolated and the amino acid sequences thereof are elucidated (see YASUEDA, et al., Japanese Un-Examined Patent Publication (hereinafter referred to as "J.P. KOKAI") No. Hei.6-225775 and European Patent Publication No. EP-0555649A).

Moreover, there has recently been reported that the transglutaminase activity is also detected in a crude extract from the adductor muscle of a scallop (*Patinopecten yessoensis*) (MAMEKOSHI, et al., Collected Resume of Nippon Fisheries Association, Spring Meeting for the 5th fiscal year of Heisei, Lecture No. 715, p. 210). In this respect, however, the transglutaminase per se has not been isolated and therefore, various properties thereof have not yet been investigated.

The transglutaminase may be used for the production of, for instance, gel-like foods and gel-like cosmetics as well as yoghurt, jelly, boiled fish paste and cheese while making use of the ability of the enzyme to convert a protein into a high molecular weight product through crosslinking (ability thereof to gelate a protein) (Japanese Examined Patent Publication (hereinafter referred to as "J.P. KOKOKU") No. Hei 1-50382) and it may further be used in the preparation of thin films of proteins.

Moreover, the products prepared by a reaction which is catalyzed by the transglutaminase are stable to heat and therefore, the enzyme can be used in the production of, for instance, materials for microcapsules and carriers for immobilizing enzymes.

As the transglutaminase presently commercialized, there has been known BTG originating from a microorganism, but this enzyme does not require calcium ions for the onset of its enzyme activity. The enzyme is advantageous, due to the foregoing characteristic properties, in that it can be used under wide variety of reaction conditions, but suffers from a problem in that the control of the activity is conversely difficult when products to be produced requires delicate activity control.

Moreover, as the transglutaminases whose genes have been isolated and which have industrial applicability as recombinants, there have been known, for instance, those derived from *Cavia poreclus* and fishes. Both of these transglutaminases have characteristic properties common thereto such that they require calcium ions ($Ca^{2+}$) for the onset of their activity.

This permits the control of the activity of these transglutaminases by the addition of calcium ions to reaction systems and therefore, it would be expected that these transglutaminases can be used while making the most use of their characteristic properties.

However, if there is a transglutaminase whose enzyme activity can be controlled by means other than the addition of calcium ions, such an enzyme can be applied to various uses depending on factors such as the kinds of proteins as reagents, reaction conditions and the kinds of reaction products. It is presently assumed that the practical use of the transglutaminase which can be properly selected and used instead of BTG depending on purposes will hereafter increasingly be advanced and correspondingly, the demands for transglutaminases exhibiting diverse properties will certainly increase more and more..

Since the transglutaminase would mainly be applied to the preparation of foods, factors capable of controlling the transglutaminase activity other than calcium ions are desirably salts or ions which are originally present in foods. In particular, common salt is present in almost all foods, is a seasoning most familiar to the human being and in the "Shiozuri (minching with salt)" which is one of the steps for preparing fish jelly products, common salt is an element indispensable to the gelation of the boiled fish paste, i.e., the salting-in of proteins constituting the minced fish meat.

If a transglutaminase whose activity can be controlled by common salt is available and may be used, such a transglutaminase would have advantages listed below as compared with other transglutaminases. (1) When such a transglutaminase is applied to raw materials for foods whose gelation requires the use of a large amount of the conventional transglutaminase, the former may impart sufficient gel strength to the raw materials only in a small amount, due to the presence of common salt added to the materials during the previous process for the production thereof; and (2) the activity of the enzyme can further be improved through the addition of common salt rather than substances other than the ingredients for foods.

In respect of the physiological meaning of the transglutaminase, there have been proposed various opinions, but none of them have not yet been well-established. However, it would be believed that each transglutaminase takes part in a physiological function closely related to the ecology of the corresponding organism from which the transglutaminase is isolated, while taking into consideration the fact that various transglutaminases having different enzymological characteristic properties have been isolated from a variety of biological species.

For this reason, the inventors of this invention have searched marine animals in which common salt is an important element in their living environment and, in particular, those which are fit for food as targets for the transglutaminase whose activity can be controlled by common salt.

Moreover, even if an intended transglutaminase is found in a certain kind of marine animals which are fit for food, it would be believed that the extraction of the transglutaminase from the natural resource permits, with substantial difficulty, the mass-production of the transglutaminase for the purpose of putting it to practical use. For this reason, the genetic recombination technique is indispensable to the production of such a transglutaminase in order to put the enzyme in practical use.

Moreover, if a large amount of the intended transglutaminase can be obtained by the genetic recombination technique at a low price, this permits the reduction of the amount of minced fish meat in the processed products through simultaneous use of other cheap edible proteins and effective use of protein resources having low utilization in place of the same as measures to solve a problem concerning the deficiency of aquatic resources due to the 200 nautical mile-regulation and the overall fish catch-restrictions and accordingly, a problem concerning cost of raw materials for processed marine products.

DISCLOSURE OF THE INVENTION

Accordingly, it is an object of the present invention to obtain a transglutaminase from a marine animal which is fit for food, whose activity can be controlled by the addition of common salt.

Another object of the present invention is to provide a gene coding for the transglutaminase.

A further object of the present invention is to produce the intended transglutaminase by a genetic recombination technique.

A still another object of the present invention is to provide a method for gelating a protein through the use of the transglutaminase.

The foregoing and other objects of the present invention will become more apparent from the following description.

The inventors of this invention have conducted various investigations while taking various kinds of marine animals which are fit for foods as samples to accomplish the foregoing objects, have found out that the *Crassostrea gigas* includes a transglutaminase whose activity can be increased by the action of sodium chloride (hereunder also referred to as "NaCl"), potassium chloride (hereunder also referred to as "KCl") and thus have succeeded in the isolation and purification thereof. The onset of the enzyme activity thereof has calcium ion (hereinafter also referred to as "$Ca^{2+}$")-dependency, but the activity can be improved by the addition of NaCl and/or KCl in a certain concentration to the reaction system as has been discussed above. As a result, the inventors have found out that, if making the most use of the characteristic properties, a protein solution can be converted into a low viscosity solution, a high viscosity solution or a gelated product by appropriately adjusting the concentrations of NaCl and/or KCl or calcium ion concentration in the reaction solution and that this technique may be quite useful in food processing. To make sure, there has not been reported any transglutaminase having such characteristic properties.

Moreover, the inventors have obtained a gene coding for the transglutaminase originating from *Crassostrea gigas* and also succeeded in the determination of the base sequence thereof on the basis of the information obtained through partial amino acid sequence analysis of the transglutaminase of *Crassostrea gigas*. Thus, the gene can be expressed by the genetic engineering using microorganisms such as *Escherichia coli*, yeast and mold on the basis of these results and the transglutaminase originating from *Crassostrea gigas* having novel and industrially useful enzymological properties, i.e., the transglutaminase whose activity can delicately be controlled has been able to efficiently be produced at a low price and in a large amount. Moreover, the recombinant type transglutaminase exhibits the same characteristic properties as those observed for the transglutaminase originating from natural *Crassostrea gigas*. Therefore, the term "transglutaminase originating from *Crassostrea gigas*" used herein includes both the purified transglutaminase originating from natural *Crassostrea gigas* and the recombinant type transglutaminase derived from *Crassostrea gigas* unless otherwise specified.

As has been discussed above, the inventors of this invention have completed the present invention by completely solving the foregoing problems.

According to the present invention, there are provided the following inventions 1) to 8).

1) A transglutaminase originating from *Crassostrea gigas* exhibiting the following characteristic properties:
   a) Substrate Specificity: the enzyme catalyzes an acyl group transfer reaction between primary amines and γ-carboxyamide groups of glutamine residues present in a protein or a polypeptide chain;
   b) Molecular Weight: about 83,000 to 95,000 Da (as determined by SDS-PAGE);
   c) Optimum Reaction Temperature: 30° to 50° C.;
   d) Optimum Reaction pH: about 7.5 to 9.5;
   e) Activating Agent: The enzyme is activated by calcium ions and the activity can further be improved by the addition of either sodium chloride or potassium chloride;
   f) inhibiting Agent: The activity of the enzyme is inhibited by N-ethylmaleimide, momoiodo acetic acid or p-chloromercuribenzoic acid; and
   g) influence of Metal Ions: The activity of the enzyme is inhibited by $Cu^{2+}$.

2) A gene coding for the transglutaminase originating from *Crassostrea gigas*.

3) A plasmid carrying the gene.

4) A transformant transformed by the plasmid.

5) A method for producing a transglutaminase originated from *Crassostrea gigas* comprising the steps of cultivating the transformant in a culture medium to produce the transglutaminase originated from *Crassostrea gigas* and then isolating the transglutaminase originated from *Crassostrea gigas*.

6) The transglutaminase originated from *Crassostrea gigas* produced by the foregoing genetic recombination technique.

7) A composition comprising the transglutaminase originated from *Crassostrea gigas*.

8) A method for gelating a protein comprising the step of reacting the transglutaminase originated from *Crassostrea gigas* or the composition comprising the transglutaminase originated from *Crassostrea gigas* with a protein solution or slurry having a concentration of not less than 0.1% by weight to thus convert the solution or slurry into a gel.

BRIEF DESCRIPTION OF DRAWINGS

In FIG. 1, ○-○ represents absorbance at 280 nm, ●-● represents a TGase activity curve and the dotted line represents an NaCl concentration curve.

In FIG. 1, ○-○ represents absorbance at 280 nm, ●-● represents a TGase activity curve and the dotted line represents an $(NH_4)_2SO_4$ concentration curve.

In FIG. 3, ○-○ represents absorbance at 280 nm and ●-● represents a TGase activity curve.

In FIG. 4, ○-○ represents absorbance at 280 nm, ●-● represents a TGase activity curve and the dotted line represents an NaCl concentration curve.

In FIG. 7, ○-○ represents the results obtained using a sodium acetate buffer; △-△ represents the results obtained using an imidazole buffer; and □-□ represents the results obtained using a Tris buffer.

In FIG. 11, □-□ represents the results obtained using the TGase originating from the liver of *Cavia porcellus* and △-△ represents the results obtained using the TGase originating from a microorganism.

In FIG. 12, ○-○ represents the results obtained in the absence of NaCl and ●-● represents the results obtained in the presence of 0.5M NaCl.

FIG. 13 shows the amino acid sequence of the fusion protein of β-galactosidase and the TGase of *Crassostrea gigas* which is expressed by a plasmid pCGTG4E.

BEST MODE FOR CARRYING OUT THE INVENTION

Figure 1:
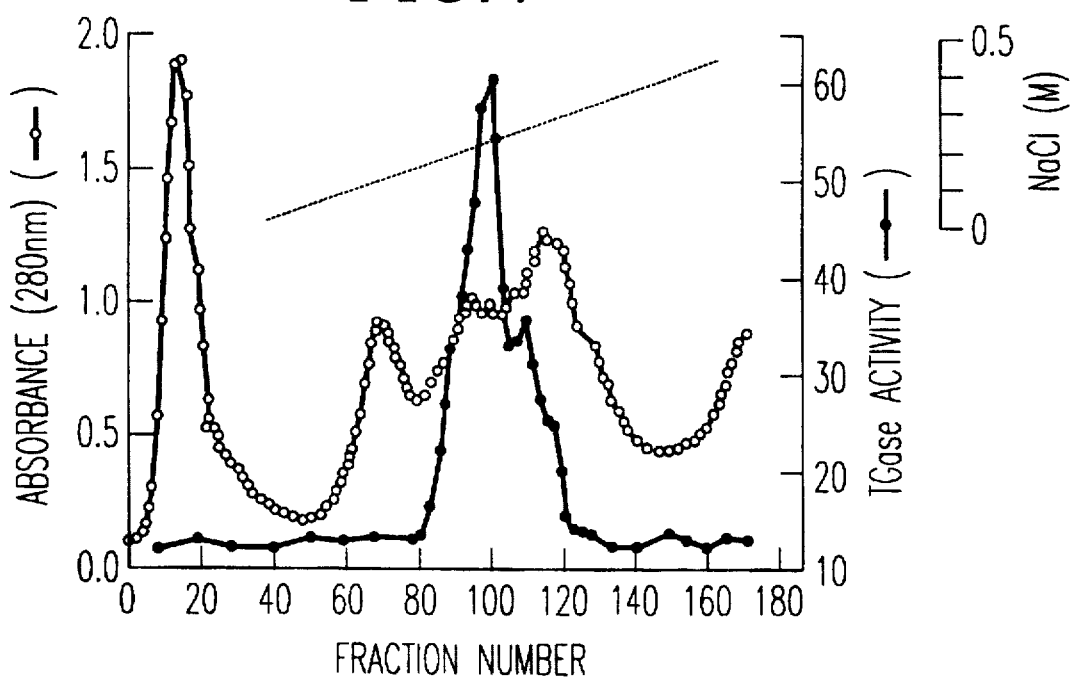
FIG. 1 is a diagram showing the results of purification of the transglutaminase originated from *Crassostrea gigas* (hereinafter referred to as "TGase of *Crassostrea gigas*" or "TGase") using a DEAE-Sephacel column.

The transglutaminases having the foregoing characteristic proeprties 1)-a) to 1)-g) are preferably those each having the amino acid sequence defined in the Sequence Listing as SEQ ID NO: 141 or 142 in the molecule. Moreover, examples of the amine listed in a) include methylamine, ethylamine, lysine and derivatives of lysine.

Incidentally, *Crassostrea gigas* has long been a very familiar food, in particular, it has long been eaten without cooking in not only Japan, but also Europe and America in where people do not have the habit of eating raw fishes and shellfishes. This fact clearly indicates that the transglutaminase originating from *Crassostrea gigas* would globally be acceptable as a transglutaminase having the highest safety. If applying the transglutaminase originated from *Crassostrea gigas* to the food industry, it may be (1) the transglutminase per se isolated from natural *Crassostrea gigas* and then purified; (2) a composition comprising the transglutaminase originating from *Crassostrea gigas* which is not highly purified; (3) a recombinant type transglutaminase prepared according to a genetic recombination technique; and (4) a composition obtained by incorporating, into the recombinant type transglutaminase, an excipient such as mannitol and sucrose and/or a seasoning such as sodium glutamate, 5'-inosinic acid and 5'-guanylic acid in an appropriate amount.

In fact, when applying the transglutaminase originating from *Crassostrea gigas* according to the present invention in the food industries, the possibility of using the recombinant type transglutaminase originating from *Crassostrea gigas* rather than the natural type one would be high. This is because, *Crassostrea gigas* is relatively expensive and accordingly, the extraction of the TGase of *Crassostrea gigas* from the narural resources suffers from problems of (1) high cost and (2) low mass-productivity.

The enzymes originating from organisms which are used for foods, even the genetic recombinant type ones such as the genetic recombinant type chymosin may be used as enzymes for preparing foods and therefore, the TGase of *Crassostrea gigas* obtained by the genetic recombination technique would not suffer from a problem of safety like chymosin. The present invention will hereinafter be described in more detail.

The novel TGase of *Crassostrea gigas* according to the present invention is present in the supernatant (crude extract) obtained by homogenizing *Crassostrea gigas* and then centrifuging the resulting homogenate. The purification of the transglutaminase from the crude extract can be performed using any means commonly used in this field such as dialysis, ultrafiltration, gel filtration and ion-exchange chromatography. The crude extract or purified product of the transglutaminase thus prepared are stable and can be stored over a long period of time at room temperature, preferably under a refrigerated condition or may be stored in the form of a powdery product obtained after drying under reduced pressure or freeze-drying.

The activity of the transglutaminase is determined by reacting the enzyme with dimethylated casein and monodansylcadaverine as substrates and measuring an increase in the fluorescent intensity of casein due to the incorporation of monodansylcadaverine into the dimethylated casein. The composition of the reaction solution is as follows:

| (Composition of Reaction Solution) | |
|---|---|
| dimethylated casein | 1.0 mg/ml |
| monodansylcadaverine | 0.015 mM |
| dithiothreitol | 3.0 mM |
| Tris-HCl buffer (pH 8.5) | 50 mM |
| calcium chloride | 10 mM |

In this respect, the same composition is used in Examples as will be detailed below unless otherwise specified.

To 2.4 ml of the foregoing reaction solution, there is added 20 to 50 μl of the transglutaminase solution followed by carrying out the reaction at 37° C. for 30 min, terminating the reaction by addition of 100 μl of a 500 mM EDTA solution and then determining the fluorescent intensity of the reaction solution (using a device: RF-1500 available from Shimadzu Corporation; excitation wavelength: 350 nm; wavelength of emitted fluorescent rays: 480 nm). In respect of the unit of the activity, that required for increasing the fluorescent intensity by 1.0 within one minute is herein defined to be one unit.

The method for gelating a protein using the transglutaminase originated from *Crassostrea gigas* will hereunder be detailed. First, proteins usable in the present invention are those which have lysine and glutamine residues required for the enzyme reaction and which are susceptible to the enzyme action, irrespective of the origin and quality thereof. Therefore, any protein such as animal proteins and vegetable proteins may be used in the present invention. Specific examples thereof are soybean protein, milk protein, fish meat protein.

The transglutaminase may be added to a solution or slurry of these proteins having a concentration of not less than 0.1% by weight, preferably not less than 5.0% by weight and more preferably 5.0 to 30% by weight to give a high viscosity or gelated product thereof.

The transglutaminase originating from *Crassostrea gigas* to be added may be a crude extract from natural *Crassostrea gigas*, a partially purified product of the enzyme, the transglutaminase isolated from the extract or a recombinant type one. When the transglutaminase is isolated, the enzyme may be used as such or in the form of a composition comprising an excipient such as mannitol and/or a seasoning such as sodium glutamate in proper amounts in addition to the isolated transglutaminase.

The amount of the transglutaminase originating from *Crassostrea gigas* to be added to such a solution or slurry is not restricted to a specific range. However, it is in general sufficient to add the transglutaminase originating from *Crassostrea gigas* in an amount ranging from about 0.01 to 200 units, preferably 0.1 to 20 units per 1 mg of a protein.

Moreover, the pH of the reaction solution is adjusted to about 5 to 10 and preferably 8 to 9. In addition, the reaction solution or slurry is incubated along with the enzyme at a temperature in general ranging from about 10° to 60° C., preferably 20° to 40° C. for 10 minutes to 24 hours, preferably 30 minutes to 6 hours to give such a high viscosity or gelated product thereof.

Then the method for controlling physical properties of the resulting gelated product of the protein while making use of the novel characteristic properties of the transglutaminase will be discussed below in detail. A protein or a protein-containing substance can be gelated through the use of the transglutaminase of the present invention, but the protein or a protein-containing substance may be converted into a high viscosity product or a gelated product by appropriately adjusting the salt concentration or calcium ion concentration in the reaction solution when preparing the gelated product of the protein.

The amount of calcium ions to be added or the amount of NaCl or KCl is not restricted to a specific range, but the amount of the salt or calcium ions is preferably controlled in the following manner.

In case where the reaction system (substrate) is free of calcium ions as well as NaCl and/or KCl:

① If only calcium ions are added, the amount of calcium ions to be added is in general adjusted to the range of from about 50 mM to 2M, preferably about 100 mM to 1M with respect to the reaction system (substrate).

② If a combination of calcium ions with NaCl and/or KCl is added to the reaction system (substrate), for instance, if NaCl is added to the reaction system in an amount of 0.3M, the amount of calcium ions to be added is in general adjusted to the range of from about 10 mM to 2M, preferably about 25 mM to 1M. Alternatively, if calcium ions are added to the reaction system in an amount of 50 mM, the amount of NaCl to be added is in general controlled to the range of from about 0 to 2M, preferably 100 mM to 1M.

If the reaction system (substrate) already comprises calcium ions as well as NaCl and/or KCl, they may be added to the reaction system while taking into consideration the contents of these ions and salts in the system. For instance, calcium ions may be added to the reaction system in an overall amount (i.e., the amount including that of the ions already present in the system) in general ranging from about 10 mM to 2M, preferably 50 mM to 1M. On the other hand, NaCl and/or KCl may be added to the system in an overall amount (i.e., the amount including those of the salts already present in the system) in general ranges from about 300 mM to 2M, preferably 500 mM to 1M.

The inventors of this invention have conducted intensive studies to perform cloning of a gene coding for the transglutaminase originating from *Crassostrea gigas* of the present invention. As a result, an intended cDNA could be obtained by a method which comprised chemically synthesizing single-stranded DNA's (corresponding to SEQ ID NO: 5–132 listed in the Sequence Listing attached hereto) on the basis of the base sequences estimated from partial amino acid sequences of the transglutaminase ultimately isolated from *Crassostrea gigas* and purified; carrying out PCR using the cDNA library, as a template, prepared using the mRNA extracted from *Crassostrea gigas* to amplify the DNA fragments; and then isolating the intended cDNA's from the cDNA library through hybridization using the amplified DNA fragments as probes.

In this connection, the inventors have also investigated, as candidate probes, a partial cDNA fragment (SEQ ID NO: 133 listed in the Sequence Listing) of the transglutaminase originated from a red sea bream (*Pagrus major*); a partial cDNA fragment (SEQ ID NO: 134 listed in the Sequence Listing) of the transglutaminase originating from a *Cavia porcellus*; a synthetic DNA fragment (SEQ ID NO: 135 listed in the Sequence Listing) present in the vicinity of the active center of the transglutaminase originating from a *Cavia porcellus*, in addition to the foregoing cDNA fragments. However, the inventors have failed in the isolation of an intended cDNA fragment originating from *Crassostrea gigas*. This would indicate that the intended cDNA cannot be obtained by the method based on the information concerning the known transglutaminases.

The inventors of this invention have succeeded in the cloning of the intended cDNA's of the transglutaminase originating from *Crassostrea gigas* by the foregoing method, but the cloning can likewise be carried out by the method detailed below:

1) The method comprises the steps of isolating the transglutaminase originating from *Crassostrea gigas*, then purifying the same, determining the amino acid sequence thereof and chemically synthesizing the whole base sequence thereof on the basis of the amino acid sequence thus determined;
2) In the cloning, the genomic library may be used instead of the cDNA library and the PCR technique may be used in place of the hybridization;
3) mRNA is supplied to the in vitro translation system of the wheat germ or the rabbit's veticulocyte to detect the fraction which comprises the mRNA coding for a polypeptide having the transglutaminase activity, producing the intended cDNA fragments using the fraction and then recovering the fragments.
4) An anti-transglutaminase (originating from *Crassostrea gigas*) antibody is prepared, followed by loading the cDNA library on a protein-expression vector, infection of an appropriate host cell with the vector to thus express the protein encoded by the cDNA and screening the intended cDNA using the foregoing antibody.

The "gene coding for the transglutaminase originating from *Crassostrea gigas*" herein includes all the genes which can provide products having the transglutaminase activity upon expression thereof, but preferred are a gene comprising the DNA coding for a protein having an amino acid sequence listed in the Sequence Listing as Sequence NO. 1 or 3 given below or a gene having a base sequence disclosed in the Sequence Listing as SEQ ID NO: 2 or 4.

In this respect, the gene coding for a protein having the amino acid sequence listed in the Sequence Listing as SEQ ID No: 1 or 3 includes those having various kinds of base sequences while taking into consideration the degeneracy of codon. More specifically, the intended gene can be selected from those having a variety of base sequences while taking into consideration various factors of the gene-expression system such as the preferential codon depending on, for instance, the kinds of host cells selected and inhibition of any higher-order structure formed by the transcribed RNA. The selected base sequence may be DNAs cloned from natural resources or those chemically synthesized.

The gene which is practically obtained through cloning in this invention has a base sequence listed in the Sequence Listing as SEQ ID NO: 2 or 4. These base sequences indicate that there are at least two kinds of N-terminals of the transglutaminase. In other words, the N-terminals start from the following sequences: Met-Ala-Phe- (see SEQ ID NO: 1, 2 in the Sequence Listing) and Ala-Phe- (see SEQ ID NO: 3, 4 in the Sequence Listing). Polypeptides having the transglutaminase activity are of course expressed by the use of either of these base sequences.

Saying over again, the gene coding for the transglutaminase originated from *Crassostrea gigas* of the present invention includes any gene so far as it can express polypeptides having the activity of the transglutaminase originating from *Crassostrea gigas*.

For instance, the gene coding for the transglutaminase originating from *Crassostrea gigas* include those having base sequences listed in the Sequence Listing as SEQ ID NO: 2 and 4, which include substitution, deficiency, insertion, addition or inversion of one or a plurality of bases. Moreover, such substitution, deficiency, insertion or the like of bases include those caused by spontaneous mutation due to individual differences, multiple replication of a gene, difference in organs and/or tissues and those induced by artificial mutations using, for instance, a technique for site-specified mutagenesis.

Moreover, the gene coding for the transglutaminase originating from *Crassostrea gigas* further includes genes hybridized with (1) a gene coding for a polypeptide comprising the amino acid sequence: SEQ ID NO: 1 or 3 listed in the Sequence Listing or (2) a gene having the base sequence: SEQ ID NO: 2 or 4 listed in the Sequence Listing so far as they can provide proteins having the activity of the transglutaminase originating from *Crassostrea gigas* upon expression.

The recombinant type transglutaminase originating from *Crassostrea gigas* can be obtained by expressing the transglutaminase originating from *Crassostrea gigas* in a microorganism modified by the genetic recombination technique. The present invention also relates to a plasmid carrying a gene coding for the transglutaminase originating from *Crassostrea gigas*.

The recombinant plasmid used can be produced by inserting a DNA including a gene coding for the transglutaminase originating from *Crassostrea gigas* into a known expression vector selected depending on a desired expression system according to the conventionally known method. Examples of expression vectors for *Escherichia coli* are T7gene10, an expression vector-carrying plasmid which can express a fusion protein with a linker peptide in high efficiency (Xpress System™, available from Inhydrogen Company) and an expression plasmid which can express a fusion protein with glutathione-S-transferase in high efficiency (pGEK Type Plasmid, available from Pharmacia Company).

On the other hand, examples of expression vectors for Baker's yeast include pYES2 (available from INVITROGEN Company) in which the promoter of GAL1 (a gene coding for galactokinase) can be used for the expression of foreign genes. The foregoing are only a few of the examples and other expression vectors may of course be used.

Then various transformants which are transformed with a transglutaminase gene-bearing expression vector will be detailed below.

Organisms usable in the present invention for forming transformants include prokaryotes such as *Escherichia coli* and *Bacillus subtilis*; and eucaryotes such as yeast and mold. Among these, preferred are *Escherichia coli* and yeast belonging to genus *Saccharomyces*, with *Escherichia coli* JM109 strain and *Saccharomyces cerevisiae* INVSC2 strain being more preferred. These transformants are cultivated in an appropriate culture medium to intracellularly produce the transglutaminase originated from *Crassostrea gigas* as an expressed product of the transglutaminase gene or to extracellularly produce the enzyme and accumulate it in the medium.

In this respect, the transformation is carried out according to the method currently used, for instance, the calcium chloride technique and the lithium chloride technique. Other methods may of course be used in the present invention.

Finally, a method for preparing the recombinant type transglutaminase by cultivating the foregoing transformant in a culture medium will be explained below in detail.

The conditions for cultivation may properly be determined by those skilled in the art while taking into consideration the kinds of transformants selected. Moreover, the transglutaminase expressed and secreted within the cell or accumulated in the culture medium may be isolated and purified by a variety of conventionally known methods. The genetic recombinant type transglutaminase may likewise be purified by the same method used for purifying the transglutaminase extracted from natural *Crassostrea gigas*.

Presently, it has not yet been reported that the transglutaminase originating from natural *Crassostrea gigas* comprises added saccharide chains and any saccharide chain is not added to the genetic recombinant type transglutaminase produced using *Escherichia coli* as a host cell, while if yeast is used as a host cell, the resulting transglutaminase may comprise added saccharide chains due to the glycosylation function present in the cell. However, it is assumed that the presence or absence of saccharide chains do not exert any influence on the transglutaminase activity and therefore, all of these recombinant type transglutaminases are included in the transglutaminase originating from *Crassostrea gigas* according to the present invention.

The recombinant type transglutaminase prepared by the method of the present invention exhibits the same properties and activity as those of the enzyme originating from natural *Crassostrea gigas*.

The present invention will hereinafter be described in more detail with reference to the following Examples, but the present invention is not restricted to these specific Examples.

EXAMPLE 1

Purification of Transglutaminase Originating from *Crassostrea gigas*

To 56 g of *Crassostrea gigas*, there was added a 20 mM MOPS buffer (pH 7.0) containing 10 mM NaCl, 5 mM EDTA and 1 mM dithiothreitol followed by crushing *Crassostrea gigas* to pieces in a homogenizer while cooling with carbon dioxide gas. The liquid comprising crushed *Crassostrea gigas* was centrifuged at 4° C., 3,000 rpm for 20 minutes (using Himac CR 20B2, rotor RPR20-2, available from Hitachi, Ltd.). Then the resulting supernatant was further centrifuged at 4° C., 37,000 rpm, for one hour (using 70P-72, rotor RP-70T, available from Hitachi, Ltd.), followed by passing the resulting supernatant through a filter of 0.45 μm (GL Chromatodisk, available from GL Science Company) to give 290 ml of a crude extract.

Then solid ammonium sulfate was added to the crude extract in such an amount that the rate thereof was 80% with respect to the extract, followed by allowing to stand with stirring for 3 hours to thus salt out proteins. Thereafter, the precipitates recovered by centrifugation of the extract at 3,000 rpm for 30 minutes was dialyzed against a 20 mM MOPS buffer (pH 7.0) containing 10 mM NaCl, 5 mM EDTA and 1 mM dithiothreitol followed by passing the resulting dialyzate through a column packed with DEAE-Sephacel (φ 2.6×16 cm, available from Pharmacia Company) which had been equilibrated, in advance, with the same solution.

As a result, the transglutaminase was adsorbed on the DEAE-Sephacel. The proteins were eluted by the NaCl concentration-grandient elution technique. The elution of the transglutaminase started at an NaCl concentration of about 0.15M (FIG. 1) and 156 ml of the fraction exhibiting the tansglutaminase activity was recovered.

Then solid ammonium sulfate was added to the resulting active fraction in such an amount that the final concentration thereof was 15% with respect to the fraction and then the solution was passed through a column packed with Phenyl-Sepharose (φ 1.6×10 cm, available from Pharmacia Company) which had been equilibrated, in advance, with a 20 mM MOPS buffer (pH 7.0) containing 15% ammonium sulfate, 10 mM NaCl, 5 mM EDTA and 1 mM dithiothreitol. As a result, the transglutaminase was adsorbed on the column.

Figure 2:
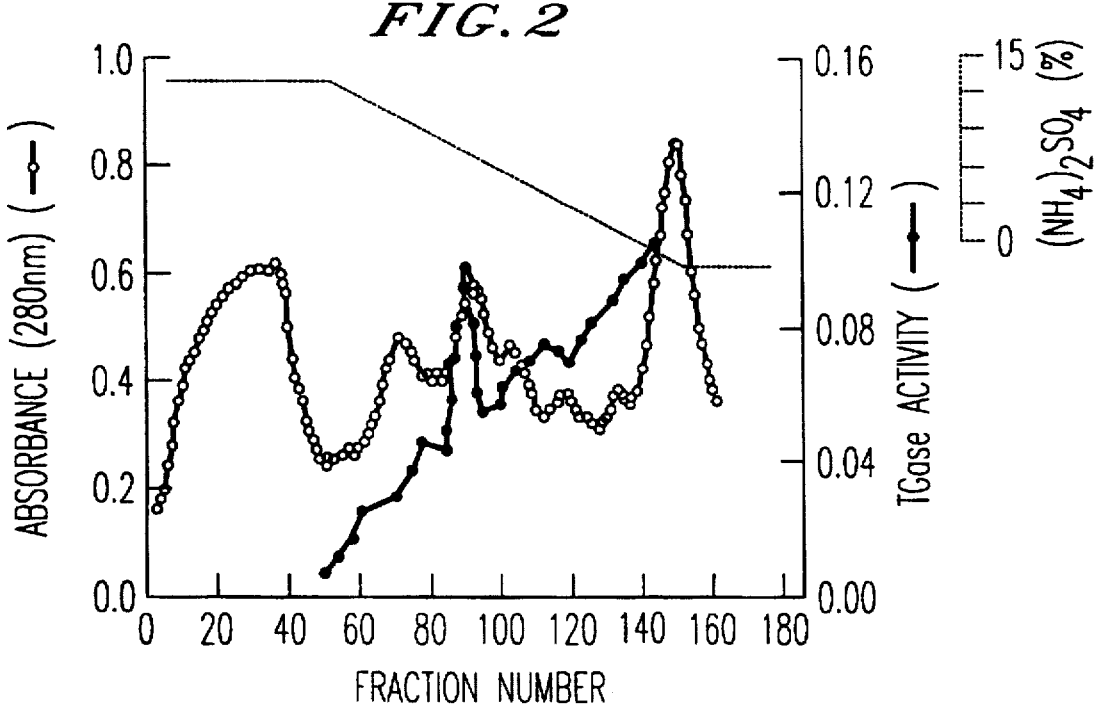
FIG. 2 is a diagram showing the results of purification of the TGase of *Crassostrea gigas* using a Phenyl-Sepharose column.

Thereafter, the protein was eluted by the ammonium concentration-gradient elution technique (descending concentration gradient) and it was found that the transglutaminase was eluted at an ammonium sulfate concentration of about 9% (FIG. 2) and 130 ml of the fraction exhibiting the tansglutaminase activity was recovered.

Figure 3:
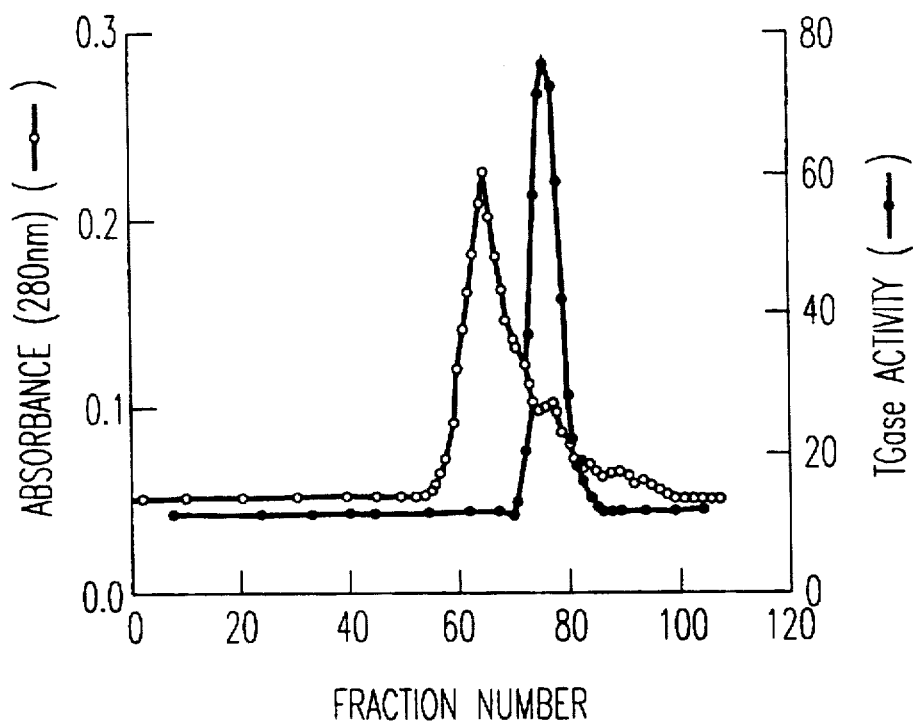
FIG. 3 is a diagram showing the results of purification of the TGase of *Crassostrea gigas* using a Sephacryl S-200 column.

Then the active fraction was concentrated using Polyethylene Glycol 20,000 and subjected to gel filtration using a column packed with Sephacryl S-200 (φ 2.6×60 cm, available from Pharmacia Company) which had been equilibrated, in advance, with a 10 mM Bis-Tris buffer (pH 6.25) containing 2 mM NaCl, 1 mM EDTA and 0.2 mM dithiothreitol. The protein was eluted using the same buffer as an eluant, it was found that the transglutaminase was eluted at a Kav of about 0.31 (FIG. 3) and 26 ml of the fraction exhibiting the tansglutaminase activity was recovered.

Figure 4:
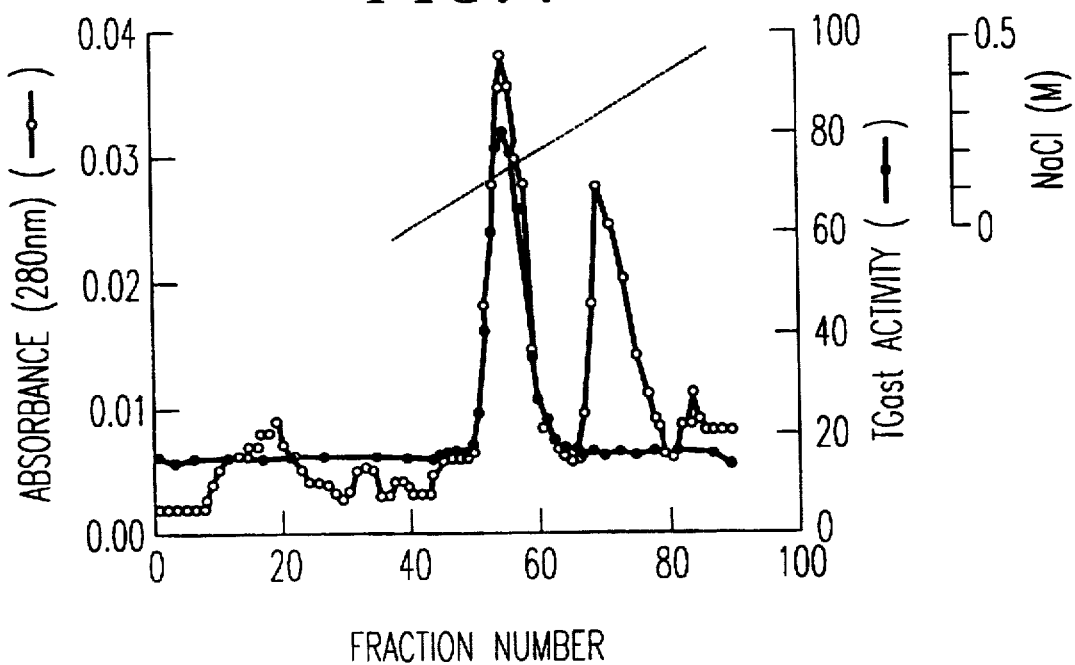
FIG. 4 is a diagram showing the results of purification of the TGase of *Crassostrea gigas* using a Mono-Q column.

Moreover, the resulting active fraction was passed through a column packed with Mono-Q (φ 0.5×5 cm, available from Pharmacia Company) which had been equilibrated, in advance, with a 10 mM Bis-Tris buffer (pH 6.25) containing 2 mM NaCl, 1 mM EDTA and 0.2 mM dithiothreitol. As a result, the transglutaminase originated from *Crassostrea gigas* was adsorbed on the column. The proteins were eluted by the NaCl concentration-grandient elution technique. The intended transglutaminase was eluted at an NaCl concentration of about 0.24M (FIG. 4) and about 3.4 ml of the fraction exhibiting the tansglutaminase activity was recovered.

The protein concentration of the active fraction was found to be about 77 μg/ml. Moreover, the total activity thereof was 358 units and the specific activity thereof was found to be 1404 units/mg protein.

The electrophoresis of the fraction revealed that only the protein exhibiting a single band of the molecular weight extending from about 84,000 to 94,000 was present in the fraction. Thus, the purified transglutaminase originating from *Crassostrea gigas* was obtained. The specific activity of the resulting purified solution was about 250 times that of the crude extract and the yield thereof was found to be about 7%. The results of the purification are summarized in the following Table 1.

TABLE 1

| Step | Total Protein (mg) | Total Activity (unit) | Specific Activity (unit/mg) | Yield (%) |
| --- | --- | --- | --- | --- |
| Crude Extract | 902 | 5141 | 5.70 | 100 |
| (NH₄)₂SO₄ Fraction | 903 | 4433 | 4.91 | 86 |
| DEAE-Sephacell | 132 | 4212 | 32.0 | 82 |
| Phenyl-Sepharose | 27 | 1567 | 57.6 | 31 |
| Sephacryl S-200 | 1.0 | 688 | 661.2 | 13 |
| Mono-Q | 0.26 | 368 | 1404 | 7 |

Then characteristic properties of the resulting purified transglutaminase were investigated.

a) Electrophoresis

A sample for electrophoresis was prepared by taking 30 μl of the purified transglutaminase, adding the same volume of a 0.125M Tris-HCl buffer (pH 6.8) containing 10% mercaptoethanol, 4% SDS, 20% glycerin and 0.002% Bromophenol Blue thereto and heating the mixture in a boiling water bath for one minute. The sample for electrophoresis (40 μl) was applied to a ready-made 5–20% polyacrylamide gel (available from Ato Co., Ltd.) and then electrophoretically fractioned at 20 mA for about 70 minutes using a 0.025M Tris-glycine buffer containing 0.1% SDS.

Figure 5:
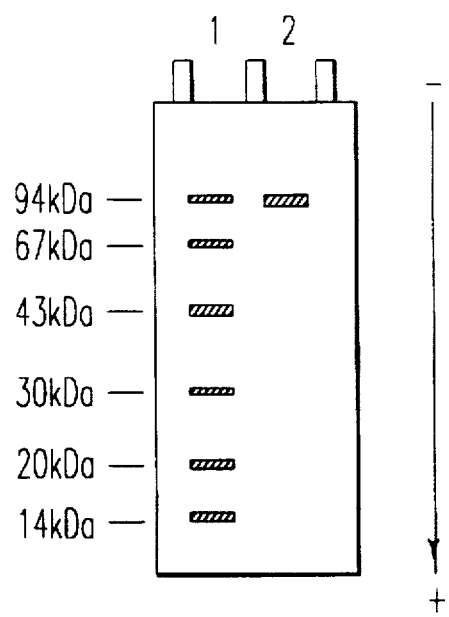
FIG. 5 is a diagram showing the results obtained by subjecting the TGase of *Crassostrea gigas* to SDS-polyacrylamide gel electrophoresis (SDS-PAGE).

After the completion of the electrophoresis, the gel was stained with a 0.12% Coomassie Brilliant Blue solution containing 50% methanol and 7% acetic acid overnight and then decolorized with a 7% acetic acid solution containing 50% methanol. As a result, a single electrophoresis band was found at a molecular weight roughly ranging from 83,000 to 95,000, more correctly about 84,000 to 94,000 (FIG. 5).

b) Optimum Reaction Temperature

Figure 6:
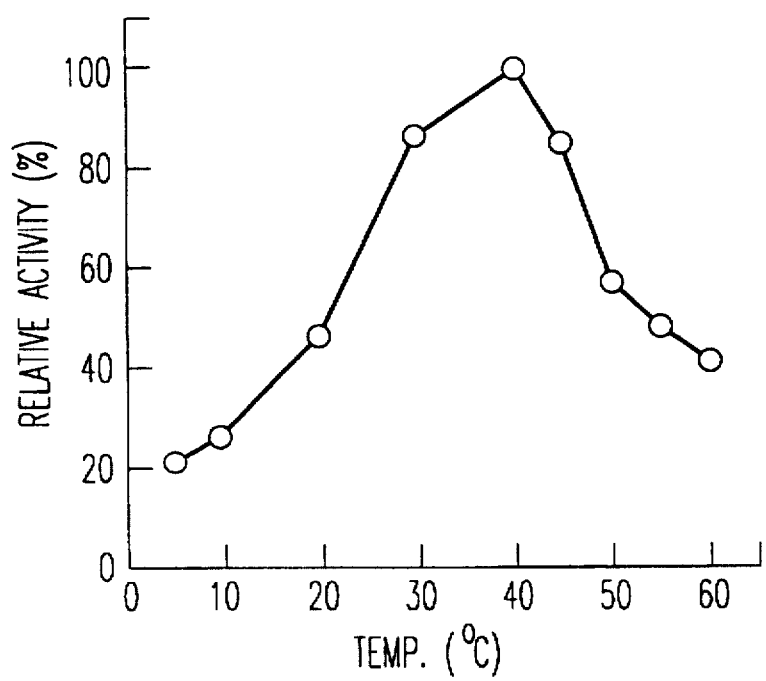
FIG. 6 is a diagram showing the optimum reaction temperature of the TGase of *Crassostrea gigas*.
Figure 7:
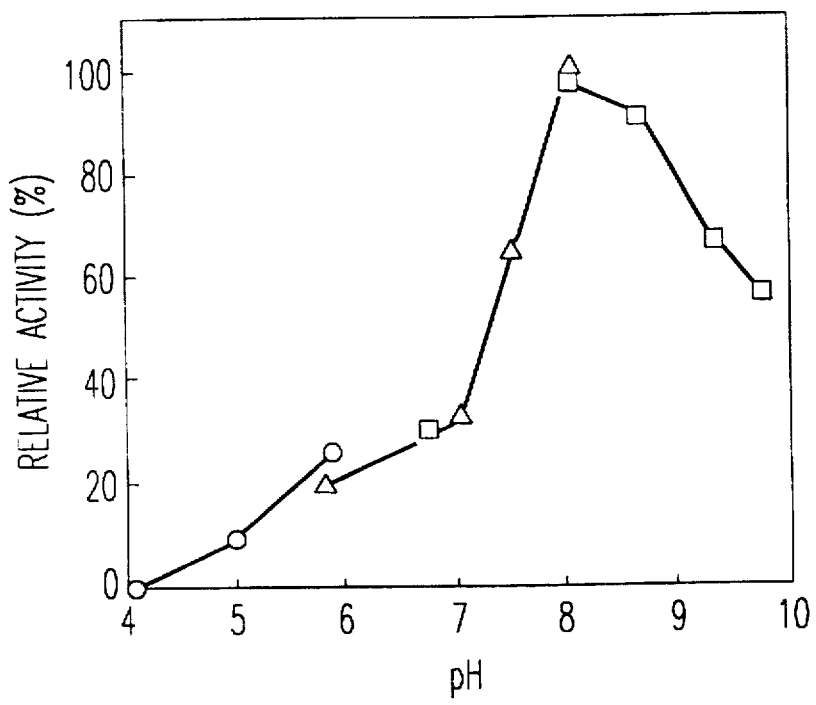
FIG. 7 is a diagram showing the optimum reaction pH of the TGase of *Crassostrea gigas*.

When dimethylated casein and monodansylcadaverine were used as substrates, the optimum reaction temperature ranged from 30° to 50° C. and more preferred optimum reaction temperature ranged from about 35° to 45° C., under the reaction conditions of a pH of 8.5 and a reaction time of 30 minutes (FIG. 6).

c) Optimum Reaction pH

When dimethylated casein and monodansylcadaverine were used as substrates, the optimum reaction pH ranged from about 7.5 to 9.5 and more preferred optimum reaction pH ranged from about 8 to 9, under the reaction conditions of a temperature of 37° C. and a reaction time of 30 minutes (FIG. 6).

d) Stability to Temperature

Figure 8:
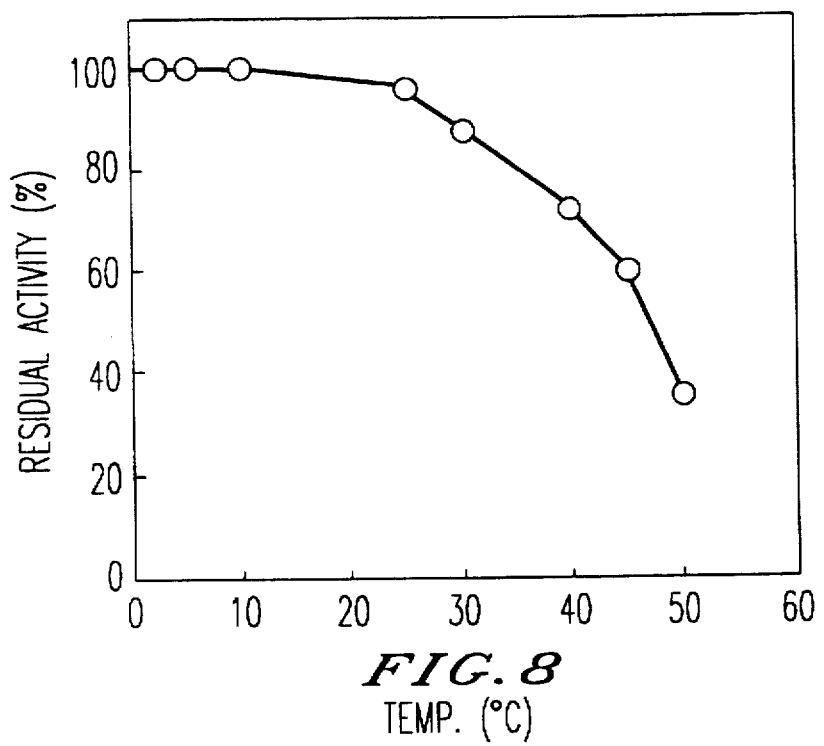
FIG. 8 is a diagram showing the temperature-stability of the TGase of *Crassostrea gigas*.

The purified transglutaminase was treated at a pH of 6.25 and at a temperature ranging from 2° to 50° C. for 10 minutes and then the reaction was carried out at a temperature of 37° C. for 30 minutes using dimethylated casein and monodansylcadaverine as substrates. As a result, it was found that the transglutaminase was stable at a temperature ranging from 2° to 25° C. (FIG. 8).

e) Stability to pH

Figure 9:
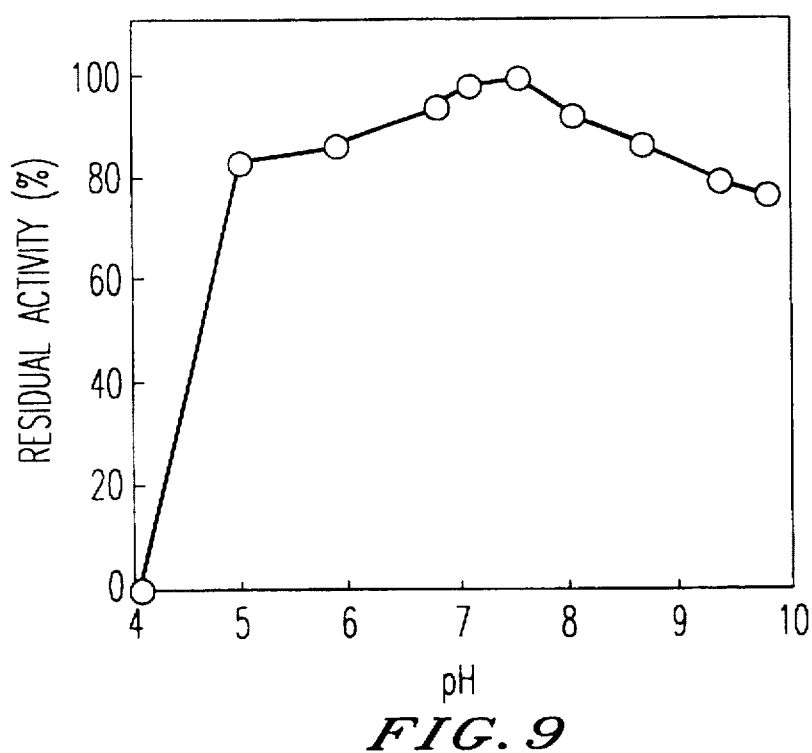
FIG. 9 is a diagram showing the pH-stability of the TGase of *Crassostrea gigas*.

The purified transglutaminase was treated at a temperature of 25° C. and at a pH ranging from 4 to 9.8 for 30 minutes and then the reaction was carried out at a temperature of 37° C. for 30 minutes using dimethylated casein and monodansylcadaverine as substrates. As a result, it was found that the transglutaminase was stable at a pH ranging from 5 to 9, more strictly 6 to 8.5 (FIG. 9).

f) Effect of Inhibiting Agents and Metal ions

The purified transglutaminase was treated at a temperature of 25° C. for 10 minutes while adding each of a variety of enzyme activity-inhibitory agents and each metal ion in such an amount that the final concentration thereof was equal to 1 mM and then the reaction was carried out at a temperature of 37° C. for 30 minutes using dimethylated casein and monodansylcadaverine as substrates. The results thus obtained are summarized in the following Table 2. Phenylmethylsulfone fluoride exhibited almost no enzyme activity-inhibitory effect, but monoiodoacetic acid, N-ethylmaleimide and p-chloromercuribenzoic acid showed high enzyme activity-inhibitory effect. In regard to metal ions, $Ba^{2+}$, $Mg^{2+}$ and $Sr^{2+}$ exhibited almost no enzyme activity-inhibitory effect, but $Co^{2+}$, $Pb^{2+}$ and $Cu^{2+}$ strongly inhibited the enzyme activity, with the inhibitory effect of $Cu^{2+}$ being extremely high.

TABLE 2

| Inhibitory Agent, Metal Ions | Residual Activity (%) |
| --- | --- |
| None | 100 |
| N-Ethylmaleimide | 11.8 |
| p-Chloromercuribenzoic Acid | 10.5 |

TABLE 2-continued

| Inhibitory Agent, Metal Ions | Residual Activity (%) |
| --- | --- |
| Monoiodoacetic Acid | 0 |
| Phenylmethylsulfone Fluoride | 96.4 |
| $Ba^{2+}$ | 102 |
| $Co^{2+}$ | 54.3 |
| $Mg^{2+}$ | 98.2 |
| $Mn^{2+}$ | 84.7 |
| $Ni^{2+}$ | 67.9 |
| $Pb^{2+}$ | 55.5 |
| $Sr^{2+}$ | 93.8 |
| $Zn^{2+}$ | 65.0 |
| $Cu^{2+}$ | 8.8 | g) Effect of NaCl and $Ca^{2+}$ on Enzyme Activity

Figure 10:
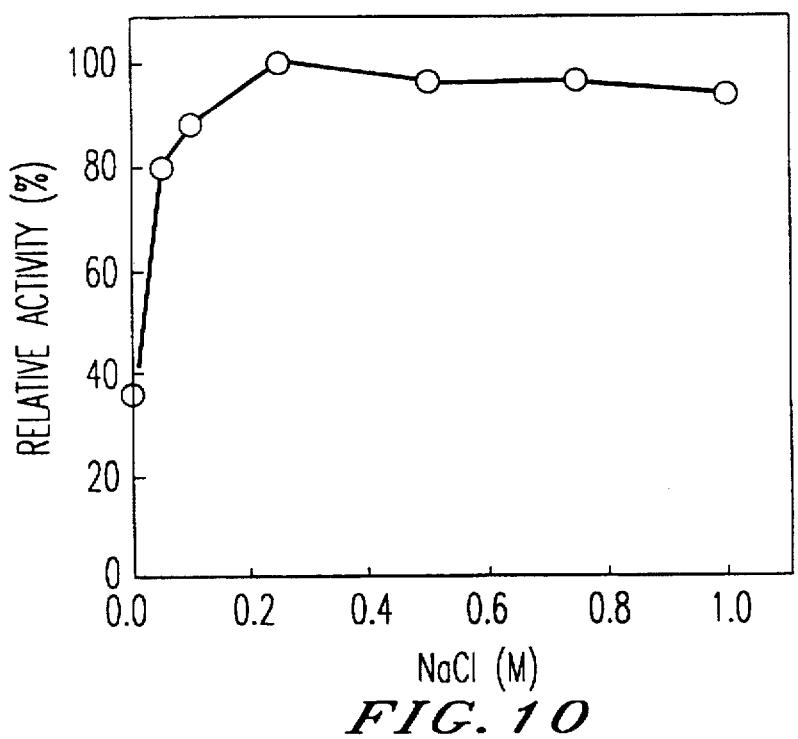
FIG. 10 is a diagram showing the effect of the NaCl concentration on the activity of the TGase of *Crassostrea gigas*.
Figure 11:
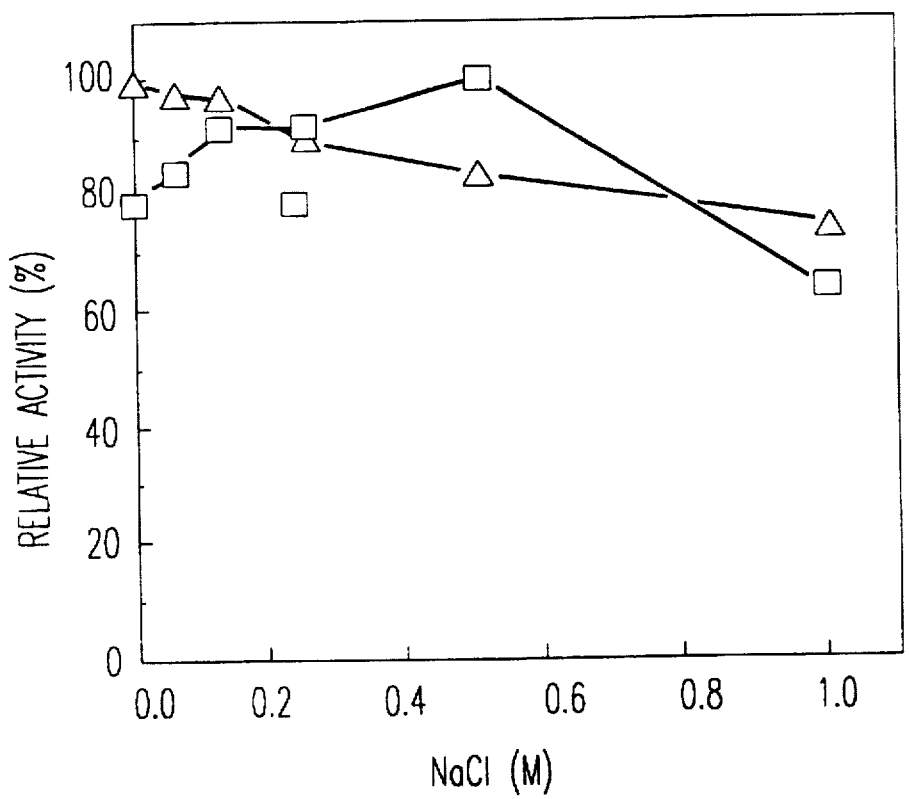
FIG. 11 is a diagram showing the effect of the NaCl concentration on the activity of the TGase originating from the liver of *Cavia porcellus* and the TGase originating from a microorganism.

When dimethylated casein and monodansylcadaverine were used as substrates, the enzyme activity increased as the NaCl concentration increased (FIG. 10). On the other hand, the activity of the transglutaminases originating from the liver of Cavia porcellus and a microorganism did not show any increase in response to an increase in the NaCl concentration (FIG. 11). This clearly indicates that the transglutaminase originating from Crassostrea gigas exhibits novel characteristic properties which have not been known.

Figure 12:
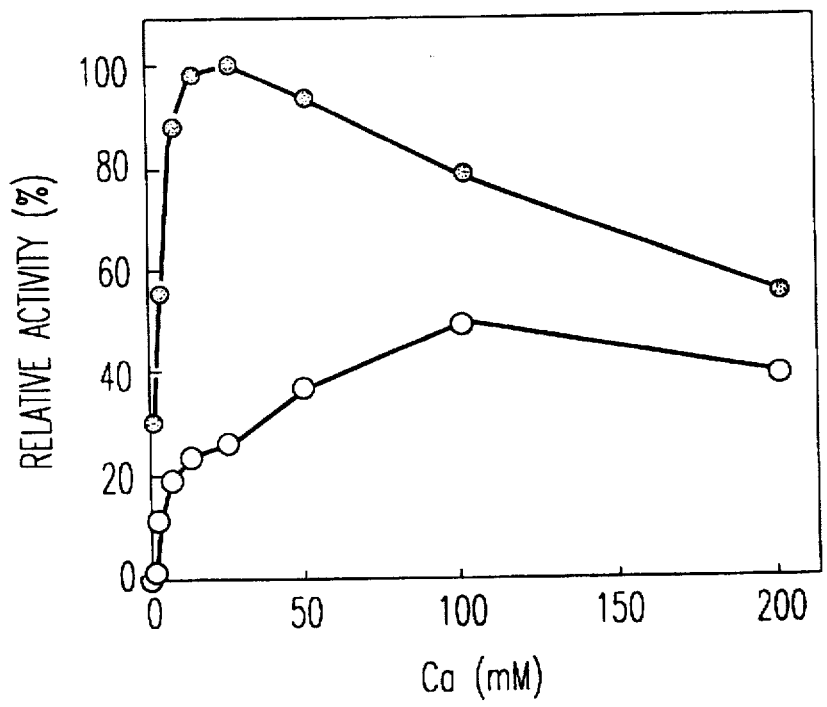
FIG. 12 is a diagram showing the effect of NaCl on the $Ca^{2+}$-dependency of the activity of the TGase of *Crassostrea gigas*.

Moreover, the enzyme activity of the transglutaminase showed a $Ca^{2+}$ concentration-dependency, but the activity reached the highest level at a $Ca^{2+}$ concentration of about 10 mM in the presence of NaCl and thereafter showed a tendency to be gradually reduced. On the other hand, the activity reached the highest level at a $Ca^{2+}$ concentration of about 100 mM in the absence of NaCl. In addition, the maximum activity observed in the presence of NaCl was found to be about 2 times that observed in the absence thereof (FIG. 12). The foregoing characteristic properties of the transglutaminase of the present invention are not likewise observed for the conventionally known transglutaminases.

It is believed that this specific behavior of the transglutaminase according to the present invention in response to NaCl and $Ca^{2+}$ has very high practical value in the food industries.

Moreover, the activity of the enzyme can likewise be improved by the addition of KCl.

h) Substrate Specificity

The inventors have investigated the enzyme activity of the purified transglutaminase using a variety of synthetic substrates and hydroxylamine.

The transglutaminase did not show any enzyme activity when benzyloxycarbonyl asparaginyl glycine, benzyloxycarbonyl glutamine and glycyl glutamyl glycine were used as the synthetic substrates.

However, the enzyme showed the enzyme activity when the synthetic substrate used was benzyloxycarbonyl glutaminyl glycine.

More specifically, the enzyme catalyzed the reaction when using CBZ-Gln-Gly, CBZ-Gln-Gly-OEt, CBZ-Gln-Gln-Gly and CBZ-Gly- Gly-Gln-Gly SEQ ID NO: 143 as the synthetic substrates, but did not catalyze the reaction when using CBZ-Gln, CBZ-Asn-Gly and Gly-Gln-Gly as the synthetic substrates.

In this respect, "CBZ" is the abbreviation for a benzyloxycarbonyl group, "Gln" is the abbreviation for a glutamyl group, "Gly" is the abbreviation for a glycyl group and "Asn" is the abbreviation for an asparaginyl group.

EXAMPLE 2

Gelation of Protein

Actomyosin was prepared from frozen minced fish meat of walleye pollacks according to the method of TAKASHI et al., Nippon Suisan Gakkaishi, 1970, 36(2), p. 169. More specifically, actomyosin was prepared by adding, to 25 g of the frozen minced fish meat of walleye pollacks, three volumes of a phosphate buffer (pH 7.5) containing 0.45M KCl to carry out extraction at 2° C. for 3 hours, followed by dilution and precipitation, dialysis against a 20 mM Tris-HCl buffer (pH 7.5) containing 0.3M NaCl and then centrifugation at 20,000 g for one hour to give a supernatant which was used as an actomyosin solution. The protein concentration thereof was found to be 0.4% by weight. Calcium chloride was added to the actomyosin solution in such an amount that the concentration thereof was 5 mM, then the crude extract of the transglutaminase (activity: 5.70 units per 1 mg of the protein) was added in an amount corresponding to 2.3 units per 1 mg of the protein, the mixture was sufficiently stirred and reacted at 37° C. for 90 minutes.

The gelation of the protein was evaluated by turning a test tube upside down. As a result, it was found that the actomyosin solution free of the transglutaminase still remained its solution state, but the solution to which the transglutaminase was added underwent gelation. Moreover, any gelation of the protein was not observed when the transglutaminase was added without addition of calcium ions.

EXAMPLE 3

Control of Gelation

To an aqueous solution of casein (available from Sigma Company) having a protein concentration of 1% by weight, there was added NaCl in such an amount that the concentration thereof was 0, 0.1 or 0.3M, while variously changing the calcium chloride concentration within the range of from 0 to 200 mM to thus investigate the gelation of the protein. In this connection, the purified transglutaminase was added in an amount corresponding to 4.0 units per 1 mg of the protein. After carrying out the reaction at 37° C. for 90 minutes, the degree of gelation was evaluated. The results thus obtained are summarized in the following Table 3. The results indicate that when the solution was free of NaCl, it underwent gelation at a $Ca^{2+}$ concentration of not less than 100 mM, while it underwent gelation at a $Ca^{2+}$ concentration ranging from 50 to 100 mM for the NaCl concentration of 0.1M. Moreover, when the NaCl concentration was 0.3M, the solution underwent gelation at a $Ca^{2+}$ concentration of not less than 25 mM.

TABLE 3

| NaCl (M) | CaCl$_2$ (mM) | | | | | |
|---|---|---|---|---|---|---|
|  | 0 | 10 | 25 | 50 | 100 | 200 |
| 0 | − | − | − | ± | + | + |
| 0.1 | − | − | ± | + | + | ± |
| 0.3 | − | ± | + | + | + | + |

In Table 3, "−" means that the solution was still in the solution state; "±" means that the solution was a high viscosity product; and "+" means that the solution was a gelated product.

The foregoing results indicate that the gelation of a protein can easily be controlled, i.e., a solution having a specific protein concentration can be converted into a solution, a high viscosity product or a gelated product by adjusting the concentration of calcium chloride or sodium chloride.

EXAMPLE 4

Identification of the Tissue Sites in *Crassostrea gigas* Having High Transglutaminase Activity

*Crassostrea gigas* from which the shells and the adductor muscles were removed were roughly divided into digestive reticular saccus, gills, mantle and other tissues. Each tissue was crushed in a solution comprising 10 mM NaCl, 5 mM EDTA, 1 mM DTT and 20 mM imidazole-HCl buffer (pH 7.5) followed by centrifugation of the resulting liquid at 18,000 rpm for 30 minutes and filtration of the resulting supernatant through a filter: GL Chromatodisk (available from GL Science Company) to give a crude extract.

Then the transglutaminase activity of the crude extract was investigated by an activity-detection method which made use of an increase in the intensity of fluorescent light (the fluorescent intensity observed at 480 nm while exciting with the light rays of 350 nm) due to the linkage of monodansylcadaverine to methylated casein as an indication. This activity-detection method is the method disclosed in Nippon Suisan Gakkaishi, 1991, 57, pp. 1203–1210 which is slightly modified. More specifically, 20 µl of each crude extract was added to 2 ml of a solution comprising 50 mM Tris-HCl buffer (pH 8.5), 1 mg/ml methylated casein, 15 µM monodansylcadaverine and 10 mM calcium chloride, followed by stirring and keeping warm at 37° C. for 20 minutes. After the reaction, 100 µl of 500 mM EDTA solution was added to the reaction system and each reaction solution was inspected for the intensity of emitted fluorescent light using a fluorophotometer (Shimadzu RF-1500, available from Shimadzu Corporation).

The increases in the fluorescent intensity per total amount of the protein present in the crude extract of each tissue are summarized in the following Table 4. The results listed in Table 4 indicate that the gill shows the highest transglutaminase activity. It has thus been clear from the foregoing fact that the highest expression of the transglutaminase in *Crassostrea gigas* is observed in the gill thereof.

TABLE 4

| Tissue | Increase in Fluorescent Intensity/Protein (mg) |
|---|---|
| Digestive reticular saccus | 0.79 |
| Gill | 10.00 |
| Mantle | 7.97 |
| Other Tissues | 2.64 |

EXAMPLE 5

Preparation of DNA Fragment Carrying Gene Coding for Transglutaminase Originating from *Crassostrea gigas*

While taking into consideration the results obtained in the foregoing Examples, a cDNA library will be prepared using mRNA extracted from the gill of *Crassostrea gigas* and the cDNA coding for the transglutaminase originating from *Crassostrea gigas* will be isolated from the library. The procedures used to isolate the gene will be detailed below.

The gill of Japanese oyster (11.3 g) was crushed in a solution (90 ml) containing 5M guanidine thiocyanate and 1% β-mercaptoethanol using a polytron and a homogenizer. Sodium laurylsulfate was added to the crushed cell liquid in such an amount that the final concentration thereof was 0.5%, then the solution was centrifuged at room temperature and 10,000 rpm for 20 minutes to give a supernatant. The supernatant was passed through an injector needle of 25 gauge over 20 times to cut the chromosomal DNA present in the solution into fragments. The solution was further centrifuged in the same manner used above and then subjected to CsCl density-gradient centrifugation according to the usual method to thus purify the whole RNA (see Sambrook et al., Molecular Cloning: a laboratory manual, Cold Spring Harbor Laboratory, Cold Spring Harbor Press (1989)). The amount of the resulting whole RNA was found to be 4.16 mg. The total amount thereof was treated with an mRNA purification kit (available from Clontech Company) which made use of Oligo-(dT) Cellulose Column to purify the mRNA molecules and to thus give 73.54 µg of mRNA.

The resulting mRNA (6.72 µg) was used as a template for producing the intended cDNA. This cDNA was produced according to the protocol of Time-Saver cDNA Synthesis Kit (available from Pharmacia Company) for synthesizing double-stranded cDNA's using a random primer. The resulting cDNA was incorporated into the restriction enzyme EcoRI-cleaved site of a λ-phage vector, λ ZapII (available from STRATAGENE Company) and then treated with Gigapack II Gold Packaging Kit (available from STRATAGENE Company) to thus produce and recover the cDNA library of *Crassostrea gigas* in the form incorporated into the phage protein.

In this respect, the titer of this cDNA library was found to be $1.2 \times 10^6$ pfu/µg vector.

A host cell, XLI-Blue was infected with the phage corresponding to $1.4 \times 10^5$ pfu of the foregoing cDNA library of *Crassostrea gigas*, then the infected cells were inoculated on 7 agar plates each having a diameter of 150 ml in an amount of $2.0 \times 10^4$ pfu per plate. The agar plates were cultivated at 37° C. for about 6.5 hours and the phage plaques formed on the plates were transferred to nylon membranes (Hybond-N available from Amersham Company).

Then the nylon membranes carrying the transferred phage plaques were treated with an alkali to denature the DNA, neutralized and then washed. Thereafter, the nylon membranes were treated at 80° C. for 2 hours to thus immobilize the DNA.

The resulting nylon membranes were pre-hybridized at 42° C. for 3 hours and then hybridized at 42° C. for 15 hours.

In this respect, the solution for the pre-hybridization comprises 6×SSC (1×SSC comprises 0.15M NaCl, 0.015M sodium citrate and has a pH of 7.0), 5×(SP)Denhardt's solution (1×(SP)Denhardt's solution comprises 0.02% BSA, 0.02% Ficol 1, 0.02% polyvinyl pyrrolidone), 20% formamide, 100 µg/ml chromosomal DNA of *Escherichia coli* and 0.1% SDS.

Moreover, the DNA probe used in the hybridization was a synthetic DNA fragment present in the vicinity of the active center of the transglutaminase of *Cavia porcellus* (Ikura et al., Biochemistry, 27, 2898–2905(1988): SEQ ID No. 135 in the Sequence Listing) which was labeled with [γ-$^{32}$P] ATP. However, any clone which would be positive could not be detected in this screening procedure.

Thus cDNAs of the known transglutaminases were used as the DNA probes for the hybridization. More specifically, the DNA probes practically used were the cDNA fragments present in the vicinity of the active centers of the transglutaminase of *Cavia porcellus* and *Pagrus major* respectively which were labeled with [α-$^{32}$P] dCTP (SEQ ID NO: 134 and 133 listed in the Sequence Listing).

However, any clone which would be positive could not also be detected in this screening procedures.

The foregoing results would indicate that the transglutaminase of *Crassostrea gigas* did not have high structural homology with the known transglutaminases and therefore, the inventors have abandoned the use of the screening method which is based on the sequence information for the known transglutaminases. For this reason, the transglutaminase originated from *Crassostrea gigas* was purified, followed by analysis of a partial amino acid sequence thereof and recovery of a partial cDNA fragment of the transglutaminase originating from *Crassostrea gigas* using the PCR technique on the basis of the resulting information about the amino acid sequence. The resulting cDNA fragment was used as the probe for the hybridization during the screening procedure.

EXAMPLE 6

Partial Amino Acid Sequence Analysis of Transglutaminase Originating from *Crassostrea gigas*

A solution containing about 20 µg of the purified transglutaminase was concentrated to dryness through centrifugal concentration, followed by addition of 1.0 ml of distilled water and stirring at 37° C. for 30 minutes to thus redissolve the purified transglutaminase therein. To the solution, there was added Lysyl Endopeptidase (available from Wako junyaku Co., Ltd.) and the reaction was carried out at 37° C. for 20 hours to thus cleave the enzyme into peptide fragments. In this respect, the reaction was terminated by the addition of trifluoroacetic acid (hereunder referred to as "TFA") in such an amount that the final concentration thereof in the reaction system was 0.1%.

Then the reaction solution was passed through a reverse phase HPLC column (vydac $C_{18}$ Reverse Phase HPLC Column; φ 4.6×250 mm, available from Cipress International Company) and eluted according to acetonitrile concentration-gradient elution (solvent: 0.1% TFA) to isolate and recover each peptide fragment.

The resulting peptide fragments each was inspected for the amino acid sequence using Protein Sequencer (PPSQ-10, available from Shimadzu Corporation) and as a result, the following five kinds of sequences were obtained (SEQ ID NO: 144–148):

Asn-His-His-Thr-Asn-Glu-Phe-Glu-Lys; Asp-Cys-Thr-Val-Pro-Trp-Lys; Trp-Thr-Gly-Ser-Val-Ala-Ile-Ile-Lys; Asp-Gly-Thr-Met-Glu-Val-Ser-Gln-Ile-Asp-His-Ser-Ala-Val-Gly; Tyr-Glu-Glu-Asn-Glu-Ser-Met-Ile-Ile-Leu-Phe-Asn.

EXAMPLE 7

Isolation of Partial cDNA Fragment for Screening cDNA of Transglutaminase Originated from *Crassostrea gigas*, by PCR Method on the Basis of Partial Amino Acid Sequence Information There were chemically synthesized single-stranded DNA's (the base sequences thereof are listed in the Sequence Listing as Sequence Nos. 5 to 133) which would code for the following partial amino acid sequences: His-His-Thr-Asn-Glu-Phe-Glu (SEQ ID NO: 141 in the Sequence Listing) and Tyr-Glu-Glu-Asn-Glu-Ser-Met (SEQ ID NO: 142 in the Sequence Listing) out of the partial amino acid sequences of the transglutaminase originating from *Crassostrea gigas* produced above and the PCR method was carried out using the cDNA library derived from *Crassostrea gigas* to thus obtain a DNA fragment comprising about 400 base pairs (hereinafter referred to as "bp"). The DNA fragment was purified and randomly labeled with [α-$^{32}$P] dCTP. The inventors could thus obtain candidate strains of the clone which was positive in the primary screening through the use of the labeled DNA fragment as the probe for the hybridization. Finally, a positive clone could be obtained through secondary screening.

The infected *Escherichia coli* cell carrying the foregoing positive clone was further infected with a helper phage (Exassist helper phage) (available from STRATAGENE Company) to thus incorporate the cDNA derived from the positive clone into a plasmid vector pBluescript SK⁻. The length of the insert cDNA of the positive clone was found to be about 3.5 bp. This clone is named pCGTG4.

The base sequence of the insert cDNA of pCGTG4 was analyzed by the conventionally known method which made use of Taq DyeDeoxy Terminator Cycle Sequencing Kit (available from Perkin-Elmer Company).

As a result, it was found that the insert cDNA had a base sequence having 3394 bp as listed in the Sequence Listing as SEQ ID NO: 136. The sequence included a part whose base sequence was in agreement with that of the DNA probe used herein. Moreover, the amino acid sequence translated from the base sequence is listed in the Sequence Listing as Sequence No. 136. The *Escherichia coli* cell carrying the plasmid pCGTG4 comprising the cDNA of the transglutaminase originating from *Crassostrea gigas*, i.e.,*Escherichia coli* SOLR/pCGTG4 (AJ 13048) is deposited with Kogyo Gijutsuin Seimei Kogaku Kogyo Gijutsu Kenkyusho of Agency of Industrial Science and Technology (hereunder referred to as "Seimeiken") under the accession number of FERM BP-4961 (in this regard, FERM BP-4961 was transferred from the national depositary (Seimeiken; the accession number: FERM P-14580).

EXAMPLE 8

Construction of Plasmid pCGTG4E capable of expressing Transglutaminase Gene of *Crassostrea gigas*, Introduction Thereof into *Escherichia coli* and Detection of transglutaminase Activity in transformed *Eschelichia coli*.

Subsequently, to examine whether the insert cDNA of the plasmid pCGTG4 thus obtained coded for the transglutaminase originating from *Crassostrea gigas* or not, the inventors tried to express the insert cDNA in *Escherichia coli* in the form of a fusion protein of the transglutaminase with β-galactosidase. More specifically, the inventors tried to incorporate the base sequence portion of the plasmid pCGTG4 which was assumed to be an open reading frame into the plasmid pUC19 which could undergo expression in *Escherichia coli* capable of expressing the fusion protein with β-galactosidase under the control of an lac promotor (FIG. 13).

Figure 14:
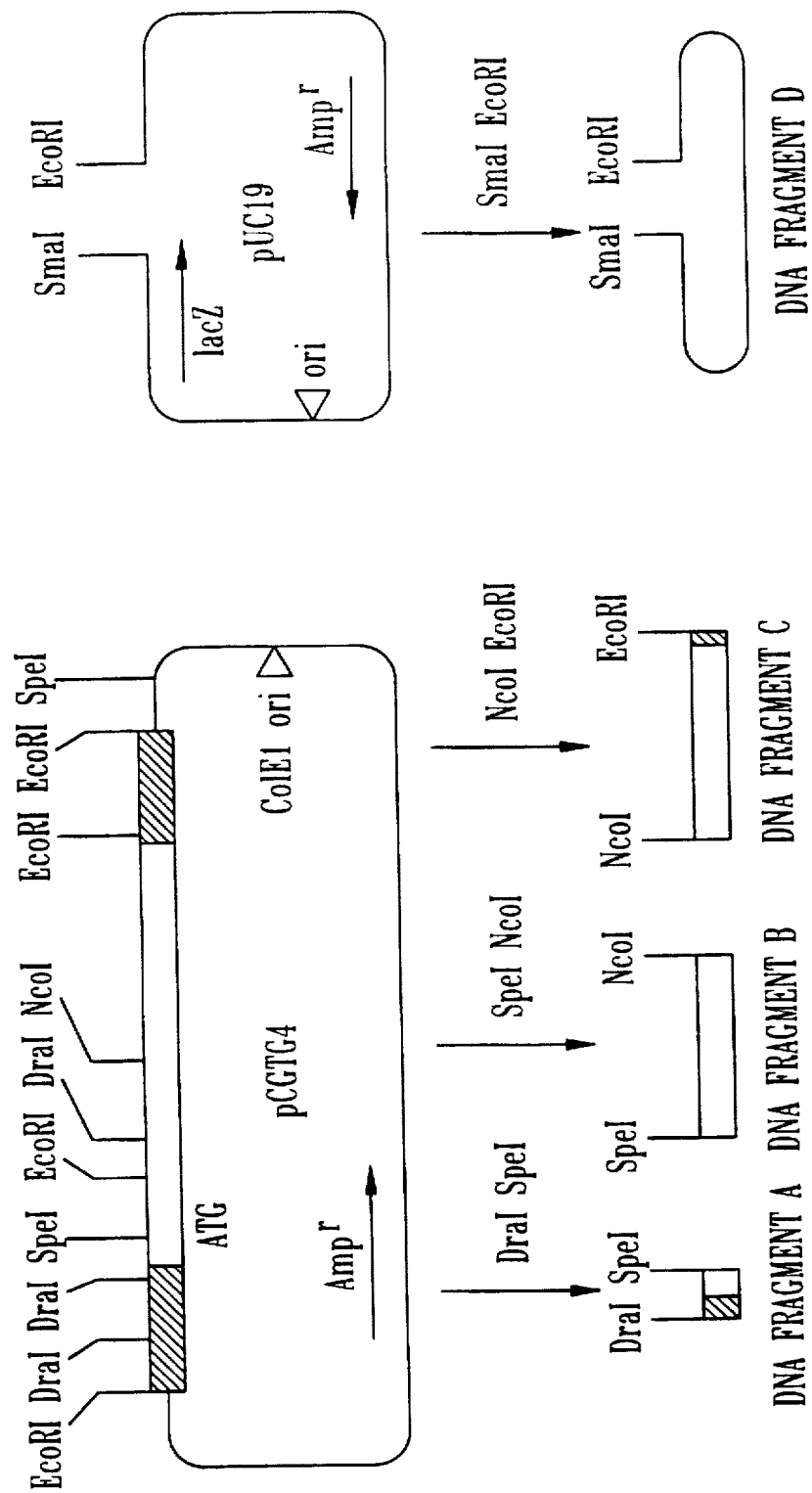
FIG. 14 is a diagram showing the outline of the method for constructing the plasmid pCGTG4E.
Figure 15:
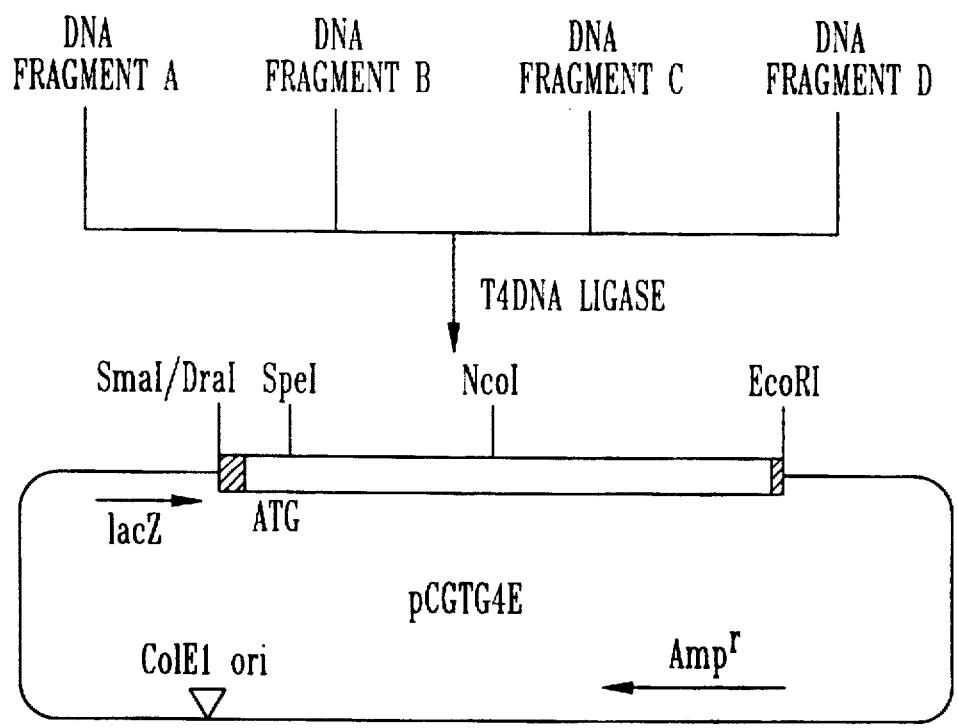
FIG. 15 is a diagram showing the outline of the method for constructing the plasmid pCGTG4E.

This plasmid is named pCGTG4E. The method for constructing the plasmid will be described below and shown in FIGS. 14 and 15. As shown in FIGS. 14 and 15, a plasmid, pCGTG4E, capable of expressing the cDNA of the transglutaminase originating from *Crassostrea gigas* was obtained by ligating, with T4DNA ligase, a DNA fragment A having about 200 bp and obtained by digesting pCGTG4 with restriction enzymes DraI and SpeI, a DNA fragment B having about 1600 bp and obtained by digesting pCGTG4 with restriction enzymes SpeI and NcoI, a DNA fragment C having about 700 bp and obtained by digesting pCGTG4 with restriction enzymes NcoI and EcoRI and a DNA fragment D having about 2700 bp and obtained by digesting the expression plasmid pUC19 (available from Takara Co., Ltd.) with restriction enzymes SmaI and EcoRI.

The pCGTG4E was incorporated into *Escherichia coli* JM109 to give a transformant *Escherichia coli* JM109/pCGTG4E (AJ 13049). In this respect, *Escherichia coli* AJ 13049 is deposited with Seimeiken under the accession number of FERM BP-4962 (in this regard, FERM BP-4962 was transferred from the national depositary (Seimeiken; the accession number: FERM P-14581)).

The colony of the transformant (FERM BP-4962) thus obtained was inoculated on 50 ml of LB culture medium (comprising 10 g/l of trypton, 5 g/l of yeast extract and 10 g/l of NaCl (pH 7.0)) supplemented with 50 mg/l of ampicillin and 10 mM of IPTG contained in a Sakaguchi flask, followed by cultivation at 26° C. for 21 hours and collection of the bacterial cells from the culture medium.

The collected bacterial cells were suspended in 0.9 ml of a crushed bacterial cell liquid (a solution comprising 20 mM Tris-HCl (pH 7.5), 30 mM NaCl, 5 mM EDTA; hereunder the composition thereof will be omitted), followed by addition of 0.1 ml of a 10 mM/ml lysozyme solution and allowing to stand on ice for 1.5 hour. Then the bacterial cell suspension was crushed by applying ultrasonics thereto and centrifuged (at 15,000 rpm for 2 minutes) to give a supernatant of the crushed bacterial cell liquid. Moreover, the same procedures were repeated to obtain a supernatant of a crushed bacterial cell liquid starting from *Escherichia coli* carrying only pUC19.

The foregoing supernatants were assayed for the transglutaminase activity by the method discussed above. The results thus obtained are summarized in the following Table 5. The results obtained using the TGase originated from *Cavia porcellus* (available from Takara Co., Ltd.) as a control are also listed in Table 5.

TABLE 5

| *Escherichia coli* | Increase in Fluorescent Intensity/Cultivation Temp. |
| --- | --- |
| pCGTG4E/JM109 AJ13049 | 12.8/26° C. |
| pUC19/JM109 | 0.0/26° C. |
| TGase of *Cavia porcellus* | 4.3/— |

(Control : 1.2 μg protein)

As a result, the data listed in Table 5 indicate that the bacterial cell extract of *Escherichia coli* which carries the expression plasmid comprising the cDNA of the *Crassostrea gigas* transglutaminase obtained in the foregoing Example shows the transglutaminase activity. It is thus clear that the cDNA isolated by the inventors codes for the transglutaminase.

EXAMPLE 9

Construction of Plasmid pCGTG4EP Expressing Pressumed Whole Amino Acid Sequence of Transglutaminase Originating from *Crassostrea gigas* and Introduction Thereof into *Escherichia coli*

Figure 16:
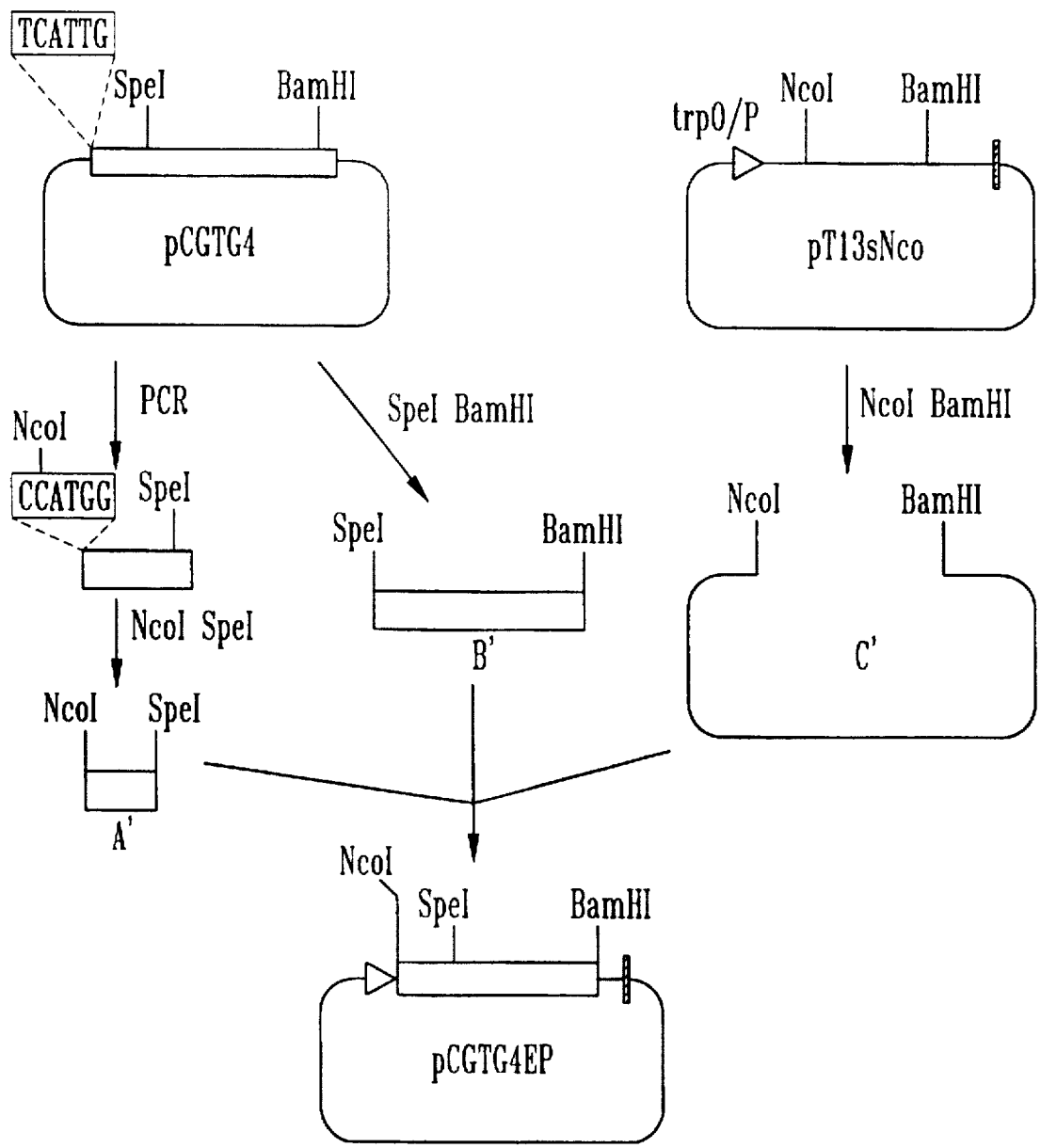
FIG. 16 is a diagram showing the outline of the method for constructing the plasmid pCGTG4EP.

Moreover, the inventors of this invention have constructed a plasmid pCGTG4EP which is designed such that only the whole amino acid sequence deduced from the cDNA sequence of the transglutaminase originating from *Crassostrea gigas* is expressed in *Escherichia coli* cells (see FIG. 16).

The plasmid pCGTG4EP was constructed as followes. To obtain a DNA fragment in which a restriction enzyme NcoI-recognizing sequence was incorporated by converting the base sequence 5'-TC ATG G-3' present near the translation initiation codon of the *Crassostrea gigas* transglutaminase cDNA (the initiation codon is underlined, Sequence No. 136 in the Sequence Listing) into 5'-CC ATG G-3', a DNA fragment was amplified by the PCR method using a mutation-introducing primer which was a single-stranded synthetic DNA produced on the basis of the insert base sequence of pCGTG4 (SEQ ID NO: 137 in the Sequence Listing) and a single-stranded synthetic DNA produced from the base sequence portion thereof far downstream side of the insert base sequence as a primer, the amplified DNA fragment was incorporated into the restriction enzyme HincII-recognizing and cleaving site of pUC18 and it was confirmed, by sequencing, that the intended DNA fragment was cloned. Thereafter, the plasmid pCGTG4 was digested with restriction enzymes NcoI and SpeI to give a DNA fragment A' coding for the portion near the N-terminal of the transglutaminase originating from *Crassostrea gigas*.

Moreover, pCGTG4 was digested with restriction enzymes SpeI and BamHI to give a DNA fragment B' and pT13sNco (Tonouchi N. et al., Journal of Biochemistry, 104, pp. 30–34 (1988)) was digested with restriction enzymes NcoI and BamHI to give a DNA fragment C'. These three DNA fragments were ligated with T4 DNA ligase by the usual method to construct a plasmid capable of expressing the TGase of *Crassostrea gigas* in *Escherichia coli*, i.e., pCGTG4EP. This expression plasmid has an ability of expressing the TGase of *Crassostrea gigas* in *Escherichia coli* under the control of a tryptophan promoter originated from pT13sNco. The outline of the method for constructing the same is shown in FIG. 16.

The pCGTG4EP was incorporated into *Escherichia coli* HB101 by a known method to form a transformant *Escherichia coli* pCGTG4EP/HB101.

The colony of the transformant harvested was inoculated on the 50 ml of M9 synthetic medium (comprising 12.8 g Na$_2$HPO$_4$, 3 g KH$_2$PO$_4$, 0.5 g NaCl, 1 g NH$_4$Cl, 0.4 g glucose, 2 mM MgSO$_4$, 1 μM CaCl$_2$, 50 mg proline and leucine, 2 g casamino acid/1 l) supplemented with 50 mg/ml of ampicillin contained in a Sakaguchi flask, followed by cultivation at 37° C. for 21 hours and collection of the bacterial cells.

The collected bacterial cells were suspended in 0.9 ml of a cell crushing solution (20 mM Tris-HCl (pH 7.5), 30 mM NaCl, 5 mM EDTA, hereunder the composition will be omitted), followed by addition of 0.1 ml of a 10 mg/ml lysozyme solution and allowing to stand on ice for 1.5 hour. Thereafter, the bacterial cell suspension was crushed by applying ultrasonics and then centrifuged (at 15,000 rpm for 2 minutes) to give a supenatant of the crushed bacterial cell solution. The same procedures were repeated to give a supenatant of the crushed bacterial cell solution starting from *Escherichia coli* carrying only the plasmid pUC18.

Each supernatant was assayed for the transglutaminase activity by the same method used in Example 7. As a result, it was found that the bacterial cell extract of *Escherichia coli* pCGTG4EP/HB101 carrying the expression plasmid comprising the cDNA of the transglutaminase originating from *Crassostrea gigas* showed the transglutaminase activity although the detected activity was very low.

This clearly indicates that the cDNA thus obtained is a gene coding for the transglutaminase and that the amino acid sequence deduced on the basis of this cDNA shows TGase activity.

EXAMPLE 10

Confirmation of N-Terminal Amino Acid Sequence of Recombinant Type Transglutaminase of *Crassostrea gigas* Expressed in *Escherichia coli*

Subsequently, the amino acid sequence of the N-terminal portion of the recombinant type transglutaminase of *Crassostrea gigas* expressed in pCGTG4EP/HB101 was subjected to sequencing procedures to thus identify the practical amino acid sequence of the N-terminal portion of the recombinant type transglutaminase of *Crassostrea gigas* expressed on the basis of the cDNA obtained in the invention.

*Escherichia coli* pCGTG4EP/HB101 was inoculated on 50 ml of M9 synthetic medium containing 50 mM of ampicillin, followed by shaking culture in a Sakaguchi flask at 28° C. for 12 hours, harvesting the bacterial cells and preparation of a crushed bacterial cell liquid by the same method used in Example 7. A part of the crushed cell liquid was subjected to SDS-PAGE to separate the recombinant type transglutaminase of *Crassostrea gigas* on the gel for electrophoresis and then transferred to a PVDF membrane (available from Millipore Company) through electroblotting. The portion of the transferred recombinant type transglutaminase of *Crassostrea gigas* on the PVDF membrane to which proteins had been transferred from the electrophoresis gel was cut out and supplied to a protein sequencer (PPSQ-10, available from Shimadzu Corporation). As a result, the amino acid sequence of the N-terminal was found to be, from the side of the N-terminal, Ala-Phe-Trp-Gly-Val-Phe-Tyr and Met-Ala-Phe-Trp-Gly-Val-Phe-Tyr (SEQ ID NO:149, 150). In other words, the recombinant type transglutaminase of *Crassostrea gigas* expressed in the bacterial cell of *Escherichia coli* comprised both an amino acid sequence corresponding to that estimated on the basis of the cDNA from which methionine as an initiation codon was removed and an amino acid sequence corresponding to that estimated based on the latter.

EXAMPLE 11

Construction of Plasmid pCGTG4S Capable of Expressing Gene Coding for Transglutaminase of *Crassostrea gigas* in Yeast, Introduction Thereof into *Saccharomyces cerevisiae* and Detecting transglutaminase Activity in transformed *Saccharomyces cerevisiae*

First, the foregoing plasmid pCGTG4E carrying the cDNA coding for the transglutaminase of *Crassostrea gigas* was digested with restriction enzymes PvuII, BamHI and BglI to give a DNA fragment carrying the cDNA of the transglutaminase of *Crassostrea gigas* and having about 2800 bp.

On the other hand, the plasmid capable of expressing in *Saccharomyces cerevisiae* used herein was pYES2 (available from INVITROGEN Company) which permitted the use of the promoter for GAL1 as the gene coding for galactokinase in the expression of foreign genes. The plasmid was digested with a restriction enzyme XhoI, then the cleaved terminal of the DNA was blunted with Klenow enzyme and digested with a restriction enzyme BamHI to give a DNA fragment having about 5800 bp.

Figure 17:
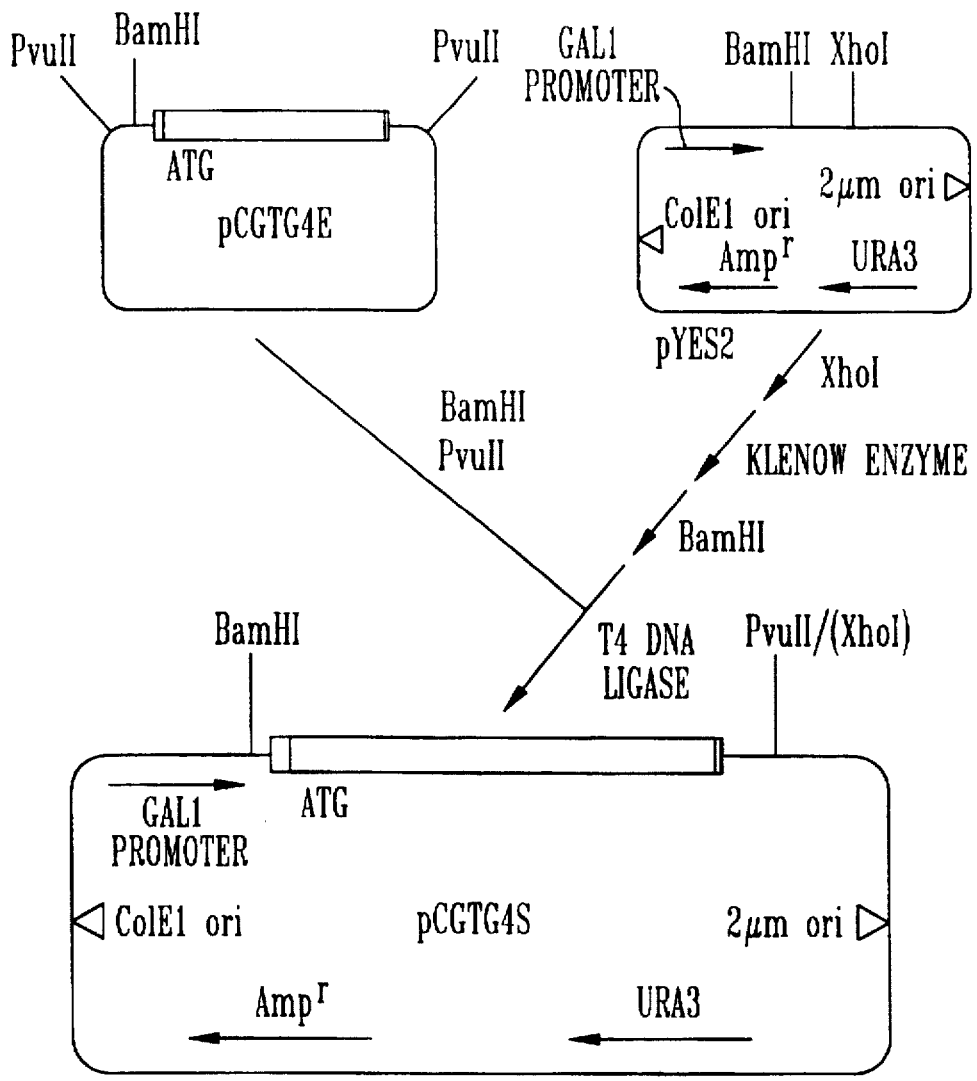
FIG. 17 is a diagram showing the outline of the method for constructing the plasmid pCGTG4S.

The foregoing two DNA fragments were subjected to a ligation using T4DNA ligase according to the usual method to give a plasmid pCGTG4S capable of expressing the transglutaminase of *Crassostrea gigas* in yeast cells (FIG. 17). The plasmid was incorporated into *Escherichia coli* HB101 by a known method to form a transformant *Escherichia coli* HB101/pCGTG4S AJ13050. In this respect, the *Escherichia coli* HB101/pCGTG4S AJ13050 is deposited with Seimeiken under the accession number of FERM BP-4963 (in this regard, FERM BP-4963 was transferred from the national depositary (Seimeiken; the accession number: FERM P-14582)).

A plasmid pCGTG4S was prepared from the transformant according to the alkali SDS method and then incorporated into *Saccharomyces cerevisiae* INVSC2 strain (MAT α, his3- Δ200, ura3-167) using Yeast-Transforming Kit for the alkali cation method (available from Bio101 Company). The selection of the transformant was performed using a glucose synthesis minimum medium plate (the synthesis minimum medium comprised 0.17% Yeast Nitrogen Base W/O Amino Acids and Ammonium Sulfate (available from Difco Company) and 0.5% ammonium sulfate and the plate was prepared by adding glucose in such an amount that the final concentration thereof was 2% to the medium and then solidifying in a 90 mm petri dish using a 2% agar) comprising 50 mg/ml of histidine, to thus give a transformant *Saccharomyces cerevisiae* INVSC2/pCGTG4S AJ14697. In this respect. The transformant *Saccharomyces cerevisiae* INVSC2/pCGTG4S AJ14697 is deposited with Seimeiken under the accession number of FERM BP-4964 (in this regard, FERM BP-4964 was transferred from the national depositary (Seimeiken; the accession number: FERM P-14583)).

The transformant was first inoculated on 50 ml of a glucose synthesis minimum medium (prepared by adding 2% glucose and 50 mg/ml of histidine to the foregoing synthesis minimum medium) contained in a Sakaguchi flask and cultivated at 30° C. for 24 hours by shaking culture to increase the number of the cells. Thereafter, the culture medium was centrifuged to collect the cells, then the cells were suspended in a Sakaguchi flask containing 50 ml of a galactose synthesis minimum medium (prepared by adding 2% galactose and 50 mg/ml of histidine to the foregoing synthesis minimum medium) and cultured at 30° C. for 24 hours by shaking culture to induce the transcription from the GAL1 promoter. The INVSC2 strain free of the plasmid was likewise cultivated using the foregoing glucose, galactose synthesis minimum medium to which 50 mg/ml of uracil was further added.

After the cultivation, the cells included in 30 ml of the culture medium was collected through centrifugation and suspended in 1 ml of the crushed cell liquid (used above). This cell suspension (1 ml) was introduced into a 1.5 ml Eppendorf tube, followed by addition of 0.5 ml volume glass beads (diameter: 0.5 mm) and vigorous stirring for 2 minutes to crush the cells. Then the suspension was centrifuged at 15000 rpm for 2 minutes and the resulting supernatant was used as a sample for measuring the transglutaminase activity.

Each supernatant obtained through the centrifugation after crushing the cells (0.35 ml) was inspected for the transglutaminase activity by the same method used in Example 8 (Table 6). As a result, it was found that the crushed cell extract of the transformed yeast (FERM BP-4964) comprising the *Crassostrea gigas* transglutaminase-expressing plasmid (pCGTG4S) whose transcription from the GAL1 promoter had been induced clearly showed the transglutaminase activity. This clearly indicate that the cDNA thus obtained can express the transglutaminase having high activity even in yeast.

TABLE 6

| Yeast | Increase in Fluorescent Intensity |
|---|---|
| INVSC2/pCGTG4S AJ14697 | 46.6 |
| INVSC2 | 0 |
| TGase of *Cavia porcellus* | 3.4 |

(control: 1.2 μg protein)

Moreover, the inventors of this invention have conducted the following experiments in order to examine whether the transglutaminase expressed by yeast exhibited the characteristic properties of the transglutaminase of *Crassostrea gigas* in the enzyme reaction or not.

The crushed cell extract of the foregoing *Saccharomyces cerevisiae* INVSC2/pCGTG4S AJ14697 (FERM BP-4964) was inspected for the transglutaminase activity while changing the NaCl concentration in the reaction solution by way of comparison (Table 7).

As a result, the crushed cell extract of the foregoing *Saccharomyces cerevisiae* INVSC2/pCGTG4S AJ14697 (FERM BP-4964) exhibited an increase in the transglutaminase activity at a high NaCl concentration like the transglutaminase originating from natural *Crassostrea gigas*. This indicates that the enzyme expressed by yeast behaves like that originating from natural *Crassostrea gigas*, i.e., the recombinant type transglutaminase possess characteristic properties similar to those observed for the transglutaminase extracted from natural *Crassostrea gigas*. Moreover, other characteristic properties of the recombinant type transglutaminase thus prepared such as substrate specificity, molecular weight, optimum temperature, stability to temperature, influence of an activating agent thereon and influence of an inhibitory agent thereon are the same as those observed for the transglutaminase originating from natural *Crassostrea gigas*.

In addition, the foregoing fact clearly indicates that the cDNA obtained herein is a DNA coding for the transglutaminase of *Crassostrea gigas*.

TABLE 7

| Reaction Conditions | Increase in Fluorescent Intensity |
|---|---|
| in the absence of NaCl | 17.7 |
| in the presence of 50 mM NaCl | 34.9 |
| in the presence of 500 mM NaCl | 69.1 |
| TGase of *Cavia porcellus* | 3.5 |

(control: 1.2 μg protein)

EXAMPLE 12

Confirmation of N-terminal Amino Acid Sequence of Recombinant Type Transglutaminase of *Crassostrea gigas* Expressed in Yeast Then the recombinant type transglutaminase of *Crassostrea gigas* expressed in yeast was subjected to sequencing procedures to determine the amino acid sequence of the N-terminal thereof and to thus identify the amino acid sequence of the practical N-terminal of the recombinant type transglutaminase of *Crassostrea gigas* expressed on the basis of the cDNA obtained herein.

Figure 18:
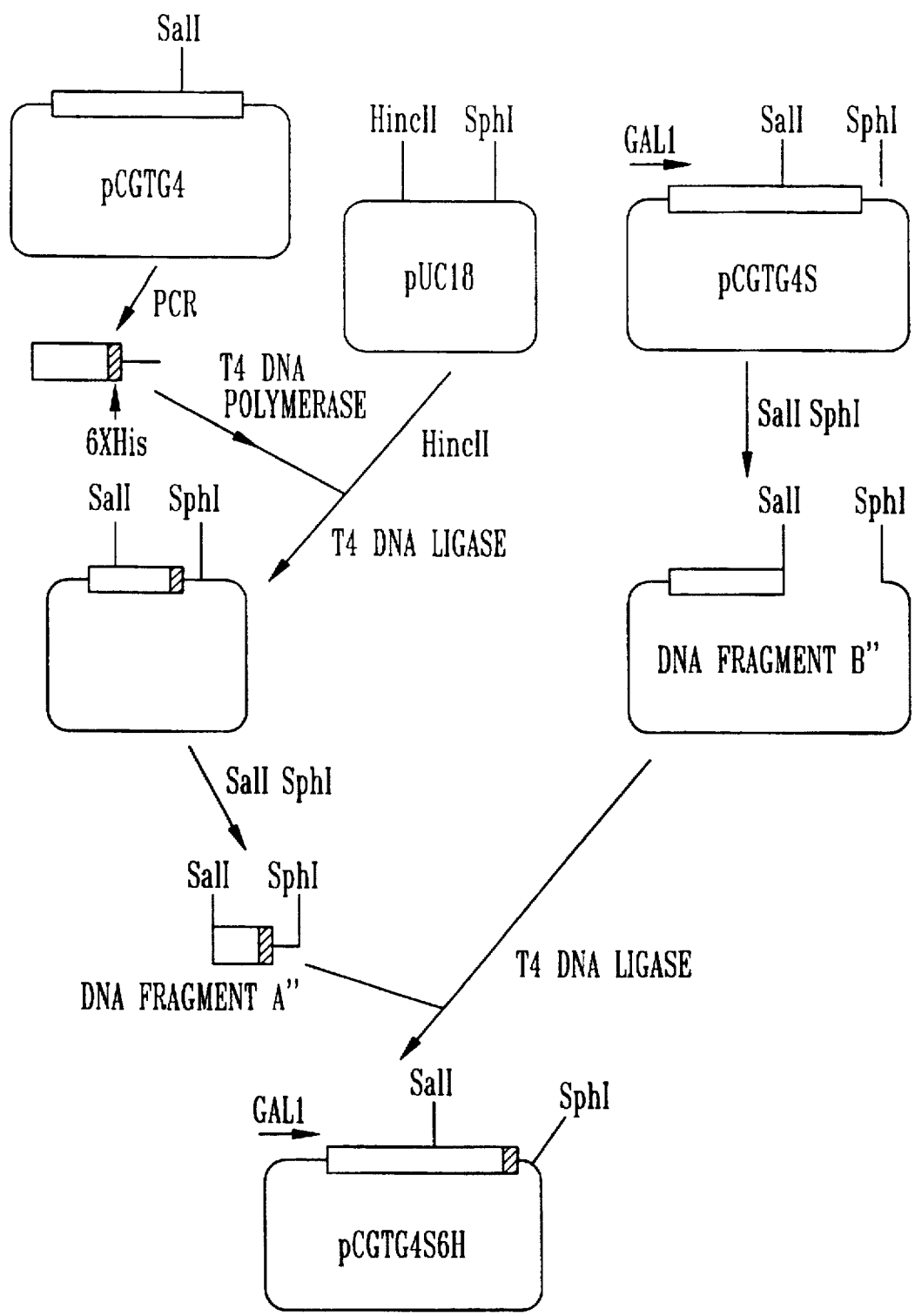
FIG. 18 is a diagram showing the outline of the method for constructing the plasmid pCGTG4S6H.

First of all, there was constructed a plasmid pCGTG4S6H capable of expressing the transglutaminase of *Crassostrea gigas* in which additional 6 histidine residues were added to the C-terminal (aspartic acid residue) of the open reading frame thereof in order to make the purification of a recombinant protein easy. The outline of the method is shown in FIG. 18.

First, PCR was carried out using a single-stranded synthetic DNA having a sequence described as Sequence No. 139, 140 in the Sequence Listing as primers and the foregoing plasmid pCGTG4 as a template, followed by incorporation of the amplified DNA fragment into the site of the plasmid pUC18 recognized and cleaved by a restriction enzyme HincII, confirmation of whether the intended DNA fragment was amplified or not through sequencing and digestion thereof with restriction enzymes SalI and SphI to give a DNA fragment A".

Moreover, the plasmid pCGTG4S was digested with restriction enzymes SalI and SphI to give a DNA fragment B". These two DNA fragments were ligated using T4 DNA ligase according to the usual method to construct a plasmid pCGTG4S6H. The outline of the method is shown in FIG. 18.

The plasmid pCGTG4S6H was incorporated into *Escherichia coli* HB101 by a known method to construct a transformant *Escherichia coli* pCGTG4S6H/HB101.

A plasmid pCGTG4S6H was produced by the alkali SDS method starting from the transformed bacteria pCGTG4S6H/HB101 thus produced and incorporated into *Saccharomyces cerevisiae* INVSC2 strain (MAT α, his3-Δ200, ura3-167) using Yeast-Transforming Kit for the alkali cation method (available from Bio101 Company).

The selection of the transformant was using a glucose synthesis minimum medium plate (the synthesis minimum medium comprised 0.17% Yeast Nitrogen Base W/O Amino Acids and Ammonium Sulfate (available from Difco Company) and 0.5% ammonium sulfate and the plate was prepared by adding glucose in such an amount that the final concentration thereof was 2% to the medium and then solidifying in a 90 mm petri dish using a 2% agar) comprising 50 mg/ml of histidine, to thus give a transformant *Saccharomyces cerevisiae* INVSC2/pCGTG4S6H AJ14698. In this respect, the transformant *Saccharomyces cerevisiae* INVSC2/pCGTG4S6H AJ14698 is deposited with Seimeiken under the accession number of FERM BP-4960.

The transformant was first inoculated on 50 ml of a glucose synthesis minimum medium (prepared by adding 2% glucose and 50 mg/ml of histidine to the foregoing synthesis minimum medium) contained in a Sakaguchi flask and cultivated at 30° C. for 24 hours by shaking culture to increase the number of the bacterial cells. Thereafter, the culture medium was centrifuged to collect the cells, then the cells were suspended in a Sakaguchi flask containing 50 ml of a galactose synthesis minimum medium (prepared by adding 2% galactose to the foregoing synthesis minimum medium) and cultured at 30° C. for 24 hours by shaking culture to induce the transcription from the GAL1 promoter.

The *Saccharomyces cerevisiae* INVSC2 strain free of the plasmid was likewise cultivated using the foregoing glucose, galactose synthesis minimum medium to which 50 mg/ml of uracil was further added.

After the cultivation, the cells included in 50 ml of the culture medium was collected through centrifugation and suspended in Buffer A (6M guanidine-HCl, 0.1M sodium dihydrogen phosphate, 0.01M Tris-HCl, pH 8.0). The cell suspension (1 ml) was introduced into a 1.5 ml Eppendorf tube, followed by addition of 0.5 ml volume glass beads (diameter: 0.5 mm) and vigorous stirring for 2 minutes to crush the cells. Then the suspension was centrifuged at 15000 rpm for 2 minutes and the resulting supernatant was passed through an Ni-NTA (nitrilo-tri-acetic acid) column (available from Quiagen Company) equilibrated, in advance, with Buffer B (8M urea, 0.1M sodium dihydrogen phosphate, 0.01M Tris-HCl, pH 8.0). After washing the column with Buffer C (8M urea, 0.1M sodium dihydrogen phosphate, 0.01M Tris-HCl, pH 6.3), the recombinant protein adsorbed on the resin was eluted with Buffer E (8M urea, 0.1M sodium dihydrogen phosphate, 0.01M Tris-HCl, pH 4.5) to give the purified recombinant protein.

Each supernatant obtained through the centrifugation after crushing the bacterial cells (0.35 ml) was inspected for the transglutaminase activity by the same method used in Example 8 (Table 6). As a result, it was found that the crushed cell extract of the transformed yeast (FERM BP-4964) comprising the *Crassostrea gigas* transglutaminase-expressing plasmid (pCGTG4S) whose transcription from the GAL1 promoter had been induced clearly showed the transglutaminase activity. This clearly indicate that the cDNA thus obtained can express the transglutaminase having high activity even in yeast.

The recombinant type transglutaminase of *Crassostrea gigas* thus purified above was adsorbed on a PVDF membrane (available from Millipore Company) and then the membrane as such was supplied to a protein sequencer (PPSQ-10, available from Shimadzu Corporation). As a result, it was found that the N-terminal portion of the recombinant type enzyme expressed in yeast had an amino acid sequence of, from the side of the N-terminal, Ala-Phe-Trp-Gly-Val-Phe-Tyr (SEQ ID NO:149). In other words, the recombinant type transglutaminase of *Crassostrea gigas* expressed in yeast cells had an amino acid sequence corresponding to that deduced based on the cDNA from which the methionine residue serving as an initiation codon was eliminated.

The fact that the crushed cell liquid prepared from *Saccharomyces cerevisiae* INVSC2/pCGTG4S6H AJ 14698 (FERM BP-4960) exhibited the transglutaminase activity was confirmed by the same method used in Example 11.

The inventors of this invention have succeeded in the isolation of a novel transglutaminase from *Crassostrea gigas* which has long been a food quite familiar to human beings and eaten without cooking in many parts of the world. Moreover, the inventors have found that the transglutaminase originating from *Crassostrea gigas* has characteristic properties peculiar thereto such as $Ca^{2+}$ requirement upon onset of the activity thereof greatly different from that observed for other transglutaminases and the activity susceptible to the NaCl concentration.

These characteristic properties of the transglutaminase of the present invention have not conventionally been known, properties of the reaction products in which the transglutaminase is used can be controlled by regulating the enzyme activity while making use of these properties and these properties of the enzyme would permit a substantial extension of the scope of the industrial application thereof.

Moreover, to secure the supply thereof, the inventors have succeeded in the isolation of a gene coding for the transglutaminase of *Crassostrea gigas* and the expression of the genetic recombinant type transglutaminase in *Escherichia coli* and yeast. Thus, the transglutaminase of *Crassostrea gigas* can be mass-produced without using expensive *Crassostrea gigas* per se as a raw material. Moreover, the industrial value of the transglutaminase have become more important than before, i.e., it can be applied to, for instance, the quality improvement in physical properties and the nutritive value of food proteins and the production of medicines and cosmetics while making the most use of the characteristic properties of the enzyme produced by the foregoing microorganisms.

---

We claim:

1. A transglutaminase enzyme originating from *Crassostrea gigas* having the following characteristics:

a) substrate specificity in which said enzyme catalyzes the transfer of an acyl group between primary amines and γ-carboxyamide groups of accessible glutamine residues present in a protein or a polypeptide chain;

b) molecular weight as determined by SDS-PAGE is about 83,000 to 95,000 Da;

c) optimal temperature range of 30° C. to 50°;

d) optimal pH range of about 7.5 to 9.5;

e) activation by calcium ions with further enhancement of activity by NaCl or KCl; and f) inhibition by N-ethylmaleimide, monoiodo acetic acid, p-chloromercuribenzoic acid or $Cu^{2+}$.

2. The transglutaminase of claim 1 which comprises an amino acid sequence of SEQ ID NO:141 or 142.

3. A purified and isolated gene encoding the *Crassostrea gigas* transglutaminase enzyme of claim 1.

4. The gene of claim 3 which has a sequence encoding SEQ ID NO:1.

5. The gene of claim 3 which has a sequence encoding SEQ ID NO:3.

6. The gene of claim 3 which has the sequence of SEQ ID NO:2.

7. The gene of claim 3 which has the sequence of SEQ ID NO:4.

8. The gene of claim 3 which hybridizes to the complement of the strand of a) the DNA encoding SEQ ID NO: 1 or 3, or b)DNA having SEQ ID NO: 2 or 4 and encodes an enzyme having the same activity as the transglutaminase of claim 1.

9. A plasmid containing the gene of claim 3.

10. An isolated cell transformed with the plasmid of claim 9.

11. The cell of claim 10 which is *Escherichia coil* or *Saccharomyces cerevisiae*.

12. A method for obtaining a transglutaminase originating from *Crassostrea gigas* comprising the steps of cultivating the transformed cell of claim 10 to produce the enzyme and isolating it from the medium.

13. A transglutaminase originating from *Crassostrea gigas* prepared by the method of claim 12.

14. A gelling agent comprising a transglutaminase originating from *Crassostrea gigas*.

15. The gelling agent of claim 14 wherein the transglutaminase originating from *Crassostrea gigas* is that set forth in claim 1.

16. The gelling agent of claim 14 wherein the transglutaminase originating from *Crassostrea gigas* is that set forth in claim 13.

17. A method for gelating a protein comprising treating a protein solution or slurry having a concentration of not less than 0.1% by weight with a transglutaminase originating from *Crassostrea gigas* for a time sufficient to convert the solution or slurry into a gel.

18. The gelling method of claim 17 wherein the transglutaminase originating from *Crassostrea gigas* is that set forth in claim 1.

19. The gelling method of claim 17, wherein the transglutaminase originating from *Crassostrea gigas* is that set forth in claim 13.

20. The gelling method of claim 17, wherein the gelation of the protein solution or slurry is controlled by adjusting the concentration of a salt.

21. The gelling method of claim 20, wherein the salt is NaCl or KCl.

22. The gelling method of claim 17, wherein the gelation of the protein solution or slurry is controlled by adjusting the concentration of calcium ions.

* * * * *

SEQUENCE LISTING ( 1 ) GENERAL INFORMATION:

( i i i ) NUMBER OF SEQUENCES: 150

( 2 ) INFORMATION FOR SEQ ID NO:1:

( i ) SEQUENCE CHARACTERISTICS:
        ( A ) LENGTH: 770 amino acids
        ( B ) TYPE: amino acid
        ( C ) STRANDEDNESS: single
        ( D ) TOPOLOGY: linear ( i i ) MOLECULE TYPE: protein ( v i ) ORIGINAL SOURCE:
    ( A ) ORGANISM: Crassostrea gigas ( x i ) SEQUENCE DESCRIPTION: SEQ ID NO:1:

```
Ala  Phe  Trp  Gly  Val  Phe  Tyr  Thr  Ile  Tyr  Ser  Gly  Ile  Arg  Arg  Ile
 1              5                        10                       15

Ala  Gly  Gln  Pro  Pro  Glu  Glu  Asp  Thr  Ser  Asp  Lys  Glu  Gln  Lys  Arg
           20                        25                        30

Ser  Arg  Thr  Lys  Lys  Ala  Leu  Gly  Ser  Glu  Glu  Glu  Gly  Arg  Ile
          35                        40                        45

Ser  Ser  Leu  Ser  Asp  Glu  Asp  Leu  Arg  Ala  Arg  Asn  Lys  Val  Leu  Glu
      50                        55                        60

Pro  Lys  Asp  Glu  Pro  Ser  Ala  Thr  Leu  Asn  Val  Ser  Ser  Val  Asp  Cys
 65                        70                        75                        80

Gln  Thr  Lys  Leu  Asn  Arg  Lys  Asn  His  His  Thr  Asn  Glu  Phe  Glu  Lys
                     85                        90                        95

Ala  Gly  Asn  Ile  Tyr  Arg  Arg  Gly  Gln  Ala  Phe  Val  Ile  Arg  Val  Glu
                100                       105                       110

Phe  Asp  Arg  Glu  Val  Asn  Ser  Asp  His  Asp  Val  Ile  Leu  Leu  Gln  Phe
          115                       120                       125

Thr  Tyr  Gly  Ser  Arg  Pro  Gln  Glu  Ser  Lys  Gly  Thr  Val  Ile  Arg  Ile
     130                       135                       140

Pro  Leu  Asp  Leu  Lys  Pro  Thr  Thr  Lys  Thr  Ser  Asp  Val  Thr  Glu  Thr
145                       150                       155                       160

Trp  Phe  Ala  Glu  Val  Lys  Asn  Ile  Ala  Gly  Lys  Gly  Leu  Glu  Cys  Ala
                     165                       170                       175

Ile  Thr  Ser  Ala  Pro  Asp  Ser  Ser  Ile  Gly  Glu  Tyr  Arg  Phe  Tyr  Ile
                180                       185                       190

Glu  Thr  Asn  Leu  Lys  Asp  Thr  Asp  Ala  Val  Lys  Arg  Tyr  Glu  Glu  Asn
          195                       200                       205

Glu  Ser  Met  Ile  Ile  Leu  Phe  Asn  Ala  Trp  Ala  Lys  Glu  Asp  Thr  Val
     210                       215                       220

Tyr  Met  Asp  Lys  Glu  Gly  Glu  Arg  Gly  Glu  Tyr  Val  Leu  Asn  Glu  Thr
225                       230                       235                       240

Gly  Arg  Val  Trp  Thr  Ser  Arg  Thr  Trp  Tyr  Gly  Arg  Pro  Trp  Asn  Phe
                245                       250                       255

Gly  Gln  Phe  Asp  Asp  Pro  Val  Leu  Asp  Val  Ala  Leu  Gln  Leu  Leu  Leu
                260                       265                       270

Glu  Gly  Gly  Leu  Ser  Asp  Val  Ala  Cys  Thr  Ser  Pro  Val  Ser  Val  Ile
          275                       280                       285

Arg  Cys  Leu  Ser  Ser  Leu  Cys  Asn  Ser  Cys  Asp  Asn  Asn  Gly  Val  Leu
     290                       295                       300

Ala  Gly  Arg  Trp  Thr  Lys  Glu  Tyr  Pro  Lys  Asp  Cys  Thr  Val  Pro  Trp
305                       310                       315                       320

Lys  Trp  Thr  Gly  Ser  Val  Ala  Ile  Ile  Lys  Glu  Tyr  His  Thr  Asn  Gly
                325                       330                       335

Asn  Lys  Pro  Val  Arg  Tyr  Gly  Gln  Cys  Trp  Val  Phe  Ser  Gly  Leu  Leu
                340                       345                       350

Thr  Thr  Met  Cys  Arg  Cys  Leu  Gly  Ile  Pro  Thr  Arg  Ser  Val  Thr  Asn
          355                       360                       365

Phe  Asp  Ser  Ala  His  Asp  Thr  Asp  Ser  Ser  Met  Thr  Ile  Asp  Ser  His
          370                       375                       380

Trp  Asp  Glu  Asp  Gly  Glu  Pro  Leu  Glu  Asp  Met  Asn  Asp  Ser  Val  Trp
385                       390                       395                       400
```

```
Asn Phe His Val Trp Asn Glu Ser Trp Phe Arg Arg Leu Asp Leu Pro
            405                 410                 415
Glu Gly Tyr Asp Gly Trp Gln Ala His Asp Ala Thr Pro Gln Glu Ala
            420                 425                 430
Ser Glu Gly Ile Met Arg Cys Gly Pro Ala Pro Leu Thr Ala Ile Lys
            435                 440                 445
Glu Gly His Val Tyr Leu Asn Phe Asp Ile Pro Phe Val Phe Gly Glu
            450                 455                 460
Val Asn Gly Asp Arg Val Gln Trp Val Val Lys Lys Asp Gly Thr Met
465                 470                 475                 480
Glu Val Ser Gln Ile Asp His Ser Ala Val Gly His Tyr Ile Ser Thr
                    485                 490                 495
Lys Arg Met Gly Ser Asn Asp Arg Glu Asp Val Thr Asn Leu Tyr Lys
            500                 505                 510
Tyr Pro Asp Gly Ser Glu Gln Glu Arg Arg Val Ala Lys Phe Val Asn
            515                 520                 525
Arg Tyr Ser Thr Arg Arg Lys Gln Asn Ile Tyr Lys Leu Asp Thr Thr
            530                 535                 540
Lys Val Leu Lys Phe Thr Val Ser Pro Pro Asp Asn Thr Leu Ile Gly
545                 550                 555                 560
Asp Asp Met Glu Ile Lys Val Ala Val Lys Asn Thr Ala Asp Gly Pro
                    565                 570                 575
Leu Lys Leu His Leu Thr Val Ser Leu Val Asn Ala Tyr Tyr Thr Gly
            580                 585                 590
Val Ala Gly Ser Arg Val Lys Thr Gln Thr Phe Glu Glu Thr Ile Lys
            595                 600                 605
Ala Lys Asp Glu Lys Ile Val Thr Met Pro Val Lys Gly Thr Glu Tyr
            610                 615                 620
His Asp Gly Met Asn Pro Glu Gly Arg Phe Gln Leu Tyr Ile Ser Gly
625                 630                 635                 640
Lys Asn Ile Asp Ser Gly Ser Met Glu Ser Thr Gln Ile Ser Phe Val
                    645                 650                 655
Leu Lys Lys Pro Gln Leu Val Ile Gln Val Pro Gln Thr Ile Glu Ala
            660                 665                 670
Lys Glu Glu Thr Glu Ala Thr Ile Val Phe Lys Asn Thr Thr Gln Leu
            675                 680                 685
Val Leu Thr Gln Ala Glu Ile Ala Val Glu Gly Ser Gly Leu Leu Ala
            690                 695                 700
Pro Gln Thr Ile Asp Ile Ser Ser Pro Ile Lys Pro Gly Asp Glu Val
705                 710                 715                 720
Lys Lys Thr Val Val Leu Arg Pro Arg Lys Pro Tyr Tyr Trp Gly Arg
                    725                 730                 735
Glu Leu Ile Ala Thr Phe Thr Ser Lys Gln Ile Val Asp Ile Glu Thr
            740                 745                 750
Ser Ala Asp Ile Lys Val Ile Arg Gln Asn Lys Asp Asn Asp Ser Asp
            755                 760                 765
Ser Asp
770
```

( 2 ) INFORMATION FOR SEQ ID NO:2:

( i ) SEQUENCE CHARACTERISTICS:
        ( A ) LENGTH: 2310 base pairs
        ( B ) TYPE: nucleic acid
        ( C ) STRANDEDNESS: double ( D ) TOPOLOGY: linear ( i i ) MOLECULE TYPE: DNA (genomic)

( v i ) ORIGINAL SOURCE:
    ( A ) ORGANISM: Crassostrea gigas ( i x ) FEATURE:
    ( A ) NAME/KEY: misc_feature
    ( B ) LOCATION: 1..2310

( x i ) SEQUENCE DESCRIPTION: SEQ ID NO:2:

```
GCTTTTTGGG GCGTCTTTTA CACGATATAC TCGGGGATTC GTCGCATTGC TGGACAACCC      60
CCCGAGGAAG ATACTAGTGA TAAAGAGCAG AAAAGGAGCA GAACTAAAAA AGCATTGGGC     120
AGTGAAGAAG AAGAGGGACG CATCTCCTCC CTGTCTGATG AAGACTTACG AGCAAGGAAT     180
AAGGTCCTCG AACCAAAGGA CGAACCATCT GCGACTTTGA ATGTAAGTTC TGTAGATTGT     240
CAGACAAAAC TGAACAGAAA GAACCACCAC ACCAATGAAT TTGAAAAAGC GGGAAATATC     300
TACAGAAGGG GACAGGCTTT TGTTATCCGT GTTGAATTTG ATAGGGAAGT CAATTCAGAC     360
CATGACGTCA TACTGCTGCA GTTACTTAC GGTTCACGCC CTCAAGAAAG CAAAGGAACT      420
GTTATCAGAA TTCCCCTTGA TTTAAAACCA ACAACAAAAA CATCCGACGT CACAGAAACA     480
TGGTTTGCGG AAGTGAAGAA TATTGCCGGG AAAGGTCTGG AGTGCGCGAT TACGTCAGCA     540
CCTGACAGCA GTATTGGGGA ATACCGTTTC TACATAGAGA CAAATCTGAA GGACACGGAT     600
GCCGTCAAGA GATACGAAGA GAATGAATCA ATGATCATTC TCTTCAATGC TTGGGCGAAA     660
GAGGATACAG TGTACATGGA CAAGGAGGGA GAGAGGGGGG AGTACGTCCT GAACGAGACC     720
GGAAGAGTCT GGACAAGCCG CACGTGGTAT GGACGACCAT GGAATTTTGG ACAATTTGAT     780
GACCCTGTGC TAGACGTTGC CCTACAATTG TTACTGGAGG GAGGTTTATC AGACGTGGCA     840
TGTACTTCTC CTGTGTCCGT GATCCGCTGC CTGTCGTCAC TGTGCAATTC CTGTGACAAT     900
AATGGAGTTC TGGCGGGTAG ATGGACAAAG GAGTATCCCA AGGACTGCAC AGTACCCTGG     960
AAGTGGACAG GAAGTGTCGC AATCATCAAA GAGTACCACA CCAACGGTAA CAAGCCCGTA    1020
CGATACGGAC AGTGCTGGGT GTTTCCGGT CTTCTTACCA CAATGTGTCG CTGCCTCGGA     1080
ATACCGACCC GGTCTGTGAC AAACTTTGAT TCTGCGCATG ACACCGACAG CAGCATGACG    1140
ATTGACAGCC ATTGGGACGA GGACGGGGAA CCATTAGAAG ACATGAACGA CTCTGTTTGG    1200
AATTTCCATG TATGGAACGA GTCTTGGTTC CGACGTTTAG ACCTTCCCGA GGGTTACGAT    1260
GGTTGGCAGG CTCATGATGC CACGCCTCAG GAAGCAAGCG AAGGAATTAT GAGATGCGGC    1320
CCGGCTCCTC TGACAGCCAT CAAAGAGGGT CACGTGTACC TGAACTTTGA CATACCCTTT    1380
GTCTTTGGCG AGGTCAACGG AGATCGAGTT CAGTGGGTGG TGAAGAAGGA CGGTACAATG    1440
GAGGTAAGCC AGATAGATCA CTCCGCGGTG GGACACTACA TCAGCACCAA GAGGATGGGC    1500
TCAAACGACC GTGAGGACGT CACAAACCTG TACAAATACC CGGATGGAAG TGAACAAGAA    1560
AGAAGAGTTG CCAAATTTGT GAACAGATAC AGTACAAGAA GGAAGCAGAA TATCTACAAG    1620
CTGGACACCA CCAAGGTGTT AAAGTTTACC GTTAGCCCGC CAGATAACAC ACTGATTGGA    1680
GACGATATGG AGATTAAGGT GGCCGTCAAA AACACAGCCG ATGGACCCCT TAAACTTCAT    1740
CTGACTGTGT CACTGGTCAA TGCTTACTAC ACTGGGGTGG CGGGGTCAAG GGTCAAGACG    1800
CAGACGTTTG AGGAAACCAT AAAAGCGAAA GATGAGAAGA TAGTAACTAT GCCCGTTAAA    1860
GGGACAGAGT ATCACGATGG AATGAACCCC GAAGGACGAT TCCAGTTGTA CATCTCTGGG    1920
AAGAACATAG ACTCGGGCAG CATGGAATCC ACGCAAATCT CCTTTGTACT GAAGAAACCA    1980
CAACTTGTTA TACAGGTTCC TCAAACCATT GAAGCGAAAG AGGAAACGGA GGCCACCATT    2040
```

```
GTGTTCAAGA ACACGACACA GCTCGTGCTC ACCCAGGCTG AAATAGCCGT GGAGGGCTCG    2100

GGTCTCCTAG CTCCACAAAC CATAGATATA AGCAGTCCTA TTAAACCTGG TGACGAGGTC    2160

AAGAAAACAG TCGTCCTTCG CCCCCGCAAA CCATACTACT GGGGTCGTGA ACTGATAGCG    2220

ACCTTCACCT CCAAACAGAT TGTCGACATT GAGACCAGCG CCGACATTAA GGTGATCCGA    2280

CAGAACAAAG ATAACGACAG CGACAGTGAC                                      2310
```

( 2 ) INFORMATION FOR SEQ ID NO:3:

( i ) SEQUENCE CHARACTERISTICS:
        ( A ) LENGTH: 771 amino acids
        ( B ) TYPE: amino acid
        ( C ) STRANDEDNESS: single
        ( D ) TOPOLOGY: linear ( i i ) MOLECULE TYPE: protein ( v i ) ORIGINAL SOURCE:
        ( A ) ORGANISM: Crassostrea gigas ( x i ) SEQUENCE DESCRIPTION: SEQ ID NO:3:

```
Met Ala Phe Trp Gly Val Phe Tyr Thr Ile Tyr Ser Gly Ile Arg Arg
 1               5                  10                  15

Ile Ala Gly Gln Pro Pro Glu Glu Asp Thr Ser Asp Lys Glu Gln Lys
             20                  25                  30

Arg Ser Arg Thr Lys Lys Ala Leu Gly Ser Glu Glu Glu Glu Gly Arg
         35                  40                  45

Ile Ser Ser Leu Ser Asp Glu Asp Leu Arg Ala Arg Asn Lys Val Leu
     50                  55                  60

Glu Pro Lys Asp Glu Pro Ser Ala Thr Leu Asn Val Ser Ser Val Asp
 65                  70                  75                  80

Cys Gln Thr Lys Leu Asn Arg Lys Asn His His Thr Asn Glu Phe Glu
                 85                  90                  95

Lys Ala Gly Asn Ile Tyr Arg Arg Gly Gln Ala Phe Val Ile Arg Val
            100                 105                 110

Glu Phe Asp Arg Glu Val Asn Ser Asp His Asp Val Ile Leu Leu Gln
        115                 120                 125

Phe Thr Tyr Gly Ser Arg Pro Gln Glu Ser Lys Gly Thr Val Ile Arg
    130                 135                 140

Ile Pro Leu Asp Leu Lys Pro Thr Thr Lys Thr Ser Asp Val Thr Glu
145                 150                 155                 160

Thr Trp Phe Ala Glu Val Lys Asn Ile Ala Gly Lys Gly Leu Glu Cys
                165                 170                 175

Ala Ile Thr Ser Ala Pro Asp Ser Ser Ile Gly Glu Tyr Arg Phe Tyr
            180                 185                 190

Ile Glu Thr Asn Leu Lys Asp Thr Asp Ala Val Lys Arg Tyr Glu Glu
        195                 200                 205

Asn Glu Ser Met Ile Ile Leu Phe Asn Ala Trp Ala Lys Glu Asp Thr
    210                 215                 220

Val Tyr Met Asp Lys Glu Gly Glu Arg Gly Glu Tyr Val Leu Asn Glu
225                 230                 235                 240

Thr Gly Arg Val Trp Thr Ser Arg Thr Trp Tyr Gly Arg Pro Trp Asn
                245                 250                 255

Phe Gly Gln Phe Asp Asp Pro Val Leu Asp Val Ala Leu Gln Leu Leu
            260                 265                 270

Leu Glu Gly Gly Leu Ser Asp Val Ala Cys Thr Ser Pro Val Ser Val
        275                 280                 285
```

```
Ile Arg Cys Leu Ser Ser Leu Cys Asn Ser Cys Asp Asn Asn Gly Val
    290                 295                 300
Leu Ala Gly Arg Trp Thr Lys Glu Tyr Pro Lys Asp Cys Thr Val Pro
305                 310                 315                 320
Trp Lys Trp Thr Gly Ser Val Ala Ile Ile Lys Glu Tyr His Thr Asn
                325                 330                 335
Gly Asn Lys Pro Val Arg Tyr Gly Gln Cys Trp Val Phe Ser Gly Leu
            340                 345                 350
Leu Thr Thr Met Cys Arg Cys Leu Gly Ile Pro Thr Arg Ser Val Thr
                355                 360                 365
Asn Phe Asp Ser Ala His Asp Thr Asp Ser Ser Met Thr Ile Asp Ser
    370                 375                 380
His Trp Asp Glu Asp Gly Glu Pro Leu Glu Asp Met Asn Asp Ser Val
385                 390                 395                 400
Trp Asn Phe His Val Trp Asn Glu Ser Trp Phe Arg Arg Leu Asp Leu
                405                 410                 415
Pro Glu Gly Tyr Asp Gly Trp Gln Ala His Asp Ala Thr Pro Gln Glu
            420                 425                 430
Ala Ser Glu Gly Ile Met Arg Cys Gly Pro Ala Pro Leu Thr Ala Ile
        435                 440                 445
Lys Glu Gly His Val Tyr Leu Asn Phe Asp Ile Pro Phe Val Phe Gly
450                 455                 460
Glu Val Asn Gly Asp Arg Val Gln Trp Val Val Lys Lys Asp Gly Thr
465                 470                 475                 480
Met Glu Val Ser Gln Ile Asp His Ser Ala Val Gly His Tyr Ile Ser
                485                 490                 495
Thr Lys Arg Met Gly Ser Asn Asp Arg Glu Asp Val Thr Asn Leu Tyr
            500                 505                 510
Lys Tyr Pro Asp Gly Ser Glu Gln Glu Arg Arg Val Ala Lys Phe Val
        515                 520                 525
Asn Arg Tyr Ser Thr Arg Arg Lys Gln Asn Ile Tyr Lys Leu Asp Thr
    530                 535                 540
Thr Lys Val Leu Lys Phe Thr Val Ser Pro Pro Asn Thr Leu Ile
545                 550                 555                 560
Gly Asp Asp Met Glu Ile Lys Val Ala Val Lys Asn Thr Ala Asp Gly
                565                 570                 575
Pro Leu Lys Leu His Leu Thr Val Ser Leu Val Asn Ala Tyr Tyr Thr
            580                 585                 590
Gly Val Ala Gly Ser Arg Val Lys Thr Gln Thr Phe Glu Glu Thr Ile
        595                 600                 605
Lys Ala Lys Asp Glu Lys Ile Val Thr Met Pro Val Lys Gly Thr Glu
610                 615                 620
Tyr His Asp Gly Met Asn Pro Glu Gly Arg Phe Gln Leu Tyr Ile Ser
625                 630                 635                 640
Gly Lys Asn Ile Asp Ser Gly Met Glu Ser Thr Gln Ile Ser Phe
                645                 650                 655
Val Leu Lys Lys Pro Gln Leu Val Ile Gln Val Pro Gln Thr Ile Glu
            660                 665                 670
Ala Lys Glu Glu Thr Glu Ala Thr Ile Val Phe Lys Asn Thr Thr Gln
        675                 680                 685
Leu Val Leu Thr Gln Ala Glu Ile Ala Val Glu Gly Ser Gly Leu Leu
690                 695                 700
Ala Pro Gln Thr Ile Asp Ile Ser Ser Pro Ile Lys Pro Gly Asp Glu
```

```
                705                     710                     715                     720
          Val  Lys  Lys  Thr  Val  Val  Leu  Arg  Pro  Arg  Lys  Pro  Tyr  Tyr  Trp  Gly
                              725                     730                     735

Arg  Glu  Leu  Ile  Ala  Thr  Phe  Thr  Ser  Lys  Gln  Ile  Val  Asp  Ile  Glu
                              740                     745                     750

Thr  Ser  Ala  Asp  Ile  Lys  Val  Ile  Arg  Gln  Asn  Lys  Asp  Asn  Asp  Ser
                         755                     760                     765

Asp  Ser  Asp
                    770
```

( 2 ) INFORMATION FOR SEQ ID NO:4:

( i ) SEQUENCE CHARACTERISTICS:
        ( A ) LENGTH: 2313 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Crassostrea gigas ( i x ) FEATURE:
        ( A ) NAME/KEY: misc_feature
        ( B ) LOCATION: 1..2054

( x i ) SEQUENCE DESCRIPTION: SEQ ID NO:4:

```
ATGGCTTTTT  GGGGCGTCTT  TTACACGATA  TACTCGGGGA  TTCGTCGCAT  TGCTGGACAA    60

CCCCCCGAGG  AAGATACTAG  TGATAAAGAG  CAGAAAAGGA  GCAGAACTAA  AAAAGCATTG   120

GGCAGTGAAG  AAGAAGAGGG  ACGCATCTCC  TCCCTGTCTG  ATGAAGACTT  ACGAGCAAGG   180

AATAAGGTCC  TCGAACCAAA  GGACGAACCA  TCTGCGACTT  TGAATGTAAG  TTCTGTAGAT   240

TGTCAGACAA  AACTGAACAG  AAAGAACCAC  CACACCAATG  AATTTGAAAA  AGCCGGAAAT   300

ATCTACAGAA  GGGGACAGGC  TTTTGTTATC  CGTGTTGAAT  TGATAGGGA   AGTCAATTCA   360

GACCATGACG  TCATACTGCT  GCAGTTTACT  TACGGTTCAC  GCCCTCAAGA  AAGCAAAGGA   420

ACTGTTATCA  GAATTCCCCT  TGATTTAAAA  CCAACAACAA  AAACATCCGA  CGTCACAGAA   480

ACATGGTTTG  CGGAAGTGAA  GAATATTGCC  GGGAAAGGTC  TGGAGTGCGC  GATTACGTCA   540

GCACCTGACA  GCAGTATTGG  GGAATACCGT  TTCTACATAG  AGACAAATCT  GAAGGACACG   600

GATGCCGTCA  AGAGATACGA  AGAGAATGAA  TCAATGATCA  TTCTCTTCAA  TGCTTGGGCG   660

AAAGAGGATA  CAGTGTACAT  GGACAAGGAG  GGAGAGAGGG  GGGAGTACGT  CCTGAACGAG   720

ACCGGAAGAG  TCTGGACAAG  CCGCACGTGG  TATGGACGAC  CATGGAATTT  TGGACAATTT   780

GATGACCCTG  TGCTAGACGT  TGCCCTACAA  TTGTTACTGG  AGGGAGGTTT  ATCAGACGTG   840

GCATGTACTT  CTCCTGTGTC  CGTGATCCGC  TGCCTGTCGT  CACTGTGCAA  TTCCTGTGAC   900

AATAATGGAG  TTCTGGCGGG  TAGATGGACA  AAGGAGTATC  CCAAGGACTG  CACAGTACCC   960

TGGAAGTGGA  CAGGAAGTGT  CGCAATCATC  AAAGAGTACC  ACACCAACGG  TAACAAGCCC  1020

GTACGATACG  GACAGTGCTG  GGTGTTTTCC  GGTCTTCTTA  CCACAATGTG  TCGCTGCCTC  1080

GGAATACCGA  CCCGGTCTGT  GACAAACTTT  GATTCTGCGC  ATGACACCGA  CAGCAGCATG  1140

ACGATTGACA  GCCATTGGGA  CGAGGACGGG  GAACCATTAG  AAGACATGAA  CGACTCTGTT  1200

TGGAATTTCC  ATGTATGGAA  CGAGTCTTGG  TTCGACGTT   TAGACCTTCC  CGAGGGTTAC  1260

GATGGTTGGC  AGGCTCATGA  TGCCACGCCT  CAGGAAGCAA  GCGAAGGAAT  TATGAGATGC  1320

GGCCCGGCTC  CTCTGACAGC  CATCAAAGAG  GGTCACGTGT  ACCTGAACTT  TGACATACCC  1380
```

| | | | | | | |
|---|---|---|---|---|---|---|
| TTTGTCTTTG | GCGAGGTCAA | CGGAGATCGA | GTTCAGTGGG | TGGTGAAGAA | GGACGGTACA | 1440 |
| ATGGAGGTAA | GCCAGATAGA | TCACTCCGCG | GTGGGACACT | ACATCAGCAC | CAAGAGGATG | 1500 |
| GGCTCAAACG | ACCGTGAGGA | CGTCACAAAC | CTGTACAAAT | ACCCGGATGG | AAGTGAACAA | 1560 |
| GAAAGAAGAG | TTGCCAAATT | TGTGAACAGA | TACAGTACAA | GAAGGAAGCA | GAATATCTAC | 1620 |
| AAGCTGGACA | CCACCAAGGT | GTTAAAGTTT | ACCGTTAGCC | CGCCAGATAA | CACACTGATT | 1680 |
| GGAGACGATA | TGGAGATTAA | GGTGGCCGTC | AAAAACACAG | CCGATGGACC | CCTTAAACTT | 1740 |
| CATCTGACTG | TGTCACTGGT | CAATGCTTAC | TACACTGGGG | TGGCGGGGTC | AAGGGTCAAG | 1800 |
| ACGCAGACGT | TTGAGGAAAC | CATAAAAGCG | AAAGATGAGA | AGATAGTAAC | TATGCCCGTT | 1860 |
| AAAGGGACAG | AGTATCACGA | TGGAATGAAC | CCCGAAGGAC | GATTCCAGTT | GTACATCTCT | 1920 |
| GGGAAGAACA | TAGACTCGGG | CAGCATGGAA | TCCACGCAAA | TCTCCTTTGT | ACTGAAGAAA | 1980 |
| CCACAACTTG | TTATACAGGT | TCCTCAAACC | ATTGAAGCGA | AAGAGGAAAC | GGAGGCCACC | 2040 |
| ATTGTGTTCA | AGAACACGAC | ACAGCTCGTG | CTCACCCAGG | CTGAAATAGC | CGTGGAGGGC | 2100 |
| TCGGGTCTCC | TAGCTCCACA | AACCATAGAT | ATAAGCAGTC | CTATTAAACC | TGGTGACGAG | 2160 |
| GTCAAGAAAA | CAGTCGTCCT | TCGCCCCCGC | AAACCATACT | ACTGGGGTCG | TGAACTGATA | 2220 |
| GCGACCTTCA | CCTCCAAACA | GATTGTCGAC | ATTGAGACCA | GCGCCGACAT | TAAGGTGATC | 2280 |
| CGACAGAACA | AAGATAACGA | CAGCGACAGT | GAC | | | 2313 |

( 2 ) INFORMATION FOR SEQ ID NO:5:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA, N REPRESENTS
        INOSINE"

( x i ) SEQUENCE DESCRIPTION: SEQ ID NO:5:

CATCATACNA ATGAATTTGA A          21

( 2 ) INFORMATION FOR SEQ ID NO:6:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA, N REPRESENTS
        INOSINE"

( x i ) SEQUENCE DESCRIPTION: SEQ ID NO:6:

CATCATACNA ATGAATTCGA G          21

( 2 ) INFORMATION FOR SEQ ID NO:7:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA, N REPRESENTS
        INOSINE"

( x i ) SEQUENCE DESCRIPTION: SEQ ID NO:7:

CATCATACNA ATGAATTCGA A                           21

( 2 ) INFORMATION FOR SEQ ID NO:8:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA, N REPRESENTS
            INOSINE"

( x i ) SEQUENCE DESCRIPTION: SEQ ID NO:8:

CATCATACNA ATGAATTCGA G                           21

( 2 ) INFORMATION FOR SEQ ID NO:9:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA, N REPRESENTS
            INOSINE"

( x i ) SEQUENCE DESCRIPTION: SEQ ID NO:9:

CATCATACNA ATGAGTTTGA A                           21

( 2 ) INFORMATION FOR SEQ ID NO:10:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA, N REPRESENTS
            INOSINE"

( x i ) SEQUENCE DESCRIPTION: SEQ ID NO:10:

CATCATACNA ATGAGTTTGA G                           21

( 2 ) INFORMATION FOR SEQ ID NO:11:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA, N REPRESENTS
            INOSINE"

( x i ) SEQUENCE DESCRIPTION: SEQ ID NO:11:

CATCATACNA ATGAGTTCGA A                           21

( 2 ) INFORMATION FOR SEQ ID NO:12:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
   ( A ) DESCRIPTION: /desc = "SYNTHETIC DNA, N REPRESENTS INOSINE"

( x i ) SEQUENCE DESCRIPTION: SEQ ID NO:12:

CATCATACNA ATGAGTTCGA G  21

( 2 ) INFORMATION FOR SEQ ID NO:13:

( i ) SEQUENCE CHARACTERISTICS:
   ( A ) LENGTH: 21 base pairs
   ( B ) TYPE: nucleic acid
   ( C ) STRANDEDNESS: single
   ( D ) TOPOLOGY: linear ( i i ) MOLECULE TYPE: other nucleic acid
   ( A ) DESCRIPTION: /desc = "SYNTHETIC DNA, N REPRESENTS INOSINE"

( x i ) SEQUENCE DESCRIPTION: SEQ ID NO:13:

CATCATACNA ACGAATTTGA A  21

( 2 ) INFORMATION FOR SEQ ID NO:14:

( i ) SEQUENCE CHARACTERISTICS:
   ( A ) LENGTH: 21 base pairs
   ( B ) TYPE: nucleic acid
   ( C ) STRANDEDNESS: single
   ( D ) TOPOLOGY: linear ( i i ) MOLECULE TYPE: other nucleic acid
   ( A ) DESCRIPTION: /desc = "SYNTHETIC DNA, N REPRESENTS INOSINE"

( x i ) SEQUENCE DESCRIPTION: SEQ ID NO:14:

CATCATACNA ACGAATTTGA G  21

( 2 ) INFORMATION FOR SEQ ID NO:15:

( i ) SEQUENCE CHARACTERISTICS:
   ( A ) LENGTH: 21 base pairs
   ( B ) TYPE: nucleic acid
   ( C ) STRANDEDNESS: single
   ( D ) TOPOLOGY: linear ( i i ) MOLECULE TYPE: other nucleic acid
   ( A ) DESCRIPTION: /desc = "SYNTHETIC DNA, N REPRESENTS INOSINE"

( x i ) SEQUENCE DESCRIPTION: SEQ ID NO:15:

CATCATACNA ACGAATTCGA A  21

( 2 ) INFORMATION FOR SEQ ID NO:16:

( i ) SEQUENCE CHARACTERISTICS:
   ( A ) LENGTH: 21 base pairs
   ( B ) TYPE: nucleic acid
   ( C ) STRANDEDNESS: single
   ( D ) TOPOLOGY: linear ( i i ) MOLECULE TYPE: other nucleic acid
   ( A ) DESCRIPTION: /desc = "SYNTHETIC DNA, N REPRESENTS INOSINE"

( x i ) SEQUENCE DESCRIPTION: SEQ ID NO:16:

CATCATACNA ACGAATTCGA G  21

( 2 ) INFORMATION FOR SEQ ID NO:17:

( i ) SEQUENCE CHARACTERISTICS:

(A) LENGTH: 21 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "SYNTHETIC DNA, N REPRESENTS
                INOSINE"

(xi) SEQUENCE DESCRIPTION: SEQ ID NO:17:

CATCATACNA ACGAGTTTGA A                    21

( 2 ) INFORMATION FOR SEQ ID NO:18:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "SYNTHETIC DNA, N REPRESENTS
                INOSINE"

(xi) SEQUENCE DESCRIPTION: SEQ ID NO:18:

CATCATACNA ACGAGTTTGA G                    21

( 2 ) INFORMATION FOR SEQ ID NO:19:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "SYNTHETIC DNA, N REPRESENTS
                INOSINE"

(xi) SEQUENCE DESCRIPTION: SEQ ID NO:19:

CATCATACNA ACGAGTTCGA A                    21

( 2 ) INFORMATION FOR SEQ ID NO:20:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "SYNTHETIC DNA, N REPRESENTS
                INOSINE"

(xi) SEQUENCE DESCRIPTION: SEQ ID NO:20:

CATCATACNA ACGAGTTCGA G                    21

( 2 ) INFORMATION FOR SEQ ID NO:21:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "SYNTHETIC DNA, N REPRESENTS
                INOSINE"

(xi) SEQUENCE DESCRIPTION: SEQ ID NO:21:

CATCACACNA ATGAATTTGA A                    21

( 2 ) INFORMATION FOR SEQ ID NO:22:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "SYNTHETIC DNA, N REPRESENTS INOSINE"

( x i ) SEQUENCE DESCRIPTION: SEQ ID NO:22:

CATCACACNA ATGAATTTGA G                         21

( 2 ) INFORMATION FOR SEQ ID NO:23:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "SYNTHETIC DNA, N REPRESENTS INOSINE"

( x i ) SEQUENCE DESCRIPTION: SEQ ID NO:23:

CATCACACNA ATGAATTCGA A                         21

( 2 ) INFORMATION FOR SEQ ID NO:24:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "SYNTHETIC DNA, N REPRESENTS INOSINE"

( x i ) SEQUENCE DESCRIPTION: SEQ ID NO:24:

CATCACACNA ATGAATTCGA G                         21

( 2 ) INFORMATION FOR SEQ ID NO:25:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "SYNTHETIC DNA, N REPRESENTS INOSINE"

( x i ) SEQUENCE DESCRIPTION: SEQ ID NO:25:

CATCACACNA ATGAGTTTGA A                         21

( 2 ) INFORMATION FOR SEQ ID NO:26:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "SYNTHETIC DNA, N REPRESENTS

INOSINE"

( x i ) SEQUENCE DESCRIPTION: SEQ ID NO:26:

CATCACACNA ATGAGTTTGA G     21

( 2 ) INFORMATION FOR SEQ ID NO:27:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA, N REPRESENTS
            INOSINE"

( x i ) SEQUENCE DESCRIPTION: SEQ ID NO:27:

CATCACACNA ATGAGTTCGA A     21

( 2 ) INFORMATION FOR SEQ ID NO:28:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA, N REPRESENTS
            INOSINE"

( x i ) SEQUENCE DESCRIPTION: SEQ ID NO:28:

CATCACACNA ATGAGTTCGA G     21

( 2 ) INFORMATION FOR SEQ ID NO:29:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA, N REPRESENTS
            INOSINE"

( x i ) SEQUENCE DESCRIPTION: SEQ ID NO:29:

CATCACACNA ACGAATTTGA A     21

( 2 ) INFORMATION FOR SEQ ID NO:30:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA, N REPRESENTS
            INOSINE"

( x i ) SEQUENCE DESCRIPTION: SEQ ID NO:30:

CATCACACNA ACGAATTTGA G     21

( 2 ) INFORMATION FOR SEQ ID NO:31:

( i ) SEQUENCE CHARACTERISTICS:
        ( A ) LENGTH: 21 base pairs
        ( B ) TYPE: nucleic acid (C) STRANDEDNESS: single
            (D) TOPOLOGY: linear (i i) MOLECULE TYPE: other nucleic acid
            (A) DESCRIPTION: /desc = "SYNTHETIC DNA, N REPRESENTS
                INOSINE"

(x i) SEQUENCE DESCRIPTION: SEQ ID NO:31:

CATCACACNA ACGAATTCGA A    21

(2) INFORMATION FOR SEQ ID NO:32:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (i i) MOLECULE TYPE: other nucleic acid
            (A) DESCRIPTION: /desc = "SYNTHETIC DNA, N REPRESENTS
                INOSINE"

(x i) SEQUENCE DESCRIPTION: SEQ ID NO:32:

CATCACACNA ACGAATTCGA G    21

(2) INFORMATION FOR SEQ ID NO:33:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (i i) MOLECULE TYPE: other nucleic acid
            (A) DESCRIPTION: /desc = "SYNTHETIC DNA, N REPRESENTS
                INOSINE"

(x i) SEQUENCE DESCRIPTION: SEQ ID NO:33:

CATCACACNA ACGAGTTTGA A    21

(2) INFORMATION FOR SEQ ID NO:34:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (i i) MOLECULE TYPE: other nucleic acid
            (A) DESCRIPTION: /desc = "SYNTHETIC DNA, N REPRESENTS
                INOSINE"

(x i) SEQUENCE DESCRIPTION: SEQ ID NO:34:

CATCACACNA ACGAGTTTGA G    21

(2) INFORMATION FOR SEQ ID NO:35:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (i i) MOLECULE TYPE: other nucleic acid
            (A) DESCRIPTION: /desc = "SYNTHETIC DNA, N REPRESENTS
                INOSINE"

(x i) SEQUENCE DESCRIPTION: SEQ ID NO:35:

CATCACACNA ACGAGTTCGA A    21

( 2 ) INFORMATION FOR SEQ ID NO:36:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA, N REPRESENTS INOSINE"

( x i ) SEQUENCE DESCRIPTION: SEQ ID NO:36:

CATCACACNA ACGAGTTCGA G        21

( 2 ) INFORMATION FOR SEQ ID NO:37:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA, N REPRESENTS INOSINE"

( x i ) SEQUENCE DESCRIPTION: SEQ ID NO:37:

CACCATACNA ATGAATTTGA A        21

( 2 ) INFORMATION FOR SEQ ID NO:38:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA, N REPRESENTS INOSINE"

( x i ) SEQUENCE DESCRIPTION: SEQ ID NO:38:

CACCATACNA ATGAATTTGA G        21

( 2 ) INFORMATION FOR SEQ ID NO:39:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA, N REPRESENTS INOSINE"

( x i ) SEQUENCE DESCRIPTION: SEQ ID NO:39:

CACCATACNA ATGAATTCGA A        21

( 2 ) INFORMATION FOR SEQ ID NO:40:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA, N REPRESENTS INOSINE"

( x i ) SEQUENCE DESCRIPTION: SEQ ID NO:40:

CACCATACNA ATGAATTCGA G  21

( 2 ) INFORMATION FOR SEQ ID NO:41:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA, N REPRESENTS
            INOSINE"

( x i ) SEQUENCE DESCRIPTION: SEQ ID NO:41:

CACCATACNA ATGAGTTTGA A  21

( 2 ) INFORMATION FOR SEQ ID NO:42:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA, N REPRESENTS
            INOSINE"

( x i ) SEQUENCE DESCRIPTION: SEQ ID NO:42:

CACCATACNA ATGAGTTTGA G  21

( 2 ) INFORMATION FOR SEQ ID NO:43:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA, N REPRESENTS
            INOSINE"

( x i ) SEQUENCE DESCRIPTION: SEQ ID NO:43:

CACCATACNA ATGAGTTCGA A  21

( 2 ) INFORMATION FOR SEQ ID NO:44:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA, N REPRESENTS
            INOSINE"

( x i ) SEQUENCE DESCRIPTION: SEQ ID NO:44:

CACCATACNA ATGAGTTCGA G  21

( 2 ) INFORMATION FOR SEQ ID NO:45:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
  ( A ) DESCRIPTION: /desc = "SYNTHETIC DNA, N REPRESENTS INOSINE"

( x i ) SEQUENCE DESCRIPTION: SEQ ID NO:45:

CACCATACNA ACGAATTTGA A  21

( 2 ) INFORMATION FOR SEQ ID NO:46:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "SYNTHETIC DNA, N REPRESENTS INOSINE"

( x i ) SEQUENCE DESCRIPTION: SEQ ID NO:46:

CACCATACNA ACGAATTTGA G  21

( 2 ) INFORMATION FOR SEQ ID NO:47:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "SYNTHETIC DNA, N REPRESENTS INOSINE"

( x i ) SEQUENCE DESCRIPTION: SEQ ID NO:47:

CACCATACNA ACGAATTCGA A  21

( 2 ) INFORMATION FOR SEQ ID NO:48:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "SYNTHETIC DNA, N REPRESENTS INOSINE"

( x i ) SEQUENCE DESCRIPTION: SEQ ID NO:48:

CACCATACNA ACGAATTCGA G  21

( 2 ) INFORMATION FOR SEQ ID NO:49:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "SYNTHETIC DNA, N REPRESENTS INOSINE"

( x i ) SEQUENCE DESCRIPTION: SEQ ID NO:49:

CACCATACNA ACGAGTTTGA A  21

( 2 ) INFORMATION FOR SEQ ID NO:50:

(i) SEQUENCE CHARACTERISTICS:
  (A) LENGTH: 21 base pairs
  (B) TYPE: nucleic acid
  (C) STRANDEDNESS: single
  (D) TOPOLOGY: linear (ii) MOLECULE TYPE: other nucleic acid
  (A) DESCRIPTION: /desc = "SYNTHETIC DNA, N REPRESENTS INOSINE"

(xi) SEQUENCE DESCRIPTION: SEQ ID NO:50:

CACCATACNA ACGAGTTTGA G                                                21

(2) INFORMATION FOR SEQ ID NO:51:

(i) SEQUENCE CHARACTERISTICS:
  (A) LENGTH: 21 base pairs
  (B) TYPE: nucleic acid
  (C) STRANDEDNESS: single
  (D) TOPOLOGY: linear (ii) MOLECULE TYPE: other nucleic acid
  (A) DESCRIPTION: /desc = "SYNTHETIC DNA, N REPRESENTS INOSINE"

(xi) SEQUENCE DESCRIPTION: SEQ ID NO:51:

CACCATACNA ACGAGTTCGA A                                                21

(2) INFORMATION FOR SEQ ID NO:52:

(i) SEQUENCE CHARACTERISTICS:
  (A) LENGTH: 21 base pairs
  (B) TYPE: nucleic acid
  (C) STRANDEDNESS: single
  (D) TOPOLOGY: linear (ii) MOLECULE TYPE: other nucleic acid
  (A) DESCRIPTION: /desc = "SYNTHETIC DNA, N REPRESENTS INOSINE"

(xi) SEQUENCE DESCRIPTION: SEQ ID NO:52:

CACCATACNA ACGAGTTCGA G                                                21

(2) INFORMATION FOR SEQ ID NO:53:

(i) SEQUENCE CHARACTERISTICS:
  (A) LENGTH: 21 base pairs
  (B) TYPE: nucleic acid
  (C) STRANDEDNESS: single
  (D) TOPOLOGY: linear (ii) MOLECULE TYPE: other nucleic acid
  (A) DESCRIPTION: /desc = "SYNTHETIC DNA, N REPRESENTS INOSINE"

(xi) SEQUENCE DESCRIPTION: SEQ ID NO:53:

CACCACACNA ATGAATTTGA A                                                21

(2) INFORMATION FOR SEQ ID NO:54:

(i) SEQUENCE CHARACTERISTICS:
  (A) LENGTH: 21 base pairs
  (B) TYPE: nucleic acid
  (C) STRANDEDNESS: single
  (D) TOPOLOGY: linear (ii) MOLECULE TYPE: other nucleic acid
  (A) DESCRIPTION: /desc = "SYNTHETIC DNA, N REPRESENTS INOSINE"

(xi) SEQUENCE DESCRIPTION: SEQ ID NO:54:

CACCACACNA ATGAATTTGA G    21

(2) INFORMATION FOR SEQ ID NO:55:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA, N REPRESENTS
            INOSINE"

(xi) SEQUENCE DESCRIPTION: SEQ ID NO:55:

CACCACACNA ATGAATTCGA A    21

(2) INFORMATION FOR SEQ ID NO:56:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA, N REPRESENTS
            INOSINE"

(xi) SEQUENCE DESCRIPTION: SEQ ID NO:56:

CACCACACNA ATGAATTCGA G    21

(2) INFORMATION FOR SEQ ID NO:57:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA, N REPRESENTS
            INOSINE"

(xi) SEQUENCE DESCRIPTION: SEQ ID NO:57:

CACCACACNA ATGAGTTTGA A    21

(2) INFORMATION FOR SEQ ID NO:58:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA, N REPRESENTS
            INOSINE"

(xi) SEQUENCE DESCRIPTION: SEQ ID NO:58:

CACCACACNA ATGAGTTTGA G    21

(2) INFORMATION FOR SEQ ID NO:59:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid ( A ) DESCRIPTION: /desc = "SYNTHETIC DNA, N REPRESENTS INOSINE"

( x i ) SEQUENCE DESCRIPTION: SEQ ID NO:59:

CACCACACNA ATGAGTTCGA A  21

( 2 ) INFORMATION FOR SEQ ID NO:60:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "SYNTHETIC DNA, N REPRESENTS INOSINE"

( x i ) SEQUENCE DESCRIPTION: SEQ ID NO:60:

CACCACACNA ATGAGTTCGA G  21

( 2 ) INFORMATION FOR SEQ ID NO:61:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "SYNTHETIC DNA, N REPRESENTS INOSINE"

( x i ) SEQUENCE DESCRIPTION: SEQ ID NO:61:

CACCACACNA ACGAATTTGA A  21

( 2 ) INFORMATION FOR SEQ ID NO:62:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "SYNTHETIC DNA, N REPRESENTS INOSINE"

( x i ) SEQUENCE DESCRIPTION: SEQ ID NO:62:

CACCACACNA ACGAATTTGA G  21

( 2 ) INFORMATION FOR SEQ ID NO:63:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "SYNTHETIC DNA, N REPRESENTS INOSINE"

( x i ) SEQUENCE DESCRIPTION: SEQ ID NO:63:

CACCACACNA ACGAATTCGA A  21

( 2 ) INFORMATION FOR SEQ ID NO:64:

( i ) SEQUENCE CHARACTERISTICS:
    ( A ) LENGTH: 21 base pairs

```
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA, N REPRESENTS
              INOSINE"

( x i ) SEQUENCE DESCRIPTION: SEQ ID NO:64:

CACCACACNA ACGAATTCGA G                                              21

( 2 ) INFORMATION FOR SEQ ID NO:65:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA, N REPRESENTS
              INOSINE"

( x i ) SEQUENCE DESCRIPTION: SEQ ID NO:65:

CACCACACNA ACGAGTTTGA A                                              21

( 2 ) INFORMATION FOR SEQ ID NO:66:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA, N REPRESENTS
              INOSINE"

( x i ) SEQUENCE DESCRIPTION: SEQ ID NO:66:

CACCACACNA ACGAGTTTGA G                                              21

( 2 ) INFORMATION FOR SEQ ID NO:67:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA, N REPRESENTS
              INOSINE"

( x i ) SEQUENCE DESCRIPTION: SEQ ID NO:67:

CACCACACNA ACGAGTTCGA A                                              21

( 2 ) INFORMATION FOR SEQ ID NO:68:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA, N REPRESENTS
              INOSINE"

( x i ) SEQUENCE DESCRIPTION: SEQ ID NO:68:

CACCACACNA ACGAGTTCGA G                                              21
```

( 2 ) INFORMATION FOR SEQ ID NO:69:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: other nucleic acid
  ( A ) DESCRIPTION: /desc = "SYNTHETIC DNA, N REPRESENTS INOSINE"

( x i ) SEQUENCE DESCRIPTION: SEQ ID NO:69:

CATNGATTCA TTTTCTTCAT A    21

( 2 ) INFORMATION FOR SEQ ID NO:70:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: other nucleic acid
  ( A ) DESCRIPTION: /desc = "SYNTHETIC DNA, N REPRESENTS INOSINE"

( x i ) SEQUENCE DESCRIPTION: SEQ ID NO:70:

CATNGATTCA TTTTCTTCGT A    21

( 2 ) INFORMATION FOR SEQ ID NO:71:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: other nucleic acid
  ( A ) DESCRIPTION: /desc = "SYNTHETIC DNA, N REPRESENTS INOSINE"

( x i ) SEQUENCE DESCRIPTION: SEQ ID NO:71:

CATNGATTCA TTTTCCTCAT A    21

( 2 ) INFORMATION FOR SEQ ID NO:72:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: other nucleic acid
  ( A ) DESCRIPTION: /desc = "SYNTHETIC DNA, N REPRESENTS INOSINE"

( x i ) SEQUENCE DESCRIPTION: SEQ ID NO:72:

CATNGATTCA TTTTCCTCGT A    21

( 2 ) INFORMATION FOR SEQ ID NO:73:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: other nucleic acid
  ( A ) DESCRIPTION: /desc = "SYNTHETIC DNA, N REPRESENTS INOSINE"

( x i ) SEQUENCE DESCRIPTION: SEQ ID NO:73:

CATNGATTCA TTCTCTTCAT A                                    21

( 2 ) INFORMATION FOR SEQ ID NO:74:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA, N REPRESENTS INOSINE"

( x i ) SEQUENCE DESCRIPTION: SEQ ID NO:74:

CATNGATTCA TTCTCTTCGT A                                    21

( 2 ) INFORMATION FOR SEQ ID NO:75:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA, N REPRESENTS INOSINE"

( x i ) SEQUENCE DESCRIPTION: SEQ ID NO:75:

CATNGATTCA TTCTCCTCAT A                                    21

( 2 ) INFORMATION FOR SEQ ID NO:76:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA, N REPRESENTS INOSINE"

( x i ) SEQUENCE DESCRIPTION: SEQ ID NO:76:

CATNGATTCA TTCTCCTCGT A                                    21

( 2 ) INFORMATION FOR SEQ ID NO:77:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA, N REPRESENTS INOSINE"

( x i ) SEQUENCE DESCRIPTION: SEQ ID NO:77:

CATNGATTCG TTTTCTTCAT A                                    21

( 2 ) INFORMATION FOR SEQ ID NO:78:

( i ) SEQUENCE CHARACTERISTICS:
        ( A ) LENGTH: 21 base pairs
        ( B ) TYPE: nucleic acid
        ( C ) STRANDEDNESS: single (D) TOPOLOGY: linear (i i) MOLECULE TYPE: other nucleic acid
    (A) DESCRIPTION: /desc = "SYNTHETIC DNA, N REPRESENTS INOSINE"

(x i) SEQUENCE DESCRIPTION: SEQ ID NO:78:

CATNGATTCG TTTTCTTCGT A                                          21

(2) INFORMATION FOR SEQ ID NO:79:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "SYNTHETIC DNA, N REPRESENTS INOSINE"

(x i) SEQUENCE DESCRIPTION: SEQ ID NO:79:

CATNGATTCG TTTTCCTCAT A                                          21

(2) INFORMATION FOR SEQ ID NO:80:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "SYNTHETIC DNA, N REPRESENTS INOSINE"

(x i) SEQUENCE DESCRIPTION: SEQ ID NO:80:

CATNGATTCG TTTTCCTCGT A                                          21

(2) INFORMATION FOR SEQ ID NO:81:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "SYNTHETIC DNA, N REPRESENTS INOSINE"

(x i) SEQUENCE DESCRIPTION: SEQ ID NO:81:

CATNGATTCG TTCTCTTCAT A                                          21

(2) INFORMATION FOR SEQ ID NO:82:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "SYNTHETIC DNA, N REPRESENTS INOSINE"

(x i) SEQUENCE DESCRIPTION: SEQ ID NO:82:

CATNGATTCG TTCTCTTCGT A                                          21

(2) INFORMATION FOR SEQ ID NO:83:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "SYNTHETIC DNA, N REPRESENTS INOSINE"

( x i ) SEQUENCE DESCRIPTION: SEQ ID NO:83:

CATNGATTCG TTCTCCTCAT A    21

( 2 ) INFORMATION FOR SEQ ID NO:84:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "SYNTHETIC DNA, N REPRESENTS INOSINE"

( x i ) SEQUENCE DESCRIPTION: SEQ ID NO:84:

CATNGATTCG TTCTCCTCGT A    21

( 2 ) INFORMATION FOR SEQ ID NO:85:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "SYNTHETIC DNA, N REPRESENTS INOSINE"

( x i ) SEQUENCE DESCRIPTION: SEQ ID NO:85:

CATNGACTCA TTTTCTTCAT A    21

( 2 ) INFORMATION FOR SEQ ID NO:86:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "SYNTHETIC DNA, N REPRESENTS INOSINE"

( x i ) SEQUENCE DESCRIPTION: SEQ ID NO:86:

CATNGACTCA TTTTCTTCGT A    21

( 2 ) INFORMATION FOR SEQ ID NO:87:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "SYNTHETIC DNA, N REPRESENTS INOSINE"

( x i ) SEQUENCE DESCRIPTION: SEQ ID NO:87:

CATNGACTCA TTTTCCTCAT A       21

( 2 ) INFORMATION FOR SEQ ID NO:88:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA, N REPRESENTS INOSINE"

( x i ) SEQUENCE DESCRIPTION: SEQ ID NO:88:

CATNGACTCA TTTTCCTCGT A       21

( 2 ) INFORMATION FOR SEQ ID NO:89:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA, N REPRESENTS INOSINE"

( x i ) SEQUENCE DESCRIPTION: SEQ ID NO:89:

CATNGACTCA TTCTCTTCAT A       21

( 2 ) INFORMATION FOR SEQ ID NO:90:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA, N REPRESENTS INOSINE"

( x i ) SEQUENCE DESCRIPTION: SEQ ID NO:90:

CATNGACTCA TTCTCTTCGT A       21

( 2 ) INFORMATION FOR SEQ ID NO:91:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA, N REPRESENTS INOSINE"

( x i ) SEQUENCE DESCRIPTION: SEQ ID NO:91:

CATNGACTCA TTCTCCTCAT A       21

( 2 ) INFORMATION FOR SEQ ID NO:92:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
    ( A ) DESCRIPTION: /desc = "SYNTHETIC DNA, N REPRESENTS INOSINE"

( x i ) SEQUENCE DESCRIPTION: SEQ ID NO:92:

CATNGACTCA TTCTCCTCGT A    21

( 2 ) INFORMATION FOR SEQ ID NO:93:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA, N REPRESENTS INOSINE"

( x i ) SEQUENCE DESCRIPTION: SEQ ID NO:93:

CATNGACTCG TTTTCTTCAT A    21

( 2 ) INFORMATION FOR SEQ ID NO:94:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA, N REPRESENTS INOSINE"

( x i ) SEQUENCE DESCRIPTION: SEQ ID NO:94:

CATNGACTCG TTTTCTTCGT A    21

( 2 ) INFORMATION FOR SEQ ID NO:95:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA, N REPRESENTS INOSINE"

( x i ) SEQUENCE DESCRIPTION: SEQ ID NO:95:

CATNGACTCG TTTTCCTCAT A    21

( 2 ) INFORMATION FOR SEQ ID NO:96:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA, N REPRESENTS INOSINE"

( x i ) SEQUENCE DESCRIPTION: SEQ ID NO:96:

CATNGACTCG TTTTCCTCGT A    21

( 2 ) INFORMATION FOR SEQ ID NO:97:

( i ) SEQUENCE CHARACTERISTICS:

(A) LENGTH: 21 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "SYNTHETIC DNA, N REPRESENTS INOSINE"

(xi) SEQUENCE DESCRIPTION: SEQ ID NO:97:

CATNGACTCG TTCTCTTCAT A  21

(2) INFORMATION FOR SEQ ID NO:98:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "SYNTHETIC DNA, N REPRESENTS INOSINE"

(xi) SEQUENCE DESCRIPTION: SEQ ID NO:98:

CATNGACTCG TTCTCTTCGT A  21

(2) INFORMATION FOR SEQ ID NO:99:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "SYNTHETIC DNA, N REPRESENTS INOSINE"

(xi) SEQUENCE DESCRIPTION: SEQ ID NO:99:

CATNGACTCG TTCTCCTCAT A  21

(2) INFORMATION FOR SEQ ID NO:100:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "SYNTHETIC DNA, N REPRESENTS INOSINE"

(xi) SEQUENCE DESCRIPTION: SEQ ID NO:100:

CATNGACTCG TTCTCCTCGT A  21

(2) INFORMATION FOR SEQ ID NO:101:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "SYNTHETIC DNA, N REPRESENTS INOSINE"

(xi) SEQUENCE DESCRIPTION: SEQ ID NO:101:

CATNCTTTCA TTTTCTTCAT A  21

( 2 ) INFORMATION FOR SEQ ID NO:102:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA, N REPRESENTS INOSINE"

( x i ) SEQUENCE DESCRIPTION: SEQ ID NO:102:

CATNCTTTCA TTTTCTTCGT A         21

( 2 ) INFORMATION FOR SEQ ID NO:103:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA, N REPRESENTS INOSINE"

( x i ) SEQUENCE DESCRIPTION: SEQ ID NO:103:

CATNCTTTCA TTTTCCTCAT A         21

( 2 ) INFORMATION FOR SEQ ID NO:104:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA, N REPRESENTS INOSINE"

( x i ) SEQUENCE DESCRIPTION: SEQ ID NO:104:

CATNCTTTCA TTTTCCTCGT A         21

( 2 ) INFORMATION FOR SEQ ID NO:105:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA, N REPRESENTS INOSINE"

( x i ) SEQUENCE DESCRIPTION: SEQ ID NO:105:

CATNCTTTCA TTCTCTTCAT A         21

( 2 ) INFORMATION FOR SEQ ID NO:106:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA, N REPRESENTS

INOSINE"

( x i ) SEQUENCE DESCRIPTION: SEQ ID NO:106:

CATNCTTTCA TTCTCTTCGT A                                               21

( 2 ) INFORMATION FOR SEQ ID NO:107:

( i ) SEQUENCE CHARACTERISTICS:
                ( A ) LENGTH: 21 base pairs
                ( B ) TYPE: nucleic acid
                ( C ) STRANDEDNESS: single
                ( D ) TOPOLOGY: linear ( i i ) MOLECULE TYPE: other nucleic acid
                ( A ) DESCRIPTION: /desc = "SYNTHETIC DNA, N REPRESENTS
                      INOSINE"

( x i ) SEQUENCE DESCRIPTION: SEQ ID NO:107:

CATNCTTTCA TTCTCCTCAT A                                               21

( 2 ) INFORMATION FOR SEQ ID NO:108:

( i ) SEQUENCE CHARACTERISTICS:
                ( A ) LENGTH: 21 base pairs
                ( B ) TYPE: nucleic acid
                ( C ) STRANDEDNESS: single
                ( D ) TOPOLOGY: linear ( i i ) MOLECULE TYPE: other nucleic acid
                ( A ) DESCRIPTION: /desc = "SYNTHETIC DNA, N REPRESENTS
                      INOSINE"

( x i ) SEQUENCE DESCRIPTION: SEQ ID NO:108:

CATNCTTTCA TTCTCCTCGT A                                               21

( 2 ) INFORMATION FOR SEQ ID NO:109:

( i ) SEQUENCE CHARACTERISTICS:
                ( A ) LENGTH: 21 base pairs
                ( B ) TYPE: nucleic acid
                ( C ) STRANDEDNESS: single
                ( D ) TOPOLOGY: linear ( i i ) MOLECULE TYPE: other nucleic acid
                ( A ) DESCRIPTION: /desc = "SYNTHETIC DNA, N REPRESENTS
                      INOSINE"

( x i ) SEQUENCE DESCRIPTION: SEQ ID NO:109:

CATNCTTTCG TTTTCTTCAT A                                               21

( 2 ) INFORMATION FOR SEQ ID NO:110:

( i ) SEQUENCE CHARACTERISTICS:
                ( A ) LENGTH: 21 base pairs
                ( B ) TYPE: nucleic acid
                ( C ) STRANDEDNESS: single
                ( D ) TOPOLOGY: linear ( i i ) MOLECULE TYPE: other nucleic acid
                ( A ) DESCRIPTION: /desc = "SYNTHETIC DNA, N REPRESENTS
                      INOSINE"

( x i ) SEQUENCE DESCRIPTION: SEQ ID NO:110:

CATNCTTTCG TTTTCTTCGT A                                               21

( 2 ) INFORMATION FOR SEQ ID NO:111:

( i ) SEQUENCE CHARACTERISTICS:
                ( A ) LENGTH: 21 base pairs
                ( B ) TYPE: nucleic acid ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA, N REPRESENTS
            INOSINE"

( x i ) SEQUENCE DESCRIPTION: SEQ ID NO:111:

CATNCTTTCG TTTTCCTCAT A                    21

( 2 ) INFORMATION FOR SEQ ID NO:112:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA, N REPRESENTS
            INOSINE"

( x i ) SEQUENCE DESCRIPTION: SEQ ID NO:112:

CATNCTTTCG TTTTCCTCGT A                    21

( 2 ) INFORMATION FOR SEQ ID NO:113:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA, N REPRESENTS
            INOSINE"

( x i ) SEQUENCE DESCRIPTION: SEQ ID NO:113:

CATNCTTTCG TTCTCTTCAT A                    21

( 2 ) INFORMATION FOR SEQ ID NO:114:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA, N REPRESENTS
            INOSINE"

( x i ) SEQUENCE DESCRIPTION: SEQ ID NO:114:

CATNCTTTCG TTCTCTTCGT A                    21

( 2 ) INFORMATION FOR SEQ ID NO:115:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA, N REPRESENTS
            INOSINE"

( x i ) SEQUENCE DESCRIPTION: SEQ ID NO:115:

CATNCTTTCG TTCTCCTCAT A                    21

( 2 ) INFORMATION FOR SEQ ID NO:116:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA, N REPRESENTS
            INOSINE"

( x i ) SEQUENCE DESCRIPTION: SEQ ID NO:116:

CATNCTTTCG TTCTCCTCGT A                                      21

( 2 ) INFORMATION FOR SEQ ID NO:117:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA, N REPRESENTS
            INOSINE"

( x i ) SEQUENCE DESCRIPTION: SEQ ID NO:117:

CATNCTTTCG TTCTCCTCGT A                                      21

( 2 ) INFORMATION FOR SEQ ID NO:118:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA, N REPRESENTS
            INOSINE"

( x i ) SEQUENCE DESCRIPTION: SEQ ID NO:118:

CATNCTCTCA TTTCTTCGT A                                      21

( 2 ) INFORMATION FOR SEQ ID NO:119:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA, N REPRESENTS
            INOSINE"

( x i ) SEQUENCE DESCRIPTION: SEQ ID NO:119:

CATNCTCTCA TTTCCTCAT A                                      21

( 2 ) INFORMATION FOR SEQ ID NO:120:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA, N REPRESENTS
            INOSINE"

( x i ) SEQUENCE DESCRIPTION: SEQ ID NO:120:

CATNCTCTCA TTTTCCTCGT A 21

( 2 ) INFORMATION FOR SEQ ID NO:121:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA, N REPRESENTS INOSINE"

( x i ) SEQUENCE DESCRIPTION: SEQ ID NO:121:

CATNCTCTCA TTCTCTTCAT A 21

( 2 ) INFORMATION FOR SEQ ID NO:122:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA, N REPRESENTS INOSINE"

( x i ) SEQUENCE DESCRIPTION: SEQ ID NO:122:

CATNCTCTCA TTCTCTTCGT A 21

( 2 ) INFORMATION FOR SEQ ID NO:123:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA, N REPRESENTS INOSINE"

( x i ) SEQUENCE DESCRIPTION: SEQ ID NO:123:

CATNCTCTCA TTCTCCTCAT A 21

( 2 ) INFORMATION FOR SEQ ID NO:124:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA, N REPRESENTS INOSINE"

( x i ) SEQUENCE DESCRIPTION: SEQ ID NO:124:

CATNCTCTCA TTCTCCTCGT A 21

( 2 ) INFORMATION FOR SEQ ID NO:125:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear (i i) MOLECULE TYPE: other nucleic acid
        (A) DESCRIPTION: /desc = "SYNTHETIC DNA, N REPRESENTS INOSINE"

(x i) SEQUENCE DESCRIPTION: SEQ ID NO:125:

CATNCTCTCG TTTTCTTCAT A      21

(2) INFORMATION FOR SEQ ID NO:126:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "SYNTHETIC DNA, N REPRESENTS INOSINE"

(x i) SEQUENCE DESCRIPTION: SEQ ID NO:126:

CATNCTCTCG TTTTCTTCGT A      21

(2) INFORMATION FOR SEQ ID NO:127:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "SYNTHETIC DNA, N REPRESENTS INOSINE"

(x i) SEQUENCE DESCRIPTION: SEQ ID NO:127:

CATNCTCTCG TTTTCCTCAT A      21

(2) INFORMATION FOR SEQ ID NO:128:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "SYNTHETIC DNA, N REPRESENTS INOSINE"

(x i) SEQUENCE DESCRIPTION: SEQ ID NO:128:

CATNCTCTCG TTTTCCTCGT A      21

(2) INFORMATION FOR SEQ ID NO:129:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "SYNTHETIC DNA, N REPRESENTS INOSINE"

(x i) SEQUENCE DESCRIPTION: SEQ ID NO:129:

CATNCTCTCG TTCTCTTCAT A      21

(2) INFORMATION FOR SEQ ID NO:130:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA, N REPRESENTS
              INOSINE"

( x i ) SEQUENCE DESCRIPTION: SEQ ID NO:130:

CATNCTCTCG TTCTCTTCGT A                                                   21

( 2 ) INFORMATION FOR SEQ ID NO:131:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA, N REPRESENTS
              INOSINE"

( x i ) SEQUENCE DESCRIPTION: SEQ ID NO:131:

CATNCTCTCG TTCTCCTCAT A                                                   21

( 2 ) INFORMATION FOR SEQ ID NO:132:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA, N REPRESENTS
              INOSINE"

( x i ) SEQUENCE DESCRIPTION: SEQ ID NO:132:

CATNCTCTCG TTCTCCTCGT A                                                   21

( 2 ) INFORMATION FOR SEQ ID NO:133:

( i ) SEQUENCE CHARACTERISTICS:
        ( A ) LENGTH: 325 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Pagrus major ( i x ) FEATURE:
        ( A ) NAME/KEY: misc_feature
        ( B ) LOCATION: 1..325

( x i ) SEQUENCE DESCRIPTION: SEQ ID NO:133:

CGATGGACCG GCAGCGTGCC GATCCTCCAA CAGTGGAGCA AGGCCGGGGT GAGGCCGGTC          60

AAATATGGCC AGTGCTGGGT GTTGCTGCC GTCGCCTGCA CAGTGCTGCG CTGCCTGGGA         120

ATCCCAACAC GCCCCATCAC CAACTTCGCT TCAGCCCATG ATGTCGATGG TAACCTCTCG        180

GTAGACTTCC TGCTGAATGA GAGACTGGAG AGCTTGGACA GTAGACAGAG AAGTGACAGT        240

AGCTGGAACT TCCACTGTTG GGTTGAATCC TGGATGAGCA GAGAGGATCT CCCTGAAGGA        300

AATGATGGCT GGCAGGTTTT GGATC                                              325

( 2 ) INFORMATION FOR SEQ ID NO:134:

( i ) SEQUENCE CHARACTERISTICS:
        ( A ) LENGTH: 1345 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Cavia porecllus ( i x ) FEATURE:
        ( A ) NAME/KEY: misc_feature
        ( B ) LOCATION: 1..1345

( x i ) SEQUENCE DESCRIPTION: SEQ ID NO:134:

```
CCTCCACTGG TTACCAGGGC TCCAGCTTCG TACTGGGCCA CTTCATCCTG CTCTACAATC      60
CTCGGTGCCC AGCGGATGCT GTCTATATGG ACTCAGACCA AGAGCGGCAG GAGTATGTGC     120
TCACCCAACA GGGCTTCATC TACCAGGGCT CGGCCAAGTT CATCAATGGC ATACCTTGGA     180
ACTTCGGGCA GTTTGAAGAT GGGATCCTGG ATATTTGCCT GATGCTCTTG GACACCAACC     240
CCAAGTTCCT GAAGAATGCT GGCCAAGACT GCTCGCGCCG CAGCAGACCT GTCTACGTGG     300
GCCGGGTGGT GAGCGCCATG GTCAACTGCA ATGACGATCA GGGCGTGCTT CAGGGACGCT     360
GGGACAACAA CTACAGTGAT GGTGTCAGCC CCATGTCCTG GATCGGCAGC GTGGACATCC     420
TGCGGCGCTG GAAAGACTAT GGGTGCCAGC GCGTCAAGTA CGGCCAGTGC TGGGTCTTCG     480
CTGCTGTGGC CTGCACAGTG CTGCGGTGCC TTGGCATCCC CACCCGAGTC GTGACCAACT     540
TTAACTCAGC CCACGACCAG AACAGCAACC TGCTCATCGA GTACTTCCGA AACGAGTCTG     600
GGGAGATCGA GGGGAACAAG AGCGAGATGA TCTGGAACTT CCACTCACTG CTGGGTGGAG     660
TCGTGGATGA CCAGGCCGGA CCTGGAGCCT GGGTACGAGG GGTGCAGGCC CTGGACCCCA     720
CACCCCAGGA GAAGAGTGAA GGGACATACT GCTGTGGCCC AGTTCCGGTT CGAGCCATCA     780
AGGAGGGCCA CCTGAACGTC AAGTATGATG CACCTTTCGT GTTTGCTGAG GTCAATGCTG     840
ACGTGGTGAA CTGGATCCGG CAGAAAGATG GGTCCCTGCG CAAGTCCATC AACCATTTGG     900
TTGTGGGGCT GAAGATCAGT ACTAAGAGTG TGGGCCGCGA TGAGCGAGAG GACATCACCC     960
ACACCTACAA GTACCCAGAG GGATCTGAAG AGGAGCGGGA AGCTTTTGTT AGGGCCAACC    1020
ACCTAAATAA ACTGGCCACA AAGGAAGAGG CTCAGGAGGA AACGGGAGTG GCCATGCGGA    1080
TCCGTGTGGG CCAGAACATG ACTATGGGCA GTGACTTTGA CATCTTTGCC TACATCACCA    1140
ATGGCACTGC TGAGAGCCAC GAATGCCAAC TCCTGCTCTG TGCACGCATC GTCAGCTACA    1200
ATGGAGTCCT GGGGCCCGTG TGCAGCACCA ACGACCTGCT CAACCTGACC CTGGATCCCT    1260
TCTCGGAGAA CAGCATCCCC CTGCACATCC TCTATGAGAA GTACGGTGAC TACCTGACTG    1320
AGTCCAACCT CATCAAGGTG CGAGG                                          1345
```

( 2 ) INFORMATION FOR SEQ ID NO:135:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:135:

```
GTCAAGTACG GCCAGTGCTG GGTCTTCGC                                        29
```

( 2 ) INFORMATION FOR SEQ ID NO:136:

( i ) SEQUENCE CHARACTERISTICS:
        ( A ) LENGTH: 3394 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Crassostrea gigas ( i x ) FEATURE:
        ( A ) NAME/KEY: CDS
        ( B ) LOCATION: 305..2617

( x i ) SEQUENCE DESCRIPTION: SEQ ID NO:136:

```
TGGAGAGATG GTAAAATTTT AAAATGTACA GATAACGTTA CCGTGCAAGA GCCAAGACAG      60

GAAAAAGGCA TTCAGCTGTG AAGGCCACTG CAGTAGAGTT TCATGTGGAA AATGTCGAAA     120

TCCCTTTCTA TCTTTTTTTT TCATTTACTC CGATGCACGT TTTAGAGTCG GTATTCGTTC     180

TGGCAGCATG TAATAGTTGT AATTTCTATT GAATTGGGGC TGCATTTAAA TTTCAAAACG     240

AGTTGTTAAA GAAATTTACG AATCGGTGTG CTATTTTCAT ACGTCGTCCG TTGTGGAATA     300

TATC ATG GCT TTT TGG GGC GTC TTT TAC ACG ATA TAC TCG GGG ATT CGT      349
     Met Ala Phe Trp Gly Val Phe Tyr Thr Ile Tyr Ser Gly Ile Arg
       1               5                  10                  15

CGC ATT GCT GGA CAA CCC CCC GAG GAA GAT ACT AGT GAT AAA GAG CAG      397
Arg Ile Ala Gly Gln Pro Pro Glu Glu Asp Thr Ser Asp Lys Glu Gln
             20                  25                  30

AAA AGG AGC AGA ACT AAA AAA GCA TTG GGC AGT GAA GAA GAA GAG GGA      445
Lys Arg Ser Arg Thr Lys Lys Ala Leu Gly Ser Glu Glu Glu Glu Gly
             35                  40                      45

CGC ATC TCC TCC CTG TCT GAT GAA GAC TTA CGA GCA AGG AAT AAG GTC      493
Arg Ile Ser Ser Leu Ser Asp Glu Asp Leu Arg Ala Arg Asn Lys Val
             50                  55                  60

CTC GAA CCA AAG GAC GAA CCA TCT GCG ACT TTG AAT GTA AGT TCT GTA      541
Leu Glu Pro Lys Asp Glu Pro Ser Ala Thr Leu Asn Val Ser Ser Val
     65                  70                      75

GAT TGT CAG ACA AAA CTG AAC AGA AAG AAC CAC CAC ACC AAT GAA TTT      589
Asp Cys Gln Thr Lys Leu Asn Arg Lys Asn His His Thr Asn Glu Phe
 80                      85                  90                  95

GAA AAA GCC GGA AAT ATC TAC AGA AGG GGA CAG GCT TTT GTT ATC CGT      637
Glu Lys Ala Gly Asn Ile Tyr Arg Arg Gly Gln Ala Phe Val Ile Arg
                    100                 105                 110

GTT GAA TTT GAT AGG GAA GTC AAT TCA GAC CAT GAC GTC ATA CTG CTG      685
Val Glu Phe Asp Arg Glu Val Asn Ser Asp His Asp Val Ile Leu Leu
                115                 120                 125

CAG TTT ACT TAC GGT TCA CGC CCT CAA GAA AGC AAA GGA ACT GTT ATC      733
Gln Phe Thr Tyr Gly Ser Arg Pro Gln Glu Ser Lys Gly Thr Val Ile
        130                 135                 140

AGA ATT CCC CTT GAT TTA AAA CCA ACA ACA AAA ACA TCC GAC GTC ACA      781
Arg Ile Pro Leu Asp Leu Lys Pro Thr Thr Lys Thr Ser Asp Val Thr
    145                 150                 155

GAA ACA TGG TTT GCG GAA GTG AAG AAT ATT GCC GGG AAA GGT CTG GAG      829
Glu Thr Trp Phe Ala Glu Val Lys Asn Ile Ala Gly Lys Gly Leu Glu
160                 165                 170                 175

TGC GCG ATT ACG TCA GCA CCT GAC AGC AGT ATT GGG GAA TAC CGT TTC      877
Cys Ala Ile Thr Ser Ala Pro Asp Ser Ser Ile Gly Glu Tyr Arg Phe
                180                 185                 190

TAC ATA GAG ACA AAT CTG AAG GAC ACG GAT GCC GTC AAG AGA TAC GAA      925
```

```
Tyr Ile Glu Thr Asn Leu Lys Asp Thr Asp Ala Val Lys Arg Tyr Glu
        195                 200                 205

GAG AAT GAA TCA ATG ATC ATT CTC TTC AAT GCT TGG GCG AAA GAG GAT      973
Glu Asn Glu Ser Met Ile Ile Leu Phe Asn Ala Trp Ala Lys Glu Asp
        210                 215                 220

ACA GTG TAC ATG GAC AAG GAG GGA GAG AGG GGG GAG TAC GTC CTG AAC     1021
Thr Val Tyr Met Asp Lys Glu Gly Glu Arg Gly Glu Tyr Val Leu Asn
225                 230                 235

GAG ACC GGA AGA GTC TGG ACA AGC CGC ACG TGG TAT GGA CGA CCA TGG     1069
Glu Thr Gly Arg Val Trp Thr Ser Arg Thr Trp Tyr Gly Arg Pro Trp
240                 245                 250                 255

AAT TTT GGA CAA TTT GAT GAC CCT GTG CTA GAC GTT GCC CTA CAA TTG     1117
Asn Phe Gly Gln Phe Asp Asp Pro Val Leu Asp Val Ala Leu Gln Leu
                260                 265                 270

TTA CTG GAG GGA GGT TTA TCA GAC GTG GCA TGT ACT TCT CCT GTG TCC     1165
Leu Leu Glu Gly Gly Leu Ser Asp Val Ala Cys Thr Ser Pro Val Ser
            275                 280                 285

GTG ATC CGC TGC CTG TCG TCA CTG TGC AAT TCC TGT GAC AAT AAT GGA     1213
Val Ile Arg Cys Leu Ser Ser Leu Cys Asn Ser Cys Asp Asn Asn Gly
        290                 295                 300

GTT CTG GCG GGT AGA TGG ACA AAG GAG TAT CCC AAG GAC TGC ACA GTA     1261
Val Leu Ala Gly Arg Trp Thr Lys Glu Tyr Pro Lys Asp Cys Thr Val
305                 310                 315

CCC TGG AAG TGG ACA GGA AGT GTC GCA ATC ATC AAA GAG TAC CAC ACC     1309
Pro Trp Lys Trp Thr Gly Ser Val Ala Ile Ile Lys Glu Tyr His Thr
320                 325                 330                 335

AAC GGT AAC AAG CCC GTA CGA TAC GGA CAG TGC TGG GTG TTT TCC GGT     1357
Asn Gly Asn Lys Pro Val Arg Tyr Gly Gln Cys Trp Val Phe Ser Gly
                340                 345                 350

CTT CTT ACC ACA ATG TGT CGC TGC CTC GGA ATA CCG ACC CGG TCT GTG     1405
Leu Leu Thr Thr Met Cys Arg Cys Leu Gly Ile Pro Thr Arg Ser Val
            355                 360                 365

ACA AAC TTT GAT TCT GCG CAT GAC ACC GAC AGC AGC ATG ACG ATT GAC     1453
Thr Asn Phe Asp Ser Ala His Asp Thr Asp Ser Ser Met Thr Ile Asp
        370                 375                 380

AGC CAT TGG GAC GAG GAC GGG GAA CCA TTA GAA GAC ATG AAC GAC TCT     1501
Ser His Trp Asp Glu Asp Gly Glu Pro Leu Glu Asp Met Asn Asp Ser
385                 390                 395

GTT TGG AAT TTC CAT GTA TGG AAC GAG TCT TGG TTC CGA CGT TTA GAC     1549
Val Trp Asn Phe His Val Trp Asn Glu Ser Trp Phe Arg Arg Leu Asp
400                 405                 410                 415

CTT CCC GAG GGT TAC GAT GGT TGG CAG GCT CAT GAT GCC ACG CCT CAG     1597
Leu Pro Glu Gly Tyr Asp Gly Trp Gln Ala His Asp Ala Thr Pro Gln
                420                 425                 430

GAA GCA AGC GAA GGA ATT ATG AGA TGC GGC CCG GCT CCT CTG ACA GCC     1645
Glu Ala Ser Glu Gly Ile Met Arg Cys Gly Pro Ala Pro Leu Thr Ala
            435                 440                 445

ATC AAA GAG GGT CAC GTG TAC CTG AAC TTT GAC ATA CCC TTT GTC TTT     1693
Ile Lys Glu Gly His Val Tyr Leu Asn Phe Asp Ile Pro Phe Val Phe
        450                 455                 460

GGC GAG GTC AAC GGA GAT CGA GTT CAG TGG GTG GTG AAG AAG GAC GGT     1741
Gly Glu Val Asn Gly Asp Arg Val Gln Trp Val Val Lys Lys Asp Gly
465                 470                 475

ACA ATG GAG GTA AGC CAG ATA GAT CAC TCC GCG GTG GGA CAC TAC ATC     1789
Thr Met Glu Val Ser Gln Ile Asp His Ser Ala Val Gly His Tyr Ile
480                 485                 490                 495

AGC ACC AAG AGG ATG GGC TCA AAC GAC CGT GAG GAC GTC ACA AAC CTG     1837
Ser Thr Lys Arg Met Gly Ser Asn Asp Arg Glu Asp Val Thr Asn Leu
                500                 505                 510

TAC AAA TAC CCG GAT GGA AGT GAA CAA GAA AGA AGA GTT GCC AAA TTT     1885
```

| | | | | | | | | | | | | | | | | |
|---|---|---|---|---|---|---|---|---|---|---|---|---|---|---|---|---|
| | Tyr | Lys | Tyr | Pro 515 | Asp | Gly | Ser | Glu 520 | Gln | Arg | Arg | Val | Ala 525 | Lys | Phe | |
| GTG | AAC | AGA | TAC | AGT | ACA | AGA | AGG | AAG | CAG | AAT | ATC | TAC | AAG | CTG | GAC | 1933 |
| Val | Asn | Arg 530 | Tyr | Ser | Thr | Arg | Arg 535 | Lys | Gln | Asn | Ile | Tyr 540 | Lys | Leu | Asp | |
| ACC | ACC | AAG | GTG | TTA | AAG | TTT | ACC | GTT | AGC | CCG | CCA | GAT | AAC | ACA | CTG | 1981 |
| Thr | Thr | Lys 545 | Val | Leu | Lys | Phe | Thr 550 | Val | Ser | Pro | Pro | Asp 555 | Asn | Thr | Leu | |
| ATT | GGA | GAC | GAT | ATG | GAG | ATT | AAG | GTG | GCC | GTC | AAA | AAC | ACA | GCC | GAT | 2029 |
| Ile 560 | Gly | Asp | Asp | Met | Glu 565 | Ile | Lys | Val | Ala | Val 570 | Lys | Asn | Thr | Ala | Asp 575 | |
| GGA | CCC | CTT | AAA | CTT | CAT | CTG | ACT | GTG | TCA | CTG | GTC | AAT | GCT | TAC | TAC | 2077 |
| Gly | Pro | Leu | Lys | Leu 580 | His | Leu | Thr | Val | Ser 585 | Leu | Val | Asn | Ala | Tyr 590 | Tyr | |
| ACT | GGG | GTG | GCG | GGG | TCA | AGG | GTC | AAG | ACG | CAG | ACG | TTT | GAG | GAA | ACC | 2125 |
| Thr | Gly | Val | Ala | Gly 595 | Ser | Arg | Val | Lys | Thr 600 | Gln | Thr | Phe | Glu | Glu 605 | Thr | |
| ATA | AAA | GCG | AAA | GAT | GAG | AAG | ATA | GTA | ACT | ATG | CCC | GTT | AAA | GGG | ACA | 2173 |
| Ile | Lys | Ala | Lys 610 | Asp | Glu | Lys | Ile | Val 615 | Thr | Met | Pro | Val | Lys 620 | Gly | Thr | |
| GAG | TAT | CAC | GAT | GGA | ATG | AAC | CCC | GAA | GGA | CGA | TTC | CAG | TTG | TAC | ATC | 2221 |
| Glu | Tyr | His 625 | Asp | Gly | Met | Asn | Pro 630 | Glu | Gly | Arg | Phe | Gln 635 | Leu | Tyr | Ile | |
| TCT | GGG | AAG | AAC | ATA | GAC | TCG | GGC | AGC | ATG | GAA | TCC | ACG | CAA | ATC | TCC | 2269 |
| Ser 640 | Gly | Lys | Asn | Ile | Asp 645 | Ser | Gly | Ser | Met | Glu 650 | Ser | Thr | Gln | Ile | Ser 655 | |
| TTT | GTA | CTG | AAG | AAA | CCA | CAA | CTT | GTT | ATA | CAG | GTT | CCT | CAA | ACC | ATT | 2317 |
| Phe | Val | Leu | Lys | Lys 660 | Pro | Gln | Leu | Val | Ile 665 | Gln | Val | Pro | Gln | Thr 670 | Ile | |
| GAA | GCG | AAA | GAG | GAA | ACG | GAG | GCC | ACC | ATT | GTG | TTC | AAG | AAC | ACG | ACA | 2365 |
| Glu | Ala | Lys | Glu | Glu 675 | Thr | Glu | Ala | Thr | Ile 680 | Val | Phe | Lys | Asn | Thr 685 | Thr | |
| CAG | CTC | GTG | CTC | ACC | CAG | GCT | GAA | ATA | GCC | GTG | GAG | GGC | TCG | GGT | CTC | 2413 |
| Gln | Leu | Val | Leu | Thr 690 | Gln | Ala | Glu | Ile | Ala 695 | Val | Glu | Gly | Ser | Gly 700 | Leu | |
| CTA | GCT | CCA | CAA | ACC | ATA | GAT | ATA | AGC | AGT | CCT | ATT | AAA | CCT | GGT | GAC | 2461 |
| Leu | Ala | Pro 705 | Gln | Thr | Ile | Asp | Ile 710 | Ser | Ser | Pro | Ile | Lys 715 | Pro | Gly | Asp | |
| GAG | GTC | AAG | AAA | ACA | GTC | GTC | CTT | CGC | CCC | CGC | AAA | CCA | TAC | TAC | TGG | 2509 |
| Glu | Val 720 | Lys | Lys | Thr | Val 725 | Val | Leu | Arg | Pro | Arg 730 | Lys | Pro | Tyr | Tyr | Trp 735 | |
| GGT | CGT | GAA | CTG | ATA | GCG | ACC | TTC | ACC | TCC | AAA | CAG | ATT | GTC | GAC | ATT | 2557 |
| Gly | Arg | Glu | Leu | Ile 740 | Ala | Thr | Phe | Thr | Ser 745 | Lys | Gln | Ile | Val | Asp 750 | Ile | |
| GAG | ACC | AGC | GCC | GAC | ATT | AAG | GTG | ATC | CGA | CAG | AAC | AAA | GAT | AAC | GAC | 2605 |
| Glu | Thr | Ser | Ala 755 | Asp | Ile | Lys | Val | Ile 760 | Arg | Gln | Asn | Lys | Asp 765 | Asn | Asp | |
| AGC | GAC | AGT | GAC | TAGAGAATTC | | CCACCGTCCG | | ACTGTGCTAG | | AAATCCAAAG | | | | | | 2657 |
| Ser | Asp | Ser 770 | Asp | | | | | | | | | | | | | |

| | | |
|---|---|---|
| ATTCATTGAC TTTATTTTCA CTTATCAAAC ACTTTCCCTA TTCGTGAACG TGTTTACTTG | | 2717 |
| TCCCAAACCC ACACTGTTTA GAATAGAATC TCTGTTGTAT ACAAAGCATC CTCTAACGTA | | 2777 |
| ACTGAGACAT AATGACAAGC ATTGTTTACC TTGTAAATTT ATTGTTTTCC ATGTATCCAT | | 2837 |
| ATTGCGAATT ATGAGATTTC GCTATTCCGT GCAAGTCATT TGTTTTGTGT GCAGCTAATA | | 2897 |
| TTATGTTAGT TTATTCCTAG AATGACATTT TATTTTCAAA AATGTCTTAA TCAATTAACT | | 2957 |
| ATAATAATCC TAGTTTTTTC CATTGTTCTT TTTTCCTTGT TCTTTTTGGA GTTCGTTTAT | | 3017 |
| AATCTCCACA AATTTTGAAA CGCTTCCATT AAAGAAGCCA TATATACTAA AAAAAAAAA | | 3077 |

```
ACCCCCCCCC CCCATTATGG ATCCACCCTC CCCCCGGAGT AATGATTTAT ACAAATTTGT    3137

AAATACACTA TATAAGGATG GCCCACACAA GTTTAGCTT  TCTTTGAGAA TATTTTTAAG    3197

GATTTACACT TTATATTCCT ATGTAAAAGT TCACCCCCCC CCCATTGTGG CTCCATCCTC    3257

CACCCGGAGT TATGATTTTC ACAATGTGT  TTCTACTCTA GACAAGGATG CTTCCACACA    3317

AGTGTCAGTT TTTCTGGCTG ATAAGTTTCT GAGAAGGAGA TTTCAAAGA  TTTACATTAT    3377

ATATTCCTAT GTAAAAG                                                  3394
```

( 2 ) INFORMATION FOR SEQ ID NO:137:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:137:

```
TGTGGAATAT ACCATGGC                                                   18
```

( 2 ) INFORMATION FOR SEQ ID NO:138:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:138:

```
GTGGTTCTTT CTGTTCAG                                                   18
```

( 2 ) INFORMATION FOR SEQ ID NO:139:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:139:

```
TTCTAATGAT GATGATGATG ATGGTCACTG TCGCTGTCGT T                         41
```

( 2 ) INFORMATION FOR SEQ ID NO:140:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:140:

```
ACGAGGTCAA GAAAACAG                                                   18
```

( 2 ) INFORMATION FOR SEQ ID NO:141:

( i ) SEQUENCE CHARACTERISTICS:
        ( A ) LENGTH: 7 amino acids
        ( B ) TYPE: amino acid
        ( C ) STRANDEDNESS: single (D) TOPOLOGY: linear (ii) MOLECULE TYPE: peptide (vi) ORIGINAL SOURCE:
        (A) ORGANISM: Crassostrea gigas (xi) SEQUENCE DESCRIPTION: SEQ ID NO:141:

His His Thr Asn Glu Phe Glu
    1               5

(2) INFORMATION FOR SEQ ID NO:142:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Crassostrea gigas (xi) SEQUENCE DESCRIPTION: SEQ ID NO:142:

Tyr Glu Glu Asn Glu Ser Met
    1               5

(2) INFORMATION FOR SEQ ID NO:143:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: other nucleic acid (xi) SEQUENCE DESCRIPTION: SEQ ID NO:143:

Gly Gly Gln Gly
    1

(2) INFORMATION FOR SEQ ID NO:144:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: other nucleic acid (xi) SEQUENCE DESCRIPTION: SEQ ID NO:144:

Asn His His Thr Asn Glu Phe Glu Lys
    1               5

(2) INFORMATION FOR SEQ ID NO:145:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: other nucleic acid (xi) SEQUENCE DESCRIPTION: SEQ ID NO:145:

Asp Cys Thr Val Pro Trp Lys
    1               5

( 2 ) INFORMATION FOR SEQ ID NO:146:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:146:

```
Trp Thr Gly Ser Val Ala Ile Ile Lys
1               5
```

( 2 ) INFORMATION FOR SEQ ID NO:147:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:147:

```
Asp Gly Thr Met Glu Val Ser Gln Ile Asp His Ser Ala Val Gly
1               5                   10                  15
```

( 2 ) INFORMATION FOR SEQ ID NO:148:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:148:

```
Tyr Glu Glu Asn Glu Ser Met Ile Ile Leu Phe Asn
1               5                   10
```

( 2 ) INFORMATION FOR SEQ ID NO:149:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:149:

```
Ala Phe Trp Gly Val Phe Tyr
1               5
```

( 2 ) INFORMATION FOR SEQ ID NO:150:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:150:

```
Met Ala Phe Trp Gly Val Phe Tyr
1               5
```